(12) United States Patent
Benner et al.

(10) Patent No.: US 8,871,469 B1
(45) Date of Patent: Oct. 28, 2014

(54) SELF-AVOIDING MOLECULAR RECOGNITION SYSTEMS IN DNA PRIMING

(76) Inventors: Steven Albert Benner, Gainesville, FL (US); Shuichi Hoshika, Gainesville, FL (US); Fei Chen, Gainesville, FL (US)

( * ) Notice: Subject to any disclaimer, the term of this patent is extended or adjusted under 35 U.S.C. 154(b) by 1394 days.

(21) Appl. No.: 12/229,159

(22) Filed: Aug. 20, 2008

Related U.S. Application Data

(63) Continuation-in-part of application No. 11/647,609, filed on Dec. 30, 2006, now abandoned, which is a continuation of application No. 11/271,366, filed on Nov. 12, 2005, now abandoned.

(60) Provisional application No. 60/627,460, filed on Nov. 13, 2004, provisional application No. 60/627,459, filed on Nov. 13, 2004.

(51) Int. Cl.
*C12P 19/34* (2006.01)
*C07H 21/04* (2006.01)

(52) U.S. Cl.
USPC .................................. 435/91.1; 536/23.1

(58) Field of Classification Search
USPC .................................. 435/91.1; 536/23.1
See application file for complete search history.

(56) References Cited

U.S. PATENT DOCUMENTS

| | | | |
|---|---|---|---|
| 5,432,272 A * | 7/1995 | Benner | 536/25.3 |
| 7,371,580 B2 * | 5/2008 | Yakhini et al. | 436/94 |
| 2008/0146787 A1 * | 6/2008 | Timar et al. | 536/23.1 |

OTHER PUBLICATIONS

Ahlborn et al. Isostable DNA. J. Am. Chem. Soc. 2007, 129(49):15218-15232.*

* cited by examiner

*Primary Examiner* — Jezia Riley

(57) ABSTRACT

This invention concerns self-avoiding molecular recognition systems (SAMRS), compositions that bind to natural DNA and RNA, but do not bind to compositions at sites that incorporate other SAMRS components, and processes dependent on them. Their utility is shown by discoveries that DNA polymerases accept these compositions as primers and templates, where standard triphosphates are added to primers containing SAMRS components, and added opposite to SAMRS components in the template. A critical mass of data are provided in 16 examples to provide first-generation heuristic rules to permit design of SAMRS sequences can be used as primers and templates that are accepted by DNA polymerases. The presently preferred primers are at least 12 nucleotide units in length, and more preferably between 15 and 30 nucleotides in length. Also preferred are chimeric primers that have standard nucleotides in their 5'-segments, and SAMRS nucleotides in their 3'-segments, and in multiplexed priming.

16 Claims, 18 Drawing Sheets

SEQUENCE LISTING

<160> NUMBER OF SEQ ID NOS: 124

<210> SEQ ID NO 1
<211> LENGTH: 25
<212> TYPE: DNA
<213> ORGANISM: Artificial Sequence
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = hypoxanthine, nonstandard nucleotide of the
      invention
<220> FEATURE:
<221> NAME/KEY: misc_feature
<222> LOCATION: (23)..(23)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: nonstandard nucleotide of the invention
<220> FEATURE:
<223> OTHER INFORMATION: Synthetic

<400> SEQUENCE: 1
tatctgcgtg ccctgtctct nnnng                                           25

<210> SEQ ID NO 2
<211> LENGTH: 25
<212> TYPE: DNA
<213> ORGANISM: Artificial Sequence
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 2
ccaatgccaa cctctacctc nnnng                                           25

<210> SEQ ID NO 3
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of

```
      the invention
<220> FEATURE:
<221> NAME/KEY: misc_feature
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = hypoxanthine, nonstandard nucleotide of the
      invention
<220> FEATURE:
<221> NAME/KEY: misc_feature
<222> LOCATION: (23)..(23)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = hypoxanthine, nonstandard nucleotide of the
      invention
<220> FEATURE:
<223> OTHER INFORMATION: Synthetic

<400> SEQUENCE: 3
tatctgcgtg ccctgtnnnn nnnng                                          25

<210> SEQ ID NO 4
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<222> LOCATION: (18)..(18)
<223> OTHER INFORMATION: n = N4-ethylcytosine, nonstandard nucleotide of
      the invention
<220> FEATURE:
<222> LOCATION: (19)..(19)
<223> OTHER INFORMATION: n = 2-thiothymine, nonstandard nucleotide of
      the invention
<220> FEATURE:
<222> LOCATION: (20)..(20)
<223> OTHER INFORMATION: n = N4-ethylcytosine, nonstandard nucleotide of
      the invention
<220> FEATURE:
<222> LOCATION: (21)..(21)
<223> OTHER INFORMATION: n = N4-ethylcytosine, nonstandard nucleotide of
      the invention
<220> FEATURE:
<222> LOCATION: (22)..(22)
<223> OTHER INFORMATION: n = 2-aminopurine, nonstandard nucleotide of
      the invention
<220> FEATURE:
<222> LOCATION: (23)..(23)
<223> OTHER INFORMATION: n = hypoxanthine, nonstandard nucleotide of the
      invention
<220> FEATURE:
<222> LOCATION: (24)..(24)
<223> OTHER INFORMATION: n = 2-aminopurine, nonstandard nucleotide of
      the invention
<220> FEATURE:
<223> OTHER INFORMATION: Synthetic
```

```
<400> SEQUENCE: 4
ccaatgccaa cctctannnn nnnng                                          25

<210> SEQ ID NO 5
<211> LENGTH: 15
<212> TYPE: DNA
<213> ORGANISM: Artificial Sequence
<220> FEATURE:
<223> OTHER INFORMATION: Synthetic

<400> SEQUENCE: 5
accaagcaat caagt                                                     15

<210> SEQ ID NO 6
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-aminopurine, nonstandard nucleotide of
      the invention
<220> FEATURE:
<223> OTHER INFORMATION: Synthetic

<400> SEQUENCE: 6
accaagcnat caagt                                                     15

<210> SEQ ID NO 7
<211> LENGTH: 15
<212> TYPE: DNA
<213> ORGANISM: Artificial Sequence
<220> FEATURE:
<223> OTHER INFORMATION: Synthetic

<400> SEQUENCE: 7
accaagctat caagt                                                     15

<210> SEQ ID NO 8
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<223> OTHER INFORMATION: Synthetic

<400> SEQUENCE: 8
accaagcnat caagt                                                     15

<210> SEQ ID NO 9
<211> LENGTH: 15
<212> TYPE: DNA
<213> ORGANISM: Artificial Sequence
<220> FEATURE:
<223> OTHER INFORMATION: Synthetic

<400> SEQUENCE: 9
accaagcgat caagt                                                     15

<210> SEQ ID NO 10
<211> LENGTH: 15
<212> TYPE: DNA
<213> ORGANISM: Artificial Sequence
```

```
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<223> OTHER INFORMATION: Synthetic

<400> SEQUENCE: 10
accaagcnat caagt                                                         15

<210> SEQ ID NO 11
<211> LENGTH: 15
<212> TYPE: DNA
<213> ORGANISM: Artificial Sequence
<220> FEATURE:
<223> OTHER INFORMATION: Synthetic

<400> SEQUENCE: 11
accaagccat caagt                                                         15

<210> SEQ ID NO 12
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 5-methyl-pyrimidin-2-one, nonstandard
      nucleotide of the invention
<220> FEATURE:
<223> OTHER INFORMATION: Synthetic

<400> SEQUENCE: 12
accaagcnat caagt                                                         15

<210> SEQ ID NO 13
<211> LENGTH: 15
<212> TYPE: DNA
<213> ORGANISM: Artificial Sequence
<220> FEATURE:
<223> OTHER INFORMATION: Synthetic

<400> SEQUENCE: 13
acttgatagc ttggt                                                         15

<210> SEQ ID NO 14
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-aminopurine, nonstandard nucleotide of
      the invention
<220> FEATURE:
<223> OTHER INFORMATION: Synthetic

<400> SEQUENCE: 14
acttgatngc ttggt                                                         15

<210> SEQ ID NO 15
<211> LENGTH: 15
<212> TYPE: DNA
<213> ORGANISM: Artificial Sequence
<220> FEATURE:
<223> OTHER INFORMATION: Synthetic

<400> SEQUENCE: 15
```
acttgattgc ttggt                                                           15

<210> SEQ ID NO 16
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<223> OTHER INFORMATION: Synthetic

<400> SEQUENCE: 16
acttgatngc ttggt                                                           15

<210> SEQ ID NO 17
<211> LENGTH: 15
<212> TYPE: DNA
<213> ORGANISM: Artificial Sequence
<220> FEATURE:
<223> OTHER INFORMATION: Synthetic

<400> SEQUENCE: 17
acttgatggc ttggt                                                           15

<210> SEQ ID NO 18
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<223> OTHER INFORMATION: Synthetic

<400> SEQUENCE: 18
acttgatngc ttggt                                                           15

<210> SEQ ID NO 19
<211> LENGTH: 15
<212> TYPE: DNA
<213> ORGANISM: Artificial Sequence
<220> FEATURE:
<223> OTHER INFORMATION: Synthetic

<400> SEQUENCE: 19
acttgatcgc ttggt                                                           15

<210> SEQ ID NO 20
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 5-methyl-pyrimidin-2-one, nonstandard
      nucleotide of the invention
<220> FEATURE:
<223> OTHER INFORMATION: Synthetic

<400> SEQUENCE: 20
acttgatngc ttggt                                                           15

-continued

```
<210> SEQ ID NO 21
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2'-OMe hypoxanthine, nonstandard nucleotide
      of the invention
<220> FEATURE:
<223> OTHER INFORMATION: Synthetic

<400> SEQUENCE: 21
acttgatngc ttggt                                                     15

<210> SEQ ID NO 22
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2'-OMe 5-methyl-pyrimidin-2-one,
      nonstandard nucleotide of the invention
<220> FEATURE:
<223> OTHER INFORMATION: Synthetic

<400> SEQUENCE: 22
acttgatngc ttggt                                                     15

<210> SEQ ID NO 23
<211> LENGTH: 15
<212> TYPE: RNA
<213> ORGANISM: Artificial Sequence
<220> FEATURE:
<223> OTHER INFORMATION: Synthetic

<400> SEQUENCE: 23
accaagcaau caagu                                                     15

<210> SEQ ID NO 24
<211> LENGTH: 15
<212> TYPE: RNA
<213> ORGANISM: Artificial Sequence
<220> FEATURE:
<221> NAME/KEY: misc_feature
<222> LOCATION: (8)..(8)
<223> OTHER INFORMATION: n = 2-aminopurine, nonstandard nucleotide of
      the invention
<220> FEATURE:
<223> OTHER INFORMATION: Synthetic

<400> SEQUENCE: 24
accaagcnau caagu                                                     15

<210> SEQ ID NO 25
<211> LENGTH: 15
<212> TYPE: RNA
<213> ORGANISM: Artificial Sequence
<220> FEATURE:
<223> OTHER INFORMATION: Synthetic

<400> SEQUENCE: 25
accaagcuau caagu                                                     15

<210> SEQ ID NO 26
<211> LENGTH: 15
<212> TYPE: RNA
<213> ORGANISM: Artificial Sequence
```

```
<220> FEATURE:
<221> NAME/KEY: misc_feature
<222> LOCATION: (8)..(8)
<223> OTHER INFORMATION: n = 2'-deoxy-5-methyl-2-thiouridine,
      nonstandard nucleotide of the invention
<220> FEATURE:
<223> OTHER INFORMATION: Synthetic

<400> SEQUENCE: 26
accaagcnau caagu                                                   15

<210> SEQ ID NO 27
<211> LENGTH: 15
<212> TYPE: RNA
<213> ORGANISM: Artificial Sequence
<220> FEATURE:
<223> OTHER INFORMATION: Synthetic

<400> SEQUENCE: 27
accaagcgau caagu                                                   15

<210> SEQ ID NO 28
<211> LENGTH: 15
<212> TYPE: RNA
<213> ORGANISM: Artificial Sequence
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<223> OTHER INFORMATION: Synthetic

<400> SEQUENCE: 28
accaagcnau caagu                                                   15

<210> SEQ ID NO 29
<211> LENGTH: 15
<212> TYPE: RNA
<213> ORGANISM: Artificial Sequence
<220> FEATURE:
<223> OTHER INFORMATION: Synthetic

<400> SEQUENCE: 29
accaagccau caagu                                                   15

<210> SEQ ID NO 30
<211> LENGTH: 15
<212> TYPE: RNA
<213> ORGANISM: Artificial Sequence
<220> FEATURE:
<221> NAME/KEY: misc_feature
<222> LOCATION: (8)..(8)
<223> OTHER INFORMATION: n = 5-methyl-pyrimidin-2-one, nonstandard
      nucleotide of the invention
<220> FEATURE:
<223> OTHER INFORMATION: Synthetic

<400> SEQUENCE: 30
accaagcnau caagu                                                   15

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
```
tatctgcgtg ccctgtctct ggagg                                          25

<210> SEQ ID NO 32
<211> LENGTH: 25
<212> TYPE: DNA
<213> ORGANISM: Artificial Sequence
<220> FEATURE:
<223> OTHER INFORMATION: Synthetic

<400> SEQUENCE: 32
cctccagaga cagggcacgc agata                                          25

<210> SEQ ID NO 33
<211> LENGTH: 25
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = N4-ethylcytosine, nonstandard nucleotide of
      the invention
<220> FEATURE:
<221> NAME/KEY: misc_feature
<222> LOCATION: (2)..(2)
<223> OTHER INFORMATION: n = N4-ethylcytosine, nonstandard nucleotide of
      the invention
<220> FEATURE:
<221> NAME/KEY: misc_feature
<222> LOCATION: (3)..(3)
<223> OTHER INFORMATION: n = 2-aminopurine, nonstandard nucleotide of
      the invention
<220> FEATURE:
<221> NAME/KEY: misc_feature
<222> LOCATION: (4)..(4)
<223> OTHER INFORMATION: n = hypoxanthine, nonstandard nucleotide of the
      invention
<220> FEATURE:
<221> NAME/KEY: misc_feature
<222> LOCATION: (5)..(5)
<223> OTHER INFORMATION: n = hypoxanthine, nonstandard nucleotide of the
      invention
<220> FEATURE:
<221> NAME/KEY: misc_feature
<222> LOCATION: (6)..(6)
<223> OTHER INFORMATION: n = 2-aminopurine, nonstandard nucleotide of
      the invention
<220> FEATURE:
<221> NAME/KEY: misc_feature
<222> LOCATION: (7)..(7)
<223> OTHER INFORMATION: n = 2-thiothymine, nonstandard nucleotide of
      the invention
<220> FEATURE:
<221> NAME/KEY: misc_feature
<222> LOCATION: (8)..(8)
<223> OTHER INFORMATION: n = N4-ethylcytosine, nonstandard nucleotide of
      the invention
<220> FEATURE:
<221> NAME/KEY: misc_feature
<222> LOCATION: (9)..(9)
<223> OTHER INFORMATION: n = N4-ethylcytosine, nonstandard nucleotide of
      the invention
<220> FEATURE:
<221> NAME/KEY: misc_feature
<222> LOCATION: (10)..(10)
<223> OTHER INFORMATION: n = 2-aminopurine, nonstandard nucleotide of
      the invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of

```
      the invention
<220> FEATURE:
<221> NAME/KEY: misc_feature
<222> LOCATION: (13)..(13)
<223> OTHER INFORMATION: n = hypoxanthine, nonstandard nucleotide of the
      invention
<220> FEATURE:
<221> NAME/KEY: misc_feature
<222> LOCATION: (14)..(14)
<223> OTHER INFORMATION: n = 2-thiothymine, nonstandard nucleotide of
      the invention
<220> FEATURE:
<221> NAME/KEY: misc_feature
<222> LOCATION: (15)..(15)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = N4-ethylcytosine, nonstandard nucleotide of
      the invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = hypoxanthine, nonstandard nucleotide of the
      invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = hypoxanthine, nonstandard nucleotide of the
      invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 33
nnnnnnnnnn nnnnnnnnnn nnnng                                         25

<210> SEQ ID NO 34
<211> LENGTH: 25
<212> TYPE: DNA
<213> ORGANISM: Artificial Sequence
<220> FEATURE:
<223> OTHER INFORMATION: Synthetic

<400> SEQUENCE: 34
cagctcgtcg cacagtggat cctgg                                         25
```

<210> SEQ ID NO 35
<211> LENGTH: 25
<212> TYPE: DNA
<213> ORGANISM: Artificial Sequence
<220> FEATURE:
<223> OTHER INFORMATION: Synthetic

<400> SEQUENCE: 35
cgcacggtga tcgcagccgc tgtcc                                          25

<210> SEQ ID NO 36
<211> LENGTH: 25
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = hypoxanthine, nonstandard nucleotide of the
      invention
<220> FEATURE:
<221> NAME/KEY: misc_feature
<222> LOCATION: (2)..(2)
<223> OTHER INFORMATION: n = hypoxanthine, nonstandard nucleotide of the
      invention
<220> FEATURE:
<221> NAME/KEY: misc_feature
<222> LOCATION: (3)..(3)
<223> OTHER INFORMATION: n = 2-aminopurine, nonstandard nucleotide of
      the invention
<220> FEATURE:
<221> NAME/KEY: misc_feature
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = 2-aminopurine, nonstandard nucleotide of
      the invention
<220> FEATURE:
<221> NAME/KEY: misc_feature
<222> LOCATION: (6)..(6)
<223> OTHER INFORMATION: n = hypoxanthine, nonstandard nucleotide of the
      invention
<220> FEATURE:
<221> NAME/KEY: misc_feature
<222> LOCATION: (7)..(7)
<223> OTHER INFORMATION: n = N4-ethylcytosine, nonstandard nucleotide of
      the invention
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (9)..(9)
<223> OTHER INFORMATION: n = hypoxanthine, nonstandard nucleotide of the
      invention
<220> FEATURE:
<221> NAME/KEY: misc_feature
<222> LOCATION: (10)..(10)
<223> OTHER INFORMATION: n = N4-ethylcytosine, nonstandard nucleotide of
      the invention
<220> FEATURE:
<221> NAME/KEY: misc_feature
<222> LOCATION: (11)..(11)
<223> OTHER INFORMATION: n = 2-thiothymine, nonstandard nucleotide of
      the invention
<220> FEATURE:
<221> NAME/KEY: misc_feature
<222> LOCATION: (12)..(12)
<223> OTHER INFORMATION: n = hypoxanthine, nonstandard nucleotide of the
      invention
<220> FEATURE:

```
<221> NAME/KEY: misc_feature
<222> LOCATION: (13)..(13)
<223> OTHER INFORMATION: n = N4-ethylcytosine, nonstandard nucleotide of
      the invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<221> NAME/KEY: misc_feature
<222> LOCATION: (16)..(16)
<223> OTHER INFORMATION: n = 2-thiothymine, nonstandard nucleotide of
      the invention
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 36
nnnnnnnnnn nnnnnnnnnn nnnng                                            25

<210> SEQ ID NO 37
<211> LENGTH: 25
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: n = 2-aminopurine, nonstandard nucleotide of
      the invention
<220> FEATURE:
<221> NAME/KEY: misc_feature
<222> LOCATION: (6)..(6)
```

```
<223> OTHER INFORMATION: n = 2-aminopurine, nonstandard nucleotide of
      the invention
<220> FEATURE:
<221> NAME/KEY: misc_feature
<222> LOCATION: (7)..(7)
<223> OTHER INFORMATION: n = 2-thiothymine, nonstandard nucleotide of
      the invention
<220> FEATURE:
<221> NAME/KEY: misc_feature
<222> LOCATION: (10)..(10)
<223> OTHER INFORMATION: n = 2-aminopurine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of
      the invention
<220> FEATURE:
<221> NAME/KEY: misc_feature
<222> LOCATION: (14)..(14)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 37
ccnggnnccn cngngcgncg ngcng                                           25

<210> SEQ ID NO 38
<211> LENGTH: 25
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: n = 2-aminopurine, nonstandard nucleotide of
      the invention
<220> FEATURE:
<221> NAME/KEY: misc_feature
<222> LOCATION: (5)..(5)
<223> OTHER INFORMATION: n = 2-aminopurine, nonstandard nucleotide of
      the invention
<220> FEATURE:
<221> NAME/KEY: misc_feature
<222> LOCATION: (11)..(11)
<223> OTHER INFORMATION: n = 2-thiothymine, nonstandard nucleotide of
      the invention
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<221> NAME/KEY: misc_feature
<222> LOCATION: (16)..(16)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = 2-aminopurine, nonstandard nucleotide of
      the invention
```

<220> FEATURE:
<221> NAME/KEY: misc_feature
<222> LOCATION: (22)..(22)
<223> OTHER INFORMATION: n = 2-thiothymine, nonstandard nucleotide of
the invention
<220> FEATURE:
<223> OTHER INFORMATION: Synthetic

<400> SEQUENCE: 38
ggncngcggc ngcgnncncc gngcg                                    25

<210> SEQ ID NO 39
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
invention
<220> FEATURE:
<221> NAME/KEY: misc_feature
<222> LOCATION: (18)..(18)
<223> OTHER INFORMATION: n = 2-aminopurine, nonstandard nucleotide of
the invention
<220> FEATURE:
<221> NAME/KEY: misc_feature
<222> LOCATION: (19)..(19)
<223> OTHER INFORMATION: n = N4-ethylcytosine, nonstandard nucleotide of
the invention
<220> FEATURE:
<221> NAME/KEY: misc_feature
<222> LOCATION: (20)..(20)
<223> OTHER INFORMATION: n = hypoxanthine, nonstandard nucleotide of the
invention
<220> FEATURE:
<221> NAME/KEY: misc_feature
<222> LOCATION: (21)..(21)
<223> OTHER INFORMATION: n = 2-aminopurine, nonstandard nucleotide of
the invention
<220> FEATURE:
<221> NAME/KEY: misc_feature
<222> LOCATION: (22)..(22)
<223> OTHER INFORMATION: n = hypoxanthine, nonstandard nucleotide of the
invention
<220> FEATURE:
<221> NAME/KEY: misc_feature
<222> LOCATION: (23)..(23)
<223> OTHER INFORMATION: n = N4-ethylcytosine, nonstandard nucleotide of
the invention
<220> FEATURE:
<221> NAME/KEY: misc_feature
<222> LOCATION: (24)..(24)
<223> OTHER INFORMATION: n = 2-thiothymine, nonstandard nucleotide of
the invention
<220> FEATURE:
<223> OTHER INFORMATION: Synthetic

<400> SEQUENCE: 39
ccaggatcca ctgtgcnnnn nnnng                                    25

<210> SEQ ID NO 40
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
the invention
<220> FEATURE:
<221> NAME/KEY: misc_feature
<222> LOCATION: (18)..(18)
<223> OTHER INFORMATION: n = 2-aminopurine, nonstandard nucleotide of
the invention

```
<220> FEATURE:
<221> NAME/KEY: misc_feature
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 40
ggacagcggc tgcgatnnnn nnnng                                          25

<210> SEQ ID NO 41
<211> LENGTH: 25
<212> TYPE: DNA
<213> ORGANISM: Artificial Sequence
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = hypoxanthine, nonstandard nucleotide of the
      invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 41
ccaggatcca ctgtgcgacg nnnng                                          25

<210> SEQ ID NO 42
<211> LENGTH: 25
<212> TYPE: DNA
<213> ORGANISM: Artificial Sequence
<220> FEATURE:
<221> NAME/KEY: misc_feature
<222> LOCATION: (21)..(21)
<223> OTHER INFORMATION: n = hypoxanthine, nonstandard nucleotide of
      the invention
```

```
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 42
ggacagcggc tgcgatcacc nnnng                                          25

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
tgccctgtct ctggaggt                                                  18

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
acctccagag acagggca                                                  18

<210> SEQ ID NO 45
<211> LENGTH: 18
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-thiothymine, nonstandard nucleotide of
      the invention
<220> FEATURE:
<221> NAME/KEY: misc_feature
<222> LOCATION: (2)..(2)
<223> OTHER INFORMATION: n = hypoxanthine, nonstandard nucleotide of the
      invention
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
```

```
<223> OTHER INFORMATION: n = 2-thiothymine, nonstandard nucleotide of
      the invention
<220> FEATURE:
<221> NAME/KEY: misc_feature
<222> LOCATION: (7)..(7)
<223> OTHER INFORMATION: n = hypoxanthine, nonstandard nucleotide of the
      invention
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<221> NAME/KEY: misc_feature
<222> LOCATION: (9)..(9)
<223> OTHER INFORMATION: n = N4-ethylcytosine, nonstandard nucleotide of
      the invention
<220> FEATURE:
<221> NAME/KEY: misc_feature
<222> LOCATION: (10)..(10)
<223> OTHER INFORMATION: n = 2-thiothymine, nonstandard nucleotide of
      the invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<221> NAME/KEY: misc_feature
<222> LOCATION: (12)..(12)
<223> OTHER INFORMATION: n = hypoxanthine, nonstandard nucleotide of the
      invention
<220> FEATURE:
<221> NAME/KEY: misc_feature
<222> LOCATION: (13)..(13)
<223> OTHER INFORMATION: n = hypoxanthine, nonstandard nucleotide of the
      invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<223> OTHER INFORMATION: Synthetic

<400> SEQUENCE: 45 nnnnnnnnn nnnnnnnt                                                        18

<210> SEQ ID NO 46
<211> LENGTH: 18
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-aminopurine, nonstandard nucleotide of
      the invention
<220> FEATURE:
<221> NAME/KEY: misc_feature
<222> LOCATION: (2)..(2)
<223> OTHER INFORMATION: n = N4-ethylcytosine, nonstandard nucleotide of
      the invention
```

```
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (4)..(4)
<223> OTHER INFORMATION: n = 2-thiothymine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
<223> OTHER INFORMATION: n = N4-ethylcytosine, nonstandard nucleotide of
      the invention
<220> FEATURE:
<221> NAME/KEY: misc_feature
<222> LOCATION: (7)..(7)
<223> OTHER INFORMATION: n = 2-aminopurine, nonstandard nucleotide of
      the invention
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (9)..(9)
<223> OTHER INFORMATION: n = 2-aminopurine, nonstandard nucleotide of
      the invention
<220> FEATURE:
<221> NAME/KEY: misc_feature
<222> LOCATION: (10)..(10)
<223> OTHER INFORMATION: n = hypoxanthine, nonstandard nucleotide of the
      invention
<220> FEATURE:
<221> NAME/KEY: misc_feature
<222> LOCATION: (11)..(11)
<223> OTHER INFORMATION: n = 2-aminopurine, nonstandard nucleotide of
      the invention
<220> FEATURE:
<221> NAME/KEY: misc_feature
<222> LOCATION: (12)..(12)
<223> OTHER INFORMATION: n = N4-ethylcytosine, nonstandard nucleotide of
      the invention
<220> FEATURE:
<221> NAME/KEY: misc_feature
<222> LOCATION: (13)..(13)
<223> OTHER INFORMATION: n = 2-aminopurine, nonstandard nucleotide of
      the invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (15)..(15)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<223> OTHER INFORMATION: Synthetic

<400> SEQUENCE: 46
```
nnnnnnnnnn nnnnnnna                            18

<210> SEQ ID NO 47
<211> LENGTH: 25
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-thiothymine, nonstandard nucleotide of
      the invention
<220> FEATURE:
<221> NAME/KEY: misc_feature
<222> LOCATION: (2)..(2)
<223> OTHER INFORMATION: n = 2-aminopurine, nonstandard nucleotide of
      the invention
<220> FEATURE:
<221> NAME/KEY: misc_feature
<222> LOCATION: (3)..(3)
<223> OTHER INFORMATION: n = 2-thiothymine, nonstandard nucleotide of
      the invention
<220> FEATURE:
<221> NAME/KEY: misc_feature
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = 2-thiothymine, nonstandard nucleotide of
      the invention
<220> FEATURE:
<221> NAME/KEY: misc_feature
<222> LOCATION: (6)..(6)
<223> OTHER INFORMATION: n = hypoxanthine, nonstandard nucleotide of the
      invention
<220> FEATURE:
<221> NAME/KEY: misc_feature
<222> LOCATION: (7)..(7)
<223> OTHER INFORMATION: n = N4-ethylcytosine, nonstandard nucleotide of
      the invention
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (9)..(9)
<223> OTHER INFORMATION: n = 2-thiothymine, nonstandard nucleotide of
      the invention
<220> FEATURE:
<221> NAME/KEY: misc_feature
<222> LOCATION: (10)..(10)
<223> OTHER INFORMATION: n = hypoxanthine, nonstandard nucleotide of the
      invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<221> NAME/KEY: misc_feature
<222> LOCATION: (12)..(12)
<223> OTHER INFORMATION: n = N4-ethylcytosine, nonstandard nucleotide of
      the invention
<220> FEATURE:
<221> NAME/KEY: misc_feature
<222> LOCATION: (13)..(13)
<223> OTHER INFORMATION: n = N4-ethylcytosine, nonstandard nucleotide of
      the invention
<220> FEATURE:
<221> NAME/KEY: misc_feature
<222> LOCATION: (14)..(14)
<223> OTHER INFORMATION: n = 2-thiothymine, nonstandard nucleotide of
      the invention
<220> FEATURE:

<221> NAME/KEY: misc_feature
<222> LOCATION: (15)..(15)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = 2-thiothymine, nonstandard nucleotide of
      the invention
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = hypoxanthine, nonstandard nucleotide of the
      invention
<220> FEATURE:
<221> NAME/KEY: misc_feature
<222> LOCATION: (23)..(23)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = hypoxanthine, nonstandard nucleotide of the
      invention
<220> FEATURE:
<223> OTHER INFORMATION: Synthetic

<400> SEQUENCE: 47
nnnnnnnnnn nnnnnnnnnn nnnng                                          25

<210> SEQ ID NO 48
<211> LENGTH: 25
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: nonstandard nucleotide of the invention
<220> FEATURE:
<221> NAME/KEY: misc_feature
<222> LOCATION: (2)..(2)
<223> OTHER INFORMATION: nonstandard nucleotide of the invention
<220> FEATURE:
<221> NAME/KEY: misc_feature
<222> LOCATION: (3)..(3)
<223> OTHER INFORMATION: nonstandard nucleotide of the invention
<220> FEATURE:
<221> NAME/KEY: misc_feature
<222> LOCATION: (4)..(4)
<223> OTHER INFORMATION: nonstandard nucleotide of the invention
<220> FEATURE:
<221> NAME/KEY: misc_feature

```
<222> LOCATION: (5)..(5)
<223> OTHER INFORMATION: nonstandard nucleotide of the invention
<220> FEATURE:
<221> NAME/KEY: misc_feature
<222> LOCATION: (6)..(6)
<223> OTHER INFORMATION: nonstandard nucleotide of the invention
<220> FEATURE:
<221> NAME/KEY: misc_feature
<222> LOCATION: (7)..(7)
<223> OTHER INFORMATION: nonstandard nucleotide of the invention
<220> FEATURE:
<221> NAME/KEY: misc_feature
<222> LOCATION: (8)..(8)
<223> OTHER INFORMATION: nonstandard nucleotide of the invention
<220> FEATURE:
<221> NAME/KEY: misc_feature
<222> LOCATION: (9)..(9)
<223> OTHER INFORMATION: nonstandard nucleotide of the invention
<220> FEATURE:
<221> NAME/KEY: misc_feature
<222> LOCATION: (10)..(10)
<223> OTHER INFORMATION: nonstandard nucleotide of the invention
<220> FEATURE:
<221> NAME/KEY: misc_feature
<222> LOCATION: (11)..(11)
<223> OTHER INFORMATION: nonstandard nucleotide of the invention
<220> FEATURE:
<221> NAME/KEY: misc_feature
<222> LOCATION: (12)..(12)
<223> OTHER INFORMATION: nonstandard nucleotide of the invention
<220> FEATURE:
<221> NAME/KEY: misc_feature
<222> LOCATION: (13)..(13)
<223> OTHER INFORMATION: nonstandard nucleotide of the invention
<220> FEATURE:
<221> NAME/KEY: misc_feature
<222> LOCATION: (14)..(14)
<223> OTHER INFORMATION: nonstandard nucleotide of the invention
<220> FEATURE:
<221> NAME/KEY: misc_feature
<222> LOCATION: (15)..(15)
<223> OTHER INFORMATION: nonstandard nucleotide of the invention
<220> FEATURE:
<221> NAME/KEY: misc_feature
<222> LOCATION: (16)..(16)
<223> OTHER INFORMATION: nonstandard nucleotide of the invention
<220> FEATURE:
<221> NAME/KEY: misc_feature
<222> LOCATION: (17)..(17)
<223> OTHER INFORMATION: nonstandard nucleotide of the invention
<220> FEATURE:
<221> NAME/KEY: misc_feature
<222> LOCATION: (18)..(18)
<223> OTHER INFORMATION: nonstandard nucleotide of the invention
<220> FEATURE:
<221> NAME/KEY: misc_feature
<222> LOCATION: (19)..(19)
<223> OTHER INFORMATION: nonstandard nucleotide of the invention
<220> FEATURE:
<221> NAME/KEY: misc_feature
<222> LOCATION: (20)..(20)
<223> OTHER INFORMATION: nonstandard nucleotide of the invention
<220> FEATURE:
<221> NAME/KEY: misc_feature
<222> LOCATION: (21)..(21)
<223> OTHER INFORMATION: nonstandard nucleotide of the invention
<220> FEATURE:
<221> NAME/KEY: misc_feature
<222> LOCATION: (22)..(22)
<223> OTHER INFORMATION: nonstandard nucleotide of the invention
<220> FEATURE:
<221> NAME/KEY: misc_feature
<222> LOCATION: (23)..(23)
<223> OTHER INFORMATION: nonstandard nucleotide of the invention
<220> FEATURE:
<221> NAME/KEY: misc_feature
<222> LOCATION: (24)..(24)
<223> OTHER INFORMATION: nonstandard nucleotide of the invention
<220> FEATURE:
```

-continued

<223> OTHER INFORMATION: Synthetic

<400> SEQUENCE: 48 nnnnnnnnn nnnnnnnnn nnnna                                      25

<210> SEQ ID NO 49
<211> LENGTH: 18
<212> TYPE: DNA
<213> ORGANISM: Artificial Sequence
<220> FEATURE:
<223> OTHER INFORMATION: Synthetic

<400> SEQUENCE: 49
tattttattt ttaaaaat                                            18

<210> SEQ ID NO 50
<211> LENGTH: 18
<212> TYPE: DNA
<213> ORGANISM: Artificial Sequence
<220> FEATURE:
<223> OTHER INFORMATION: Synthetic

<400> SEQUENCE: 50
ataaaataaa aattttta                                            18

<210> SEQ ID NO 51
<211> LENGTH: 18
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: n = 5-methypyrimid-2-one, nonstandard
      nucleotide of the invention
<220> FEATURE:
<221> NAME/KEY: misc_feature
<222> LOCATION: (4)..(4)
<223> OTHER INFORMATION: n = 5-methypyrimid-2-one, nonstandard
      nucleotide of the invention
<220> FEATURE:
<221> NAME/KEY: misc_feature
<222> LOCATION: (5)..(5)
<223> OTHER INFORMATION: n = 5-methypyrimid-2-one, nonstandard
      nucleotide of the invention
<220> FEATURE:
<221> NAME/KEY: misc_feature
<222> LOCATION: (9)..(9)
<223> OTHER INFORMATION: n = 5-methypyrimid-2-one, nonstandard
      nucleotide of the invention
<220> FEATURE:
<221> NAME/KEY: misc_feature
<222> LOCATION: (11)..(11)
<223> OTHER INFORMATION: n = 5-methypyrimid-2-one, nonstandard
      nucleotide of the invention
<220> FEATURE:
<223> OTHER INFORMATION: Synthetic

<400> SEQUENCE: 51
tgnnntgtnt ntggaggt                                            18

<210> SEQ ID NO 52
<211> LENGTH: 18
<212> TYPE: DNA
<213> ORGANISM: Artificial Sequence
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature

```
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (9)..(9)
<223> OTHER INFORMATION: n = N4-ethylcytosine, nonstandard nucleotide of
      the invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<223> OTHER INFORMATION: Synthetic

<400> SEQUENCE: 52
tgnnntgtnt ntggaggt                                                 18

<210> SEQ ID NO 53
<211> LENGTH: 18
<212> TYPE: DNA
<213> ORGANISM: Artificial Sequence
<220> FEATURE:
<223> OTHER INFORMATION: Synthetic

<400> SEQUENCE: 53
acctccagag acagggca                                                 18

<210> SEQ ID NO 54
<211> LENGTH: 18
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (10)..(10)
<223> OTHER INFORMATION: n = hypoxanthine, nonstandard nucleotide of the
      invention
<220> FEATURE:
<223> OTHER INFORMATION: Synthetic

<400> SEQUENCE: 54
acctccanan cacgggca                                                 18

<210> SEQ ID NO 55
<211> LENGTH: 18
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (10)..(10)
<223> OTHER INFORMATION: n = hypoxanthine, nonstandard nucleotide of the
      invention
<220> FEATURE:
<221> NAME/KEY: misc_feature
<222> LOCATION: (14)..(14)
<223> OTHER INFORMATION: n = hypoxanthine, nonstandard nucleotide of the
      invention
```

```
<220> FEATURE:
<221> NAME/KEY: misc_feature
<222> LOCATION: (15)..(15)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<223> OTHER INFORMATION: Synthetic

<400> SEQUENCE: 55
acctccanan acannnca                                                       18

<210> SEQ ID NO 56
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<223> OTHER INFORMATION: Synthetic

<400> SEQUENCE: 56
tggttcgnta gttca                                                          15

<210> SEQ ID NO 57
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 5-methyl-pyrimidin-2-one, nonstandard
      nucleotide of the invention
<220> FEATURE:
<223> OTHER INFORMATION: Synthetic

<400> SEQUENCE: 57
tggttcgnta gttca                                                          15

<210> SEQ ID NO 58
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-aminopurine, nonstandard nucleotide of
      the invention
<220> FEATURE:
<223> OTHER INFORMATION: Synthetic

<400> SEQUENCE: 58
tggttcgnta gttca                                                          15

<210> SEQ ID NO 59
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
```

```
<223> OTHER INFORMATION: Synthetic

<400> SEQUENCE: 59
tggttcgnta gttca                                                      15

<210> SEQ ID NO 60
<211> LENGTH: 38
<212> TYPE: DNA
<213> ORGANISM: Artificial Sequence
<220> FEATURE:
<223> OTHER INFORMATION: Synthetic

<400> SEQUENCE: 60
gacgcgcgat ttcttcagca acctccagag acagggca                             38

<210> SEQ ID NO 61
<211> LENGTH: 38
<212> TYPE: DNA
<213> ORGANISM: Artificial Sequence
<220> FEATURE:
<223> OTHER INFORMATION: Synthetic

<400> SEQUENCE: 61
ctggatgttg catatctgcg tgccctgtct ctggaggt                             38

<210> SEQ ID NO 62
<211> LENGTH: 18
<212> TYPE: DNA
<213> ORGANISM: Artificial Sequence
<220> FEATURE:
<223> OTHER INFORMATION: Synthetic

<400> SEQUENCE: 62
gacgcgcgat ttcttcag                                                   18

<210> SEQ ID NO 63
<211> LENGTH: 18
<212> TYPE: DNA
<213> ORGANISM: Artificial Sequence
<220> FEATURE:
<223> OTHER INFORMATION: Synthetic

<400> SEQUENCE: 63
ctggatgttg catatctg                                                   18

<210> SEQ ID NO 64
<211> LENGTH: 18
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-aminopurine, nonstandard nucleotide of
      the invention
<220> FEATURE:
<221> NAME/KEY: misc_feature
<222> LOCATION: (7)..(7)
<223> OTHER INFORMATION: n = 2-aminopurine, nonstandard nucleotide of
      the invention
<220> FEATURE:
<221> NAME/KEY: misc_feature
<222> LOCATION: (9)..(9)
<223> OTHER INFORMATION: n = 2-aminopurine, nonstandard nucleotide of
      the invention
<220> FEATURE:
<221> NAME/KEY: misc_feature
<222> LOCATION: (11)..(11)
<223> OTHER INFORMATION: n = 2-aminopurine, nonstandard nucleotide of
      the invention
```

```
<220> FEATURE:
<221> NAME/KEY: misc_feature
<222> LOCATION: (13)..(13)
<223> OTHER INFORMATION: n = 2-aminopurine, nonstandard nucleotide of
      the invention
<220> FEATURE:
<223> OTHER INFORMATION: Synthetic

<400> SEQUENCE: 64
ncctccngng ncngggca                                                 18

<210> SEQ ID NO 65
<211> LENGTH: 18
<212> TYPE: DNA
<213> ORGANISM: Artificial Sequence
<220> FEATURE:
<221> NAME/KEY: misc_feature
<222> LOCATION: (4)..(4)
<223> OTHER INFORMATION: n = 2-thiothymine, nonstandard nucleotide of
      the invention
<220> FEATURE:
<223> OTHER INFORMATION: Synthetic

<400> SEQUENCE: 65
accnccagag acagggca                                                 18

<210> SEQ ID NO 66
<211> LENGTH: 18
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: n = N4-ethylcytosine, nonstandard nucleotide of
      the invention
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
<223> OTHER INFORMATION: n = N4-ethylcytosine, nonstandard nucleotide of
      the invention
<220> FEATURE:
<221> NAME/KEY: misc_feature
<222> LOCATION: (12)..(12)
<223> OTHER INFORMATION: n = N4-ethylcytosine, nonstandard nucleotide of
      the invention
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<223> OTHER INFORMATION: Synthetic

<400> SEQUENCE: 66
anntnnagag anagggna                                                 18

<210> SEQ ID NO 67
<211> LENGTH: 18
<212> TYPE: DNA
<213> ORGANISM: Artificial Sequence
<220> FEATURE:
<221> NAME/KEY: misc_feature
<222> LOCATION: (2)..(2)
```

```
<223> OTHER INFORMATION: n = N4-ethylcytosine, nonstandard nucleotide of
      the invention
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
<223> OTHER INFORMATION: n = N4-ethylcytosine, nonstandard nucleotide of
      the invention
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (10)..(10)
<223> OTHER INFORMATION: n = hypoxanthine, nonstandard nucleotide of the
      invention
<220> FEATURE:
<221> NAME/KEY: misc_feature
<222> LOCATION: (12)..(12)
<223> OTHER INFORMATION: n = N4-ethylcytosine, nonstandard nucleotide of
      the invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (15)..(15)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<223> OTHER INFORMATION: Synthetic

<400> SEQUENCE: 67
anntnnanan anannnna                                                  18

<210> SEQ ID NO 68
<211> LENGTH: 18
<212> TYPE: DNA
<213> ORGANISM: Artificial Sequence
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<223> OTHER INFORMATION: Synthetic

<400> SEQUENCE: 68
tgccctgtct ctggnggt                                                  18

<210> SEQ ID NO 69
<211> LENGTH: 18
```

```
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-thiothymine, nonstandard nucleotide of
      the invention
<220> FEATURE:
<221> NAME/KEY: misc_feature
<222> LOCATION: (6)..(6)
<223> OTHER INFORMATION: n = 2-thiothymine, nonstandard nucleotide of
      the invention
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<221> NAME/KEY: misc_feature
<222> LOCATION: (10)..(10)
<223> OTHER INFORMATION: n = 2-thiothymine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of
      the invention
<220> FEATURE:
<223> OTHER INFORMATION: Synthetic

<400> SEQUENCE: 69
ngcccngncn cnggaggt                                                   18

<210> SEQ ID NO 70
<211> LENGTH: 18
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: n = hypoxanthine, nonstandard nucleotide of the
      invention
<220> FEATURE:
<221> NAME/KEY: misc_feature
<222> LOCATION: (7)..(7)
<223> OTHER INFORMATION: n = hypoxanthine, nonstandard nucleotide of the
      invention
<220> FEATURE:
<221> NAME/KEY: misc_feature
<222> LOCATION: (13)..(13)
<223> OTHER INFORMATION: n = hypoxanthine, nonstandard nucleotide of the
      invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<223> OTHER INFORMATION: Synthetic

<400> SEQUENCE: 70
tnccctntct ctnnannt                                                   18

<210> SEQ ID NO 71
<211> LENGTH: 18
```

```
<212> TYPE: DNA
<213> ORGANISM: Artificial Sequence
<220> FEATURE:
<221> NAME/KEY: misc_feature
<222> LOCATION: (2)..(2)
<223> OTHER INFORMATION: n = hypoxanthine, nonstandard nucleotide of the
      invention
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (7)..(7)
<223> OTHER INFORMATION: n = hypoxanthine, nonstandard nucleotide of the
      invention
<220> FEATURE:
<221> NAME/KEY: misc_feature
<222> LOCATION: (9)..(9)
<223> OTHER INFORMATION: n = N4-ethylcytosine, nonstandard nucleotide of
      the invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<221> NAME/KEY: misc_feature
<222> LOCATION: (13)..(13)
<223> OTHER INFORMATION: n = hypoxanthine, nonstandard nucleotide of the
      invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<223> OTHER INFORMATION: Synthetic

<400> SEQUENCE: 71
tnnnntntnt ntnnannt                                                   18

<210> SEQ ID NO 72
<211> LENGTH: 18
<212> TYPE: DNA
<213> ORGANISM: Artificial Sequence
<220> FEATURE:
<223> OTHER INFORMATION: Synthetic

<400> SEQUENCE: 72
tgccctgtct ctggaggt                                                   18

<210> SEQ ID NO 73
<211> LENGTH: 38
```

```
<212> TYPE: DNA
<213> ORGANISM: Artificial Sequence
<220> FEATURE:
<223> OTHER INFORMATION: Synthetic

<400> SEQUENCE: 73
gacgcgcgat ttcttcagac acctccagag acagggca                          38

<210> SEQ ID NO 74
<211> LENGTH: 15
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-thiothymine, nonstandard nucleotide of
      the invention
<220> FEATURE:
<221> NAME/KEY: misc_feature
<222> LOCATION: (2)..(2)
<223> OTHER INFORMATION: n = hypoxanthine, nonstandard nucleotide of the
      invention
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
<223> OTHER INFORMATION: n = 2-thiothymine, nonstandard nucleotide of
      the invention
<220> FEATURE:
<221> NAME/KEY: misc_feature
<222> LOCATION: (7)..(7)
<223> OTHER INFORMATION: n = hypoxanthine, nonstandard nucleotide of the
      invention
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<221> NAME/KEY: misc_feature
<222> LOCATION: (9)..(9)
<223> OTHER INFORMATION: n = N4-ethylcytosine, nonstandard nucleotide of
      the invention
<220> FEATURE:
<221> NAME/KEY: misc_feature
<222> LOCATION: (10)..(10)
<223> OTHER INFORMATION: n = 2-thiothymine, nonstandard nucleotide of
      the invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of
      the invention
<220> FEATURE:
<221> NAME/KEY: misc_feature
<222> LOCATION: (13)..(13)
<223> OTHER INFORMATION: n = hypoxanthine, nonstandard nucleotide of the
      invention
```

```
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<223> OTHER INFORMATION: Synthetic

<400> SEQUENCE: 74
nnnnnnnnnn nnnna                                                            15

<210> SEQ ID NO 75
<211> LENGTH: 20
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-thiothymine, nonstandard nucleotide of
      the invention
<220> FEATURE:
<221> NAME/KEY: misc_feature
<222> LOCATION: (2)..(2)
<223> OTHER INFORMATION: n = hypoxanthine, nonstandard nucleotide of the
      invention
<220> FEATURE:
<221> NAME/KEY: misc_feature
<222> LOCATION: (3)..(3)
<223> OTHER INFORMATION: n = N4-ethylcytosine, nonstandard nucleotide of
      the invention
<220> FEATURE:
<221> NAME/KEY: misc_feature
<222> LOCATION: (4)..(4)
<223> OTHER INFORMATION: n = N4-ethylcytosine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
<223> OTHER INFORMATION: n = 2-thiothymine, nonstandard nucleotide of
      the invention
<220> FEATURE:
<221> NAME/KEY: misc_feature
<222> LOCATION: (7)..(7)
<223> OTHER INFORMATION: n = hypoxanthine, nonstandard nucleotide of the
      invention
<220> FEATURE:
<221> NAME/KEY: misc_feature
<222> LOCATION: (8)..(8)
<223> OTHER INFORMATION: n = 2-thiothymine, nonstandard nucleotide of
      the invention
<220> FEATURE:
<221> NAME/KEY: misc_feature
<222> LOCATION: (9)..(9)
<223> OTHER INFORMATION: n = N4-ethylcytosine, nonstandard nucleotide of
      the invention
<220> FEATURE:
<221> NAME/KEY: misc_feature
<222> LOCATION: (10)..(10)
<223> OTHER INFORMATION: n = 2-thiothymine, nonstandard nucleotide of
      the invention
<220> FEATURE:
<221> NAME/KEY: misc_feature
<222> LOCATION: (11)..(11)
<223> OTHER INFORMATION: n = N4-ethylcytosine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of
      the invention
<220> FEATURE:
<221> NAME/KEY: misc_feature
```

```
<222> LOCATION: (13)..(13)
<223> OTHER INFORMATION: n = hypoxanthine, nonstandard nucleotide of the
      invention
<220> FEATURE:
<221> NAME/KEY: misc_feature
<222> LOCATION: (14)..(14)
<223> OTHER INFORMATION: n = hypoxanthine, nonstandard nucleotide of the
      invention
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<221> NAME/KEY: misc_feature
<222> LOCATION: (16)..(16)
<223> OTHER INFORMATION: n = hypoxanthine, nonstandard nucleotide of the
      invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<223> OTHER INFORMATION: Synthetic

<400> SEQUENCE: 75
nnnnnnnnnn nnnnnnnng                                                   20

<210> SEQ ID NO 76
<211> LENGTH: 38
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-aminopurine, nonstandard nucleotide of
      the invention
<220> FEATURE:
<221> NAME/KEY: misc_feature
<222> LOCATION: (2)..(2)
<223> OTHER INFORMATION: n = N4-ethylcytosine, nonstandard nucleotide of
      the invention
<220> FEATURE:
<221> NAME/KEY: misc_feature
<222> LOCATION: (3)..(3)
<223> OTHER INFORMATION: n = hypoxanthine, nonstandard nucleotide of the
      invention
<220> FEATURE:
<221> NAME/KEY: misc_feature
<222> LOCATION: (4)..(4)
<223> OTHER INFORMATION: n = 2-aminopurine, nonstandard nucleotide of
      the invention
<220> FEATURE:
<221> NAME/KEY: misc_feature
<222> LOCATION: (5)..(5)
<223> OTHER INFORMATION: n = N4-ethylcytosine, nonstandard nucleotide of
      the invention
<220> FEATURE:
<221> NAME/KEY: misc_feature
<222> LOCATION: (6)..(6)
<223> OTHER INFORMATION: n = 2-thiothymine, nonstandard nucleotide of
      the invention
<220> FEATURE:
<221> NAME/KEY: misc_feature
<222> LOCATION: (7)..(7)
<223> OTHER INFORMATION: n = hypoxanthine, nonstandard nucleotide of the
```

```
      invention
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (9)..(9)
<223> OTHER INFORMATION: n = hypoxanthine, nonstandard nucleotide of the
      invention
<220> FEATURE:
<221> NAME/KEY: misc_feature
<222> LOCATION: (10)..(10)
<223> OTHER INFORMATION: n = 2-thiothymine, nonstandard nucleotide of
      the invention
<220> FEATURE:
<221> NAME/KEY: misc_feature
<222> LOCATION: (11)..(11)
<223> OTHER INFORMATION: n = 2-thiothymine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of
      the invention
<220> FEATURE:
<221> NAME/KEY: misc_feature
<222> LOCATION: (13)..(13)
<223> OTHER INFORMATION: n = N4-ethylcytosine, nonstandard nucleotide of
      the invention
<220> FEATURE:
<221> NAME/KEY: misc_feature
<222> LOCATION: (14)..(14)
<223> OTHER INFORMATION: n = N4-ethylcytosine, nonstandard nucleotide of
      the invention
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<221> NAME/KEY: misc_feature
<222> LOCATION: (16)..(16)
<223> OTHER INFORMATION: n = 2-aminopurine, nonstandard nucleotide of
      the invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = hypoxanthine, nonstandard nucleotide of the
      invention
<220> FEATURE:
<223> OTHER INFORMATION: Synthetic

<400> SEQUENCE: 76
nnnnnnnnnn nnnnnnnngg ctgaagaaat cgcgcgtc                                 38

<210> SEQ ID NO 77
<211> LENGTH: 38
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = 2-aminopurine, nonstandard nucleotide of
      the invention
<220> FEATURE:
<221> NAME/KEY: misc_feature
<222> LOCATION: (2)..(2)
<223> OTHER INFORMATION: n = 5-methyl-pyrimidin-2-one, nonstandard
      nucleotide of the invention
<220> FEATURE:
```

```
<221> NAME/KEY: misc_feature
<222> LOCATION: (3)..(3)
<223> OTHER INFORMATION: n = hypoxanthine, nonstandard nucleotide of the
      invention
<220> FEATURE:
<221> NAME/KEY: misc_feature
<222> LOCATION: (4)..(4)
<223> OTHER INFORMATION: n = 2-aminopurine, nonstandard nucleotide of
      the invention
<220> FEATURE:
<221> NAME/KEY: misc_feature
<222> LOCATION: (5)..(5)
<223> OTHER INFORMATION: n = 5-methyl-pyrimidin-2-one, nonstandard
      nucleotide of the invention
<220> FEATURE:
<221> NAME/KEY: misc_feature
<222> LOCATION: (6)..(6)
<223> OTHER INFORMATION: n = 2-thiothymine, nonstandard nucleotide of
      the invention
<220> FEATURE:
<221> NAME/KEY: misc_feature
<222> LOCATION: (7)..(7)
<223> OTHER INFORMATION: n = hypoxanthine, nonstandard nucleotide of the
      invention
<220> FEATURE:
<221> NAME/KEY: misc_feature
<222> LOCATION: (8)..(8)
<223> OTHER INFORMATION: n = hypoxanthine, nonstandard nucleotide of the
      invention
<220> FEATURE:
<221> NAME/KEY: misc_feature
<222> LOCATION: (9)..(9)
<223> OTHER INFORMATION: n = hypoxanthine, nonstandard nucleotide of the
      invention
<220> FEATURE:
<221> NAME/KEY: misc_feature
<222> LOCATION: (10)..(10)
<223> OTHER INFORMATION: n = 2-thiothymine, nonstandard nucleotide of
      the invention
<220> FEATURE:
<221> NAME/KEY: misc_feature
<222> LOCATION: (11)..(11)
<223> OTHER INFORMATION: n = 2-thiothymine, nonstandard nucleotide of
      the invention
<220> FEATURE:
<221> NAME/KEY: misc_feature
<222> LOCATION: (12)..(12)
<223> OTHER INFORMATION: n = 2-thiothymine, nonstandard nucleotide of
      the invention
<220> FEATURE:
<221> NAME/KEY: misc_feature
<222> LOCATION: (13)..(13)
<223> OTHER INFORMATION: n = 5-methyl-pyrimidin-2-one, nonstandard
      nucleotide of the invention
<220> FEATURE:
<221> NAME/KEY: misc_feature
<222> LOCATION: (14)..(14)
<223> OTHER INFORMATION: n = 5-methyl-pyrimidin-2-one, nonstandard
      nucleotide of the invention
<220> FEATURE:
<221> NAME/KEY: misc_feature
<222> LOCATION: (15)..(15)
<223> OTHER INFORMATION: n = 2-aminopurine, nonstandard nucleotide of
      the invention
<220> FEATURE:
<221> NAME/KEY: misc_feature
<222> LOCATION: (16)..(16)
<223> OTHER INFORMATION: n = 2-aminopurine, nonstandard nucleotide of
      the invention
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = hypoxanthine, nonstandard nucleotide of the
      invention
```

```
<220> FEATURE:
<223> OTHER INFORMATION: Synthetic

<400> SEQUENCE: 77
nnnnnnnnnn nnnnnnnngg ctgaagaaat cgcgcgtc                            38

<210> SEQ ID NO 78
<211> LENGTH: 22
<212> TYPE: DNA
<213> ORGANISM: Artificial Sequence
<220> FEATURE:
<223> OTHER INFORMATION: Synthetic

<400> SEQUENCE: 78
gacgcgcgat ttcttcagcc cc                                            22

<210> SEQ ID NO 79
<211> LENGTH: 26
<212> TYPE: DNA
<213> ORGANISM: Artificial Sequence
<220> FEATURE:
<223> OTHER INFORMATION: Synthetic

<400> SEQUENCE: 79
gacgcgcgat ttcttcagcc ccttgg                                        26

<210> SEQ ID NO 80
<211> LENGTH: 32
<212> TYPE: DNA
<213> ORGANISM: Artificial Sequence
<220> FEATURE:
<223> OTHER INFORMATION: Synthetic

<400> SEQUENCE: 80
gacgcgcgat ttcttcagcc ccttggaaac cc                                 32

<210> SEQ ID NO 81
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
```

```
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = hypoxanthine, nonstandard nucleotide of the
      invention
<220> FEATURE:
<223> OTHER INFORMATION: Synthetic

<400> SEQUENCE: 81
ttagggtcgg attccannnn nnnng                                              25

<210> SEQ ID NO 82
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = N4-ethylcytosine, nonstandard nucleotide of
      the invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 82
atgatcaaaa agggatnnnn nnnnc                                              25

<210> SEQ ID NO 83
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
      the invention
<220> FEATURE:
```

```
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 83
cgggaaagtg gtgaagnnnn nnnnc                                           25

<210> SEQ ID NO 84
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = hypoxanthine, nonstandard nucleotide of the
      invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
```

<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 84
ccctgacaac atagttnnnn nnnnt                                          25

<210> SEQ ID NO 85
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = N4-ethylcytosine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 85
agatttgtga ttttggnnnn nnnng                                          25

<210> SEQ ID NO 86
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)

-continued

```
<223> OTHER INFORMATION: n = hypoxanthine, nonstandard nucleotide of the
      invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 86
tgtcaagcag agaatgnnnn nnnnc                                          25

<210> SEQ ID NO 87
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = hypoxanthine, nonstandard nucleotide of the
      invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = 2-aminopurine, nonstandard nucleotide of
      the invention
```

```
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 87
ccgcagtaca acccagnnnn nnnng                                        25

<210> SEQ ID NO 88
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = hypoxanthine, nonstandard nucleotide of the
      invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 88
atgagaggct tgttcannnn nnnng                                        25

<210> SEQ ID NO 89
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = hypoxanthine, nonstandard nucleotide of the
      invention
```

```
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 89
gctcgcaacg tcctccnnnn nnnng                                             25

<210> SEQ ID NO 90
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
```

```
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 90
attaaagtga aggaggnnnn nnnng                                            25

<210> SEQ ID NO 91
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 91
cacagcaggg tcttctnnnn nnnng                                            25

<210> SEQ ID NO 92
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
```

```
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 92
ctccttctgc atggtannnn nnnnc                                          25

<210> SEQ ID NO 93
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
``` the invention
<220> FEATURE:
<223> OTHER INFORMATION: Synthetic

<400> SEQUENCE: 93
ctgaaagtag gagaaannnn nnnnt                                              25

<210> SEQ ID NO 94
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
   the invention
<220> FEATURE:
<221> NAME/KEY: misc_feature
<222> LOCATION: (18)..(18)
<223> OTHER INFORMATION: n = 2-thiothymine, nonstandard nucleotide of
   the invention
<220> FEATURE:
<221> NAME/KEY: misc_feature
<222> LOCATION: (19)..(19)
<223> OTHER INFORMATION: n = N4-ethylcytosine, nonstandard nucleotide of
   the invention
<220> FEATURE:
<221> NAME/KEY: misc_feature
<222> LOCATION: (20)..(20)
<223> OTHER INFORMATION: n = N4-ethylcytosine, nonstandard nucleotide of
   the invention
<220> FEATURE:
<221> NAME/KEY: misc_feature
<222> LOCATION: (21)..(21)
<223> OTHER INFORMATION: n = 2-aminopurine, nonstandard nucleotide of
   the invention
<220> FEATURE:
<221> NAME/KEY: misc_feature
<222> LOCATION: (22)..(22)
<223> OTHER INFORMATION: n = N4-ethylcytosine, nonstandard nucleotide of
   the invention
<220> FEATURE:
<221> NAME/KEY: misc_feature
<222> LOCATION: (23)..(23)
<223> OTHER INFORMATION: n = 2-aminopurine, nonstandard nucleotide of
   the invention
<220> FEATURE:
<221> NAME/KEY: misc_feature
<222> LOCATION: (24)..(24)
<223> OTHER INFORMATION: n = hypoxanthine, nonstandard nucleotide of the
   invention
<220> FEATURE:
<223> OTHER INFORMATION: Synthetic

<400> SEQUENCE: 94
ttttacttac tctcgtnnnn nnnna                                              25

<210> SEQ ID NO 95
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
   the invention
<220> FEATURE:
<221> NAME/KEY: misc_feature
<222> LOCATION: (18)..(18)
<223> OTHER INFORMATION: n = 2-aminopurine, nonstandard nucleotide of
   the invention
<220> FEATURE:
<221> NAME/KEY: misc_feature
<222> LOCATION: (19)..(19)
<223> OTHER INFORMATION: n = 2-thiothymine, nonstandard nucleotide of -continued

```
      the invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 95
tattcgacag catgccnnnn nnnnc                                          25

<210> SEQ ID NO 96
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
      the invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
```

<223> OTHER INFORMATION: Synthetic

<400> SEQUENCE: 96
tcaatgcatg ctgtttnnnn nnnng                                              25

<210> SEQ ID NO 97
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 97
ctaatactgt ttcgtannnn nnnnt                                              25

<210> SEQ ID NO 98
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:

```
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 98
ctcttaccag ctacttnnnn nnnng                                           25

<210> SEQ ID NO 99
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = 2-thiothymine, nonstandard nucleotide of
      the invention
<220> FEATURE:
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = hypoxanthine, nonstandard nucleotide of the
      invention
<220> FEATURE:
<223> OTHER INFORMATION: Synthetic
```

-continued

<400> SEQUENCE: 99
aataaagacc tttgtgnnnn nnnng                                              25

<210> SEQ ID NO 100
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-thiothymine, nonstandard nucleotide of
      the invention
<220> FEATURE:
<221> NAME/KEY: misc_feature
<222> LOCATION: (18)..(18)
<223> OTHER INFORMATION: n = hypoxanthine, nonstandard nucleotide of the
      invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 100
atgttccatg taatacnnnn nnnnc                                              25

<210> SEQ ID NO 101
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)

```
<223> OTHER INFORMATION: n = hypoxanthine, nonstandard nucleotide of the
      invention
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = 2-aminopurine, nonstandard nucleotide of
      the invention
<220> FEATURE:
<223> OTHER INFORMATION: Synthetic

<400> SEQUENCE: 101
ccatatttct tttctgnnnn nnnnt                                            25

<210> SEQ ID NO 102
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 102
```

```
ggtctctcat ggcactnnnn nnnnc                                      25
```

<210> SEQ ID NO 103
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 103

```
cgggagcccc cgttctnnnn nnnna                                      25
```

<210> SEQ ID NO 104
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
      the invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention

```
<220> FEATURE:
<221> NAME/KEY: misc_feature
<222> LOCATION: (21)..(21)
<223> OTHER INFORMATION: n = N4-ethylcytosine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = N4-ethylcytosine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 104
atgaacttca tttaatnnnn nnnnt                                           25

<210> SEQ ID NO 105
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = 2-thiothymine, nonstandard nucleotide of
      the invention
<220> FEATURE:
<221> NAME/KEY: misc_feature
<222> LOCATION: (20)..(20)
<223> OTHER INFORMATION: n = hypoxanthine, nonstandard nucleotide of the
      invention
<220> FEATURE:
<221> NAME/KEY: misc_feature
<222> LOCATION: (21)..(21)
<223> OTHER INFORMATION: n = hypoxanthine, nonstandard nucleotide of the
      invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 105
gtacaaactg gtggtgnnnn nnnna                                           25
```

```
<210> SEQ ID NO 106
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = N4-ethylcytosine, nonstandard nucleotide of
      the invention
<220> FEATURE:
<221> NAME/KEY: misc_feature
<222> LOCATION: (18)..(18)
<223> OTHER INFORMATION: n = 2-aminopurine, nonstandard nucleotide of
      the invention
<220> FEATURE:
<221> NAME/KEY: misc_feature
<222> LOCATION: (19)..(19)
<223> OTHER INFORMATION: n = 2-aminopurine, nonstandard nucleotide of
      the invention
<220> FEATURE:
<221> NAME/KEY: misc_feature
<222> LOCATION: (20)..(20)
<223> OTHER INFORMATION: n = N4-ethylcytosine, nonstandard nucleotide of
      the invention
<220> FEATURE:
<221> NAME/KEY: misc_feature
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = 2-aminopurine, nonstandard nucleotide of
      the invention
<220> FEATURE:
<221> NAME/KEY: misc_feature
<222> LOCATION: (23)..(23)
<223> OTHER INFORMATION: n = hypoxanthine, nonstandard nucleotide of the
      invention
<220> FEATURE:
<221> NAME/KEY: misc_feature
<222> LOCATION: (24)..(24)
<223> OTHER INFORMATION: n = N4-ethylcytosine, nonstandard nucleotide of
      the invention
<220> FEATURE:
<223> OTHER INFORMATION: Synthetic

<400> SEQUENCE: 106
ctggtctcag ctgcttnnnn nnnnt                                          25

<210> SEQ ID NO 107
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = hypoxanthine, nonstandard nucleotide of the
      invention
<220> FEATURE:
<221> NAME/KEY: misc_feature
<222> LOCATION: (18)..(18)
<223> OTHER INFORMATION: n = 2-thiothymine, nonstandard nucleotide of
      the invention
<220> FEATURE:
<221> NAME/KEY: misc_feature
<222> LOCATION: (19)..(19)
<223> OTHER INFORMATION: n = N4-ethylcytosine, nonstandard nucleotide of
      the invention
<220> FEATURE:
<221> NAME/KEY: misc_feature
<222> LOCATION: (20)..(20)
<223> OTHER INFORMATION: n = 2-aminopurine, nonstandard nucleotide of
      the invention
<220> FEATURE:
<221> NAME/KEY: misc_feature
```

```
<222> LOCATION: (21)..(21)
<223> OTHER INFORMATION: n = 2-thiothymine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = 2-aminopurine, nonstandard nucleotide of
      the invention
<220> FEATURE:
<221> NAME/KEY: misc_feature
<222> LOCATION: (24)..(24)
<223> OTHER INFORMATION: n = hypoxanthine, nonstandard nucleotide of the
      invention
<220> FEATURE:
<223> OTHER INFORMATION: Synthetic

<400> SEQUENCE: 107
gttcattatc atctttnnnn nnnnc                                           25

<210> SEQ ID NO 108
<211> LENGTH: 25
<212> TYPE: DNA
<213> ORGANISM: Artificial Sequence
<220> FEATURE:
<221> NAME/KEY: misc_feature
<222> LOCATION: (17)..(17)
<223> OTHER INFORMATION: n = 2-aminopurine, nonstandard nucleotide of
      the invention
<220> FEATURE:
<221> NAME/KEY: misc_feature
<222> LOCATION: (18)..(18)
<223> OTHER INFORMATION: n = hypoxanthine, nonstandard nucleotide of the
      invention
<220> FEATURE:
<221> NAME/KEY: misc_feature
<222> LOCATION: (19)..(19)
<223> OTHER INFORMATION: n = hypoxanthine, nonstandard nucleotide of the
      invention
<220> FEATURE:
<221> NAME/KEY: misc_feature
<222> LOCATION: (20)..(20)
<223> OTHER INFORMATION: n = 2-thiothymine, nonstandard nucleotide of
      the invention
<220> FEATURE:
<221> NAME/KEY: misc_feature
<222> LOCATION: (21)..(21)
<223> OTHER INFORMATION: n = 2-aminopurine, nonstandard nucleotide of
      the invention
<220> FEATURE:
<221> NAME/KEY: misc_feature
<222> LOCATION: (22)..(22)
<223> OTHER INFORMATION: n = N4-ethylcytosine, nonstandard nucleotide of
      the invention
<220> FEATURE:
<221> NAME/KEY: misc_feature
<222> LOCATION: (23)..(23)
<223> OTHER INFORMATION: n = 2-thiothymine, nonstandard nucleotide of
      the invention
<220> FEATURE:
<221> NAME/KEY: misc_feature
<222> LOCATION: (24)..(24)
<223> OTHER INFORMATION: n = 2-thiothymine, nonstandard nucleotide of
      the invention
<220> FEATURE:
<223> OTHER INFORMATION: Synthetic

<400> SEQUENCE: 108
taggtgcttt attttnnnn nnnnc                                            25

<210> SEQ ID NO 109
```

```
<211> LENGTH: 15
<212> TYPE: DNA
<213> ORGANISM: Artificial Sequence
<220> FEATURE:
<223> OTHER INFORMATION: Synthetic

<400> SEQUENCE: 109
acttgatcgc ttggt                                                  15

<210> SEQ ID NO 110
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 5-methypyrimidin-2-one, C*, nonstandard
      nucleotide of the invention
<220> FEATURE:
<223> OTHER INFORMATION: Synthetic

<400> SEQUENCE: 110
acttgatngc ttggt                                                  15

<210> SEQ ID NO 111
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 4-methypyrimidin-2-one, 4mC*, nonstandard
      nucleotide of the invention
<220> FEATURE:
<223> OTHER INFORMATION: Synthetic

<400> SEQUENCE: 111
acttgatngc ttggt                                                  15

<210> SEQ ID NO 112
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 4,5-nimethypyrimidin-2-one, 45nmC*,
      nonstandard nucleotide of the invention
<220> FEATURE:
<223> OTHER INFORMATION: Synthetic

<400> SEQUENCE: 112
acttgatngc ttggt                                                  15

<210> SEQ ID NO 113
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = N4-methnlcntonine, N4mU, nonstandard
      nucleotide of the invention
<220> FEATURE:
<223> OTHER INFORMATION: Synthetic

<400> SEQUENCE: 113
acttgatngc ttggt                                                  15
```

```
<210> SEQ ID NO 114
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = N4-ethylcytosine, N4eU, nonstandard
      nucleotide of the invention
<220> FEATURE:
<223> OTHER INFORMATION: Synthetic

<400> SEQUENCE: 114
acttgatngc ttggt                                                    15

<210> SEQ ID NO 115
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = N4-methnl-5-methnlcntonine, N4mT,
      nonstandard nucleotide of the invention
<220> FEATURE:
<223> OTHER INFORMATION: Synthetic

<400> SEQUENCE: 115
acttgatngc ttggt                                                    15

<210> SEQ ID NO 116
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = N4-etnnl-5-methnlcntonine,N4eT, nonstandard
      nucleotide of the invention
<220> FEATURE:
<223> OTHER INFORMATION: Synthetic

<400> SEQUENCE: 116
acttgatngc ttggt                                                    15

<210> SEQ ID NO 117
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-aminoanenine, nonstandard nucleotide of
      the invention
<220> FEATURE:
<223> OTHER INFORMATION: Synthetic

<400> SEQUENCE: 117
acttgatngc ttggt                                                    15

<210> SEQ ID NO 118
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-aminoanenine, nonstandard nucleotide of
      the invention
<220> FEATURE:
<223> OTHER INFORMATION: Synthetic
```

```
<400> SEQUENCE: 118
acttgatngc ttggt                                                    15

<210> SEQ ID NO 119
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-metnnlnnpoxantnine, nonstandard
      nucleotide of the invention
<220> FEATURE:
<223> OTHER INFORMATION: Synthetic

<400> SEQUENCE: 119
acttgatngc ttggt                                                    15

<210> SEQ ID NO 120
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 2-metnnlnnpoxantnine, nonstandard
      nucleotide of the invention
<220> FEATURE:
<223> OTHER INFORMATION: Synthetic

<400> SEQUENCE: 120
acttgatngc ttggt                                                    15

<210> SEQ ID NO 121
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = N4-ethylcytosine, N4eU, nonstandard
      nucleotide of the invention
<220> FEATURE:
<223> OTHER INFORMATION: Synthetic

<400> SEQUENCE: 121
acttgatngc ttggt                                                    15

<210> SEQ ID NO 122
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = 4-methypyrimidin-2-one, 4mC*, nonstandard
      nucleotide of the invention
<220> FEATURE:
<223> OTHER INFORMATION: Synthetic

<400> SEQUENCE: 122
acttgatngc ttggt                                                    15

<210> SEQ ID NO 123
<211> LENGTH: 15
<212> TYPE: DNA
<213> ORGANISM: Artificial Sequence
<220> FEATURE:
```

```
<221> NAME/KEY: misc_feature
<222> LOCATION: (8)..(8)
<223> OTHER INFORMATION: n = N4-methnlcntonine, N4mU, nonstandard
      nucleotide of the invention
<220> FEATURE:
<223> OTHER INFORMATION: Synthetic

<400> SEQUENCE: 123
acttgatngc ttggt                                               15

<210> SEQ ID NO 124
<211> LENGTH: 15
<212> TYPE: DNA
<213> ORGANISM: Artificial Sequence
<220> FEATURE:
<221> NAME/KEY: misc_feature
<222> LOCATION: (8)..(8)
<223> OTHER INFORMATION: n = N4-methnl-5-methnlcntonine, N4mT,
      nonstandard nucleotide of the invention
<220> FEATURE:
<223> OTHER INFORMATION: Synthetic

<400> SEQUENCE: 124
acttgatngc ttggt                                               15
```

SELF-AVOIDING MOLECULAR RECOGNITION SYSTEMS IN DNA PRIMING

Continuation in part of U.S. patent application Ser. No. 11/647,609 Which is a Continuation in part of U.S. patent application Ser. No. 11/271,366 Which is based on provisional patent applications 60/627,460 and 60/627,459

FIELD

This invention relates to the field of nucleic acid chemistry, more specifically to the field of compositions and processes that can serve as primers for the copying of DNA and RNA. Most specifically, this invention relates to compositions of matter that bind to natural DNA and RNA following simple rules as they serve as primers, without binding as strongly to themselves.

BACKGROUND

Over the past 15 years scientists have sought innovative molecular recognition systems that have binding properties that are useful in different ways. The structures of these systems have been modeled along the lines of DNA and RNA. Further, as with DNA and RNA, the molecular recognition systems have been useful because they bind to other components of the molecular recognition systems and/or to natural DNA and RNA following rules that can be expressed in a form that guides practitioners of ordinary skill in the art and enables them to do useful things.

DNA serves as an archetype to illustrate both molecular structure and rule base recognition. With DNA, three rules (A pairs with T, G pairs with C, the strands are antiparallel) permit the design of two DNA molecules that bind to each other in aqueous solution. When the rules are perfectly followed, two perfectly complementary DNA strands of a substantial length (15-20 nucleotides is normally sufficient in physiological buffers at 37° C.) will bind to each other with substantial selectivity even in complex mixtures containing many other DNA molecules.

Heuristic rules have been developed over the years to permit the prediction of general trends in DNA:DNA binding affinity. These have come by performing substantial numbers of melting temperature experiments. For examples as heuristic rules, longer DNA strands generally bind to their partners with higher melting temperatures (Tms) than shorter strands. G:C pairs generally contribute more to duplex stability than A:T pairs. More highly parameterized models improve on the estimates of melting temperatures [All198a][All198b] [Mar85][Mat98]. While it remains true that the precise stability of duplexes may not be predictable, that imprecision does not defeat the utility of DNA:DNA binding or require undue experimentation to exploit, even though the number of different DNA sequences of length n (=4") that would fall within a patent for the DNA molecular recognition system would be enormous.

It has been argued that this rule-based behavior arises because of the repeating charge in the backbone of nucleic acids [Ben04]. Certainly, analogs that have that repeating charges in their backbone maintain their rule-based pairing behavior even if they become quite long. In contrast, the few examples of useful nucleic acid analogs that lack a repeating charge in their backbone do not maintain their rule-based binding behavior in polymers built from two dozen or more monomer units (fewer if the nucleobases are predominately guanine). The archetypal example of such an uncharged DNA analog is the peptide nucleic acids (PNAs) [Egh92], where rule-based molecular recognition does not survive in longer molecules.

Orthogonal Binding Systems (FIG. 1)

An archetype of a human-invented rule-based molecular recognition is the artificially expanded genetic information system (AEGIS) disclosed in U.S. Pat. No. 5,432,272. The design of this artificial molecular recognition system began with the observation that two principles of complementarity govern the Watson-Crick pairing of nucleic acids: size complementarity (large purines pair with small pyrimidines) and hydrogen bonding complementarity (hydrogen bond donors from one nucleobase pair with hydrogen bond acceptors from the other). These two principles give rise to the simple rules for base pairing ("A pairs with T, G pairs with C") that underlie genetics, molecular biology, and biotechnology.

U.S. Pat. No. 5,432,272 pointed out that these principles can be met by nucleotides other than adenine (A) and thymine (T), and guanine (G) and cytosine (C). Rather, twelve nucleobases forming six base pairs joined by mutually exclusive hydrogen bonding patterns might be possible within the geometry of the Watson-Crick base pair. FIG. 1 shows some of the standard and non-standard nucleobase pairs, together with the nomenclature to designate them. Those nucleobase analogs presenting non-standard hydrogen bonding patterns are part of an Artificially Expanded Genetic Information System, or AEGIS.

U.S. Pat. No. 5,432,272 and subsequent patents all taught that the hydrogen bonding pattern that makes an AEGIS component useful as a unit of molecular recognition is distinguishable from the heterocycle that implements it. This means that different heterocycles can often serve interchangeably as molecular recognition elements. This, in turn, permits the elements of an artificial molecular recognition system to be chosen based on considerations other than simple recognition. Thus, the pyADA hydrogen bonding pattern in AEGIS is implemented by thymidine, uridine, uridine derivatives carrying a 5-position linker attached to a fluorescent moiety, uridine derivatives carrying a 5-position linker attached to a biotin, and pseudouridine, for example.

Four features of the AEGIS system make it suited for application:

(a) AEGIS supports rule-based design. Anyone of ordinary skill in the art can design two AEGIS-containing molecules that bind to each other, after learning only a few additional rules, just as they can design binding partners with standard DNA. Again, a critical mass of melting temperatures were collected to support heuristic rules that allow prediction of affinity. As with DNA, the precise Tns are not predictable even with these heuristic rules, but this imprecision does not defeat the utility of the system, or create a need for undue experimentation to design AEGIS pairing partners.

(b) This rule-based molecular recognition displayed by AEGIS is orthogonal to that displayed by standard DNA. If two strands incorporating standard DNA bases are mixed with two other strands incorporating AEGIS components, the first pair will bind to each other only, and the second pair will bind to each other only, without formation of hybrids between the strands containing canonical and non-canonical bases. This allows two molecular recognition processes to occur independently in the same vessel.

(c) Sequences built from AEGIS components have higher information density (more different sequences per unit length), especially when they incorporate the full 12 letters that the AEGIS technology allows. This allows fewer nearmismatches in complicated systems to slow hybridization, for example. Thus, AEGIS tags hybridize more quickly [Col97].

(d) Enzymes can be found that allow AEGIS systems to be manipulated in ways common in biotechnology with standard DNA. These enzymes include polymerases that do primer extension, copy templates that contain AEGIS components, and amplify AEGIS oligonucleotides a polymerase chain reaction (PCR). Here, undue experimentation is often required to obtain enzymes that do this effectively, as many natural enzymes regard non-standard nucleotides as "foreign", and do not accept them or, if they do, do not accept them with useful affinity.

An archetypal application of AEGIS is in the branched DNA (bDNA) assay used to measure levels of HIV, hepatitis B, and hepatitis C viruses in human patients [Elb04a] [Elb04b]. As this example shows, even though the behavior of DNA duplexes built from AEGIS components having different sequences are not identical and may not be precisely predictable, this has not prevented the AEGIS molecular recognition system from improving the health care of some 400,000 patients annually [Ben04]. This is an illustration of the utility of orthogonality in the analytical chemistry of nucleic acids.

The SNAP2 System (FIG. 2, FIG. 3)

The SNAP2 system, disclosed in U.S. Ser. Nos. 60/627, 460, 60/62745, 11/271,366 and 11/647,609, which are incorporated herein by reference, is designed to achieve yet a different molecular recognition specification: To obtain oligonucleotide molecules that bind to DNA and RNA with the specificity of a 16 mer, but the discriminatory power of 8 mers. These specifications are needed to solve certain problems intrinsic in the selective probing of large transcriptomes or genomes. For example, as the human genome has ca. $3 \times 10^9$ nucleotide sequences, a probe that is 16 nucleotides long will bind, on average, to just one sequence within that genome (pace due to repeats, the variance on that average is much larger than would be expected if the genome sequence were unbiased). Such calculations suggest that a probe must be 16 nucleotides in length to seek a specific NA segment in a human genome. Unfortunately, for duplexes of this length under standard hybridization conditions, single mismatches depress the melting temperatures only slightly. Further, the AT and GC nucleobase pairs have different intrinsic affinities, and contribute to duplex stability differently depending on the local "sequence context". Together, this means that a duplex built from a pair of two 16-mers having two, three, or occasionally more mismatches can easily be more stable than another duplex built from a pair of two perfectly matched 16-mers. This creates difficulties throughout the analytical chemistry of nucleic acids, especially when attempting to multiplex.

Of course, if the duplex is shorter, then any pair of perfectly matched sequences will form a more stable duplex than any pair of duplexes that fail in complementarity by a single mismatch. For NA-NA duplexes under standard hybridization conditions, this is met by duplexes as short as 6 nucleobase pairs. These, however, lack specificity in the human genome (a 6-mer is found on average a million times in the human genome).

In the SNAP2 architecture, a primer is assembled with the assistance of the template on which it will prime. The primers are short enough so that they display strong discrimination against single nucleotide mismatches. In the SNAP2 patent application, these fragments are typically 6-8 nucleotides long. The 3'-fragment is chosen so that it does not prime oligonucleotide synthesis on a nucleic acid template by itself. The 3'-fragment does, however, prime oligonucleotide synthesis if it is assisted by a 5'-fragment. As the complete template complementary to both fragments must be present for priming to occur, the priming has the selectivity of (for example) a 14 mer (if the fragments are 8+6 nucleotides in length), but the discriminatory power against single nucleotide mismatches characteristic of 8 mers and 6 mers, respectively.

Self Avoiding Genetic Systems

The SNAP2 system disclosed in U.S. Ser. Nos. 60/627,460, 60/62745, 11/271,366 and 11/647,609 created a need for yet a different binding behavior, which we have called "self-avoiding". The self-avoiding property can be understood by comparison with the molecular recognition behavior of the AEGIS system. The AEGIS system provides AEGIS components bind to other AEGIS components via simple rules, but that do not bind to natural DNA or RNA (orthogonality). A self-avoiding molecular recognition system (SAMRS) does exactly the opposite. The components of a SAMRS do bind to natural DNA or RNA, but not to other components of the same unnatural system.

In its general description, a SAMRS incorporates nucleobase analogs that replace T, A, G, and C by analogs that are indicated as T*, A*, G*, and C*, which are collectively called "* analogs" of T, A, G, and C respectively. In the simplest implementation of this concept, these * analogs are each able to form two hydrogen bonds to the complementary A, T, C, and G. This means that the T*:A, A*:T, C:*G, and G*:C nucleobase pairs contribute to duplex stability to approximately the same extent as an A:T pair. A SAMRS obtains its self-avoiding properties because the hydrogen bonding groups of the * analogs are chosen the T*:A* and C*:G* nucleobase pairs do not contribute as much to duplex stability because (in the simplest implementation) they are joined by only one hydrogen bond.

As with standard DNA, standard RNA, and AEGIS molecular recognition systems, within a SAMRS system, predicting the binding properties of any sequence will be subject to the same imprecision as predicting the properties of an arbitrary DNA or AEGIS molecule. Thus, as a general rule, if individuals of ordinary skill in the art wish to design a SAMRS sequence that binds to a preselected standard DNA molecule with a Tm of 25° C., they would write down the preselected sequence in the 5'-to-3' direction, and then write below the SAMRS sequence in an antiparallel direction, matching a T* against every A in the preselected sequence, an A* against every T in the preselected sequence, a C* against every G in the preselected sequence, and a G* against every C in the preselected sequence. It is an open question as to whether such simple instructions allow one of ordinary skill in the art to obtain useful outcomes without undue experimentation. As elaborated below, attempts to obtain such utility failed when we took instruction from the prior art. One object of the instant invention is to provide SAMRS components that provide utility based on precisely this simple a set of rules and instructions.

As disclosed in U.S. Ser. Nos. 60/627,460, 60/62745, 11/271,366 and 11/647,609, the need for self-avoiding behaviors was pressing when one sought to have mixtures containing more than two oligonucleotides, and was especially pressing when making libraries of oligonucleotides (defined as having 10 or more oligonucleotide components), especially when those oligonucleotides were to interact with enzymes such as DNA polymerases. This problem is exemplified by multiplexed PCR, where the amplification is sought of many segments of DNA in one pot. This is attempted by adding in large excess two primers flanking each segment, contacting mixture with nucleoside triphosphates, and cycling the mixture up and down in temperature in the presence of a thermostable DNA polymerase. At low temperatures, the primers anneal to the template. At higher temperatures, the polymerase extends the primer to make a product copy of the template. At the highest temperature, the product copy falls off the template, allowing more primers to bind when the temperature is dropped. The primers competing with full length product copies for their binding sites on the template by being present in high concentrations.

While PCR can be successfully multiplexed up to a dozen or so amplicons, with careful design to avoid having the primers present in high concentrations interact with each other, eventually even the most careful design does not prevent primer-primer interactions. These create undesired amplicons, primer dimers, and other artifacts that defeat the utility of the PCR. U.S. Ser. Nos. 60/627,460, 60/62745, 11/271,366 and 11/647,609 contemplated libraries of such primers in the SNAP2 architecture. Here, self-avoidance was necessary to prevent "messes" from arising. The problem is also pressing if one wishes to do simple primer extension with libraries of primers.

U.S. Ser. Nos. 60/627,460, 60/62745, 11/271,366 and 11/647,609 disclosed two sets of nucleotides that could implement the SAMRS structures. These are shown in FIG. 4 and FIG. 5. These were in addition to a few structures that were already present in the literature that, although not used in primers or PCR, might be applied in a SAMRS priming system.

The first of these was disclosed by U.S. Pat. No. 5,912,340 a decade ago. U.S. Pat. No. 5,912,340 was not concerned with creating primers for DNA polymerases, or multiplexed PCR. Instead, U.S. Pat. No. 5,912,340 claimed:

"a pair of oligonucleotides (ODNs), each of said ODNs comprising nucleotide moieties having naturally occurring aglycon bases and a combination of modified aglycon bases selected from the group consisting of the combinations (1) A', (2) G', C', and (3) A', T', G', and C', the duplex form of said pair of ODNs having a melting temperature under physiological conditions of less than approximately 40° C., each of said pair of ODNs being substantially complementary in the Watson-Crick sense to one of the two strands of a duplexed target sequence in nucleic acid, wherein the nucleotide moieties having the modified bases have the following properties:

With complementary oligonucleotides A' does not form a stable hydrogen bonded base pair with T' and forms a stable hydrogen bonded base pair with T;

With complementary oligonucleotides T' does not form a stable hydrogen bonded base pair with A' and forms a stable hydrogen bonded base pair with A;

With complementary oligonucleotides G' does not form a stable hydrogen bonded base pair with C' and forms a stable hydrogen bonded base pair with C;

With complementary oligonucleotides C' does not form a stable hydrogen bonded base pair with G' and forms a stable hydrogen bonded base pair with G.

The inventors of U.S. Pat. No. 5,912,340 were satisfied if "sufficient" numbers of their primed nucleotides (analogous to the * analogs discussed here) were incorporated to prevent the two oligonucleotides in the pair from binding to each other, or (in later work) if sufficient numbers of the analogs were present to prevent the DNA or RNA molecule from folding on itself. U.S. Pat. No. 5,912,340 did not provide any melting temperatures, nor did subsequent work, nor did it provide assurance that one of ordinary skill in the art could get useful predictability (without undue experimentation) from oligonucleotides built from the components that they (and they and others in subsequent work) provided. As they provided no data with polymerases acting on these unnatural compounds as templates or primers, it was not certain that they would be accepted by polymerases, and it was definitively uncertain whether they would be accepted by polymerases with sufficient efficiency to support the demands of PCR.

Nor was it necessary for U.S. Pat. No. 5,912,340 or subsequent work to do so, as their principal goal was self-avoidance. They did not intend to provide (or, it seems, even contemplate providing) primers, let alone primers suitable for PCR.

Nor did they provide these. As the instant invention was developed as we faced the pressing demands mentioned above, we encountered significant difficulties, some described below, that forced the following conclusion: Even though, as their inventors, the instant applicants had the benefits of the teachings of U.S. Ser. Nos. 60/627,460, 60/62745, 11/271,366 and 11/647,609 (the predecessors of the instant application), the instant applicants would have been unable to get a functioning SAMRS for the purpose of priming and PCR based on the teachings of U.S. Pat. No. 5,912,340.

For example, U.S. Pat. No. 5,912,340 (Claim 2) suggests that the 3-position of purines can be a CH, not an N (see structure (i), where X can be either N or CH). While X may be able to be CH as taught in U.S. Pat. No. 5,912,340 for the utility taught in U.S. Pat. No. 5,912,340, the instant disclosure teaches, as a result of experimentation, that X cannot be CH for the purpose of creating primers to be used in PCR with SAMRS. Likewise, R* in structure (i) is taught by U.S. Pat. No. 5,912,340 to be possibly a cross-linking function or a reporter group; in contrast, the instant disclosure teaches that R* cannot have these structures. Likewise, R* in structure (ii) is taught by U.S. Pat. No. 5,912,340 to be possibly a cross-linking function or a reporter group; the instant disclosure teaches that R* in this structure must be H, and this teaching is again supported by experimentation. Likewise, $R_2$ in various structures in Claim 2 and Claim 3 is taught by U.S. Pat. No. 5,912,340 to be possibly alky, alkoxy, alkylthio, or F; the instant disclosure teaches that none of these are possible for the purposes of the instant invention.

Likewise, U.S. Pat. No. 5,912,340 taught that the replacement for C might be zebularine (Claim 5, structure (ix), $R_4$=H, $R_5$=H), either of the two mono-methyl analogs of zebularine (Claim 5, structure (ix), $R_4$=H, $R_5$=$CH_3$ or $R_4$=$CH_3$, $R_5$=H), or dimethyl zebularine (Claim 5, structure (ix), $R_4$=$CH_3$, $R_5$=$CH_3$). We tried all of these. We could achieve useful primers with a small number of these incorporated as C*. We could not, however, do this with large numbers. The preferred structure proposed by U.S. Pat. No. 5,912,340 as a replacement for cytidine seemed to be wholly unacceptable as a polymerase substrate. Only 2-thioT as a thymidine replacement and 2-aminopurine as an adenine replacement appear to be useful for our purposes of the instant invention.

This is certainly suggested by subsequent work examining systems evidently inspired by U.S. Pat. No. 5,912,340. For example, seeking triphosphates that would be incorporated by polymerases to create oligonucleotides that would not self-fold, Lahoud et al. [Lah08] were forced to set up a screen to identify these, even though certain coauthors of [Lah08] are the same as certain inventors for U.S. Pat. No. 5,912,340. [Lah08] does not overlap Ser. Nos. 60/627,460, 60/62745, 11/271,366 and 11/647,609 (predecessors of the instant application) or the instant application, because the instant application places the SAMRS components in the primers and templates and uses standard nucleoside triphosphates, while [Lah08] uses standard nucleotides in the primers and templates and incorporates certain SAMRS triphosphates. But clearly the prior art does not anticipate the invention of [Lah08], given that the same inventors were still screening a decade after U.S. Pat. No. 5,912,340 was filed.

The instant applicants do not intend to claim that U.S. Pat. No. 5,912,340 is not enabling for the utilities that it disclosed, which is primarily to get self-avoidance. The instant applicants make no teaching on this question. Nor are the teachings of U.S. Pat. No. 5,912,340 and the instant application necessarily contradictory, considering their very different utilities. The goal of U.S. Pat. No. 5,912,340 was to provide just two oligonucleotides that would not bind to each other, without making any reference to their ability to serve as primers, either directly or as part of PCR. One of our goals is to define libraries of oligonucleotides, defined as mixtures of 10 or more. A goal of subsequent systems based on the teachings of U.S. Pat. No. 5,912,340, under the name of "pseudocomplementarity", was to provide triphosphates that could be incorporated into oligonucleotides as triphosphates to give oligonucleotide products that would not self-fold. Another goal of subsequent systems based on the teachings of U.S. Pat. No. 5,912,340 was to incorporate the nucleobases taught into pairs of PNA molecules to allow them to invade duplex DNA without pairing to each other.

In contrast, the goal of the instant invention is to provide primers that could be extended by DNA polymerases when templated on a natural DNA, and to provide primers that could support PCR (which requires that a primer, after being extended, must also be accepted as a template by a DNA polymerase). Thus, there is no reason for U.S. Pat. No. 5,912,350 or any of the subsequent academic literature that is based on it to enable the instant invention, as it is not clear that anyone, prior to Ser. Nos. 60/627,460, 60/62745, 11/271,366 and 11/647,609 (the predecessors of the instant application), and the instant application considered using such molecules as primers, or as PCR primers, or as components of libraries.

Further issues relate directly to the use of SAMRS components in PCR. For example, the preferred compound for a G analog was inosine (U.S. Pat. No. 5,912,340, claims 11, 12, and 13). However, inosine is a deamination product of adenosine, and many thermostable polymerases of the type used in PCR were known to pause at inosine, presumably to permit the repair of this common defect.

The instant invention provides data concerning a range of possible SAMRS components, melting temperatures for many of these, and rules to permit their use in primers. This provides a critical mass to assemble first generation heuristic rules to predict the performance of the system.

Figure 9:
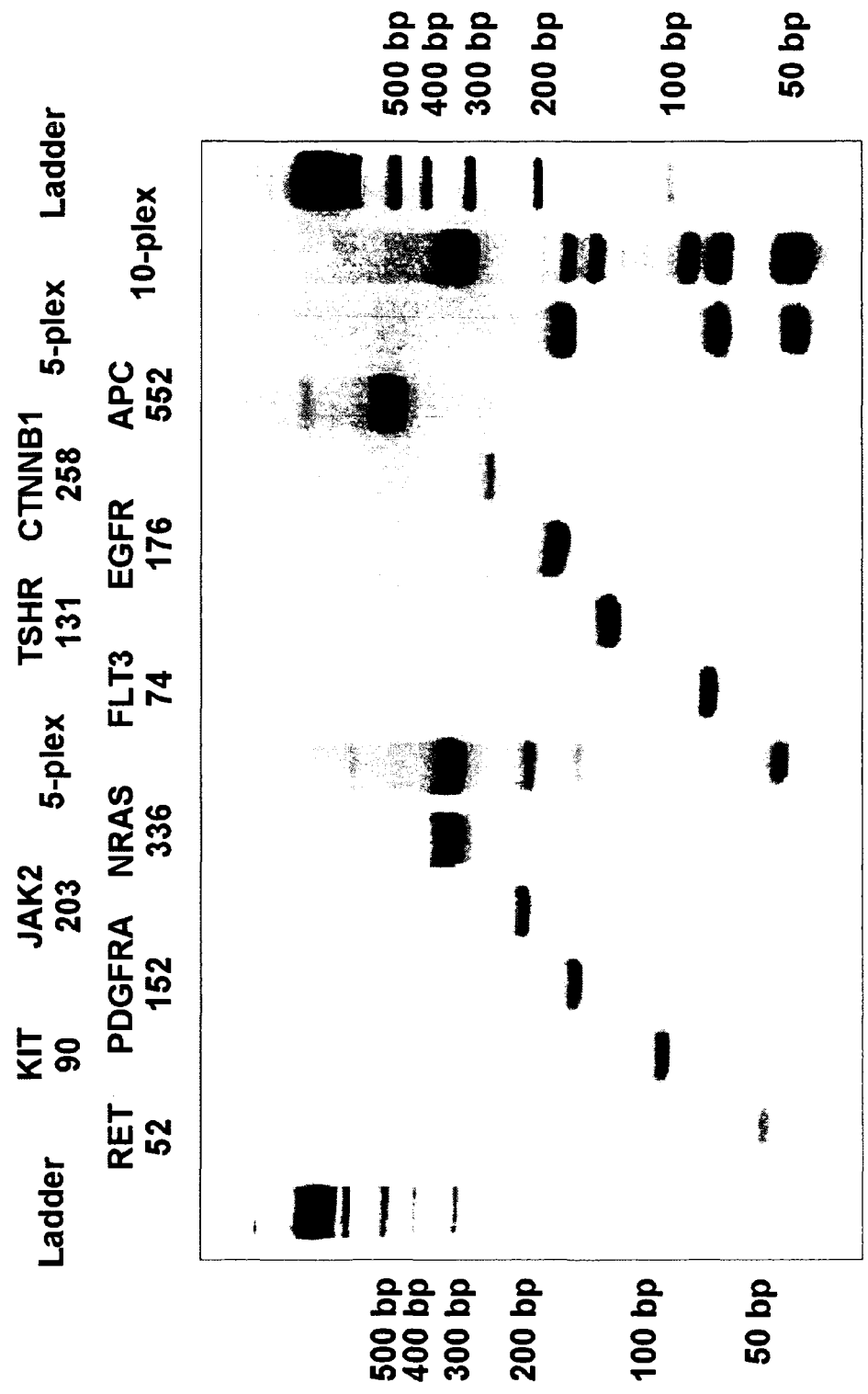
Figure 9:
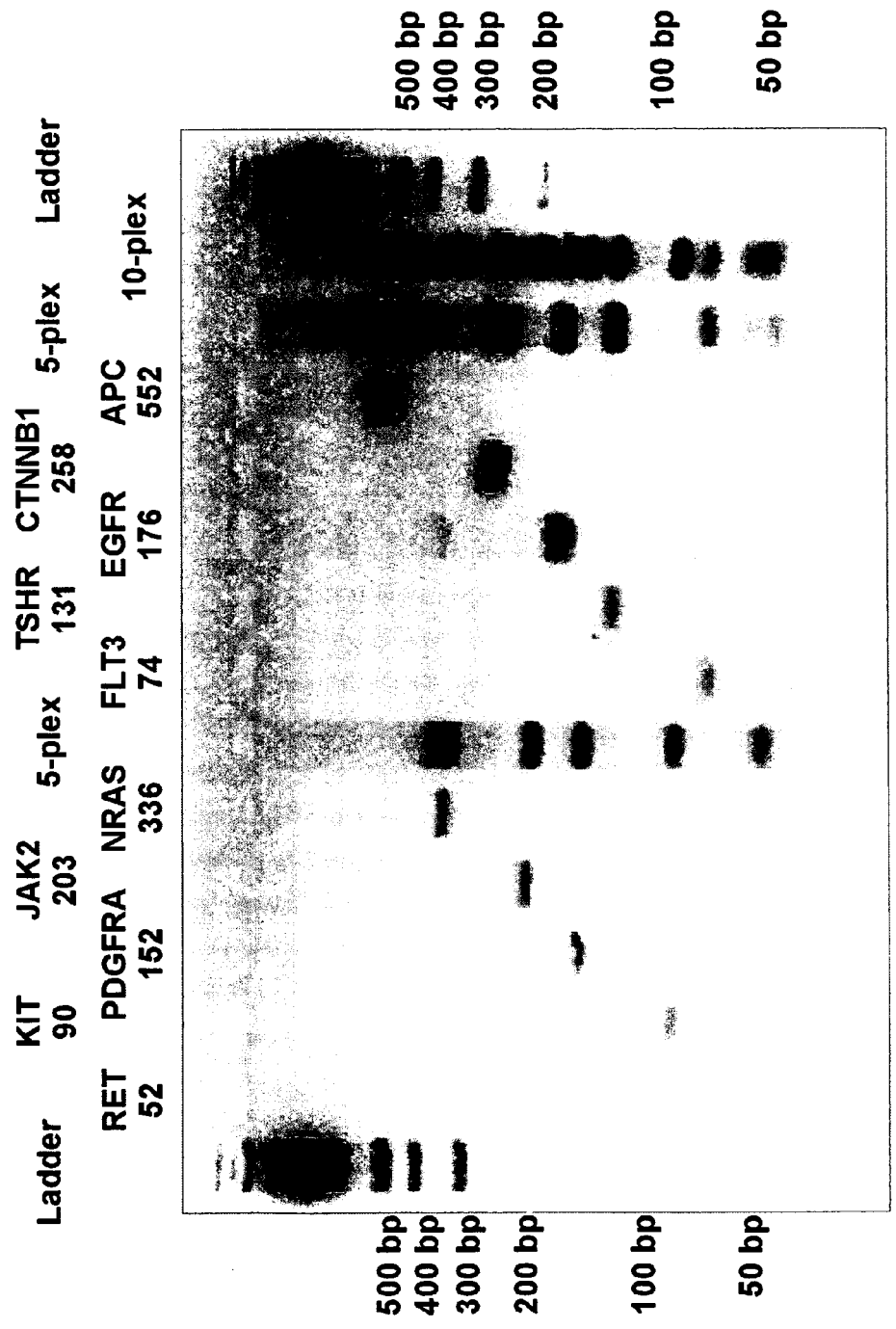

FIG. 9. Five- and ten-fold multiplexed PCR experiments with standard primers (FIG. 9a) and SAMRS chimeric primers (FIG. 9b), with SAMRS hydrogen bonding patterns implemented as follows: T* implemented with 2-thiothymine; A* implemented with 2-aminopurine; G* implemented with hypoxanthine; C* implemented with N4-ethylcytosine, with primers targeted against various cancer genes of interest. Template: Human genomic DNA, 25 ng/25 microL Primers each 200 nM. dNTPs each 1 mM. Additional 5 mM MgCl$_2$ for SAMRS primers. Taq polymerase: 5.0 units/0.025 mL. 40 cycles: denature at 94° C. for 1 min, then annealing at 55° C. for SAMRS and 60° C. for standard primers for 1 min; then primer extension at 72° C. for 90 sec. Products were resolved on a 3% agarose gel and visualized by phosphorimager (one primer 5'-radiolabeled).

Figure 10:
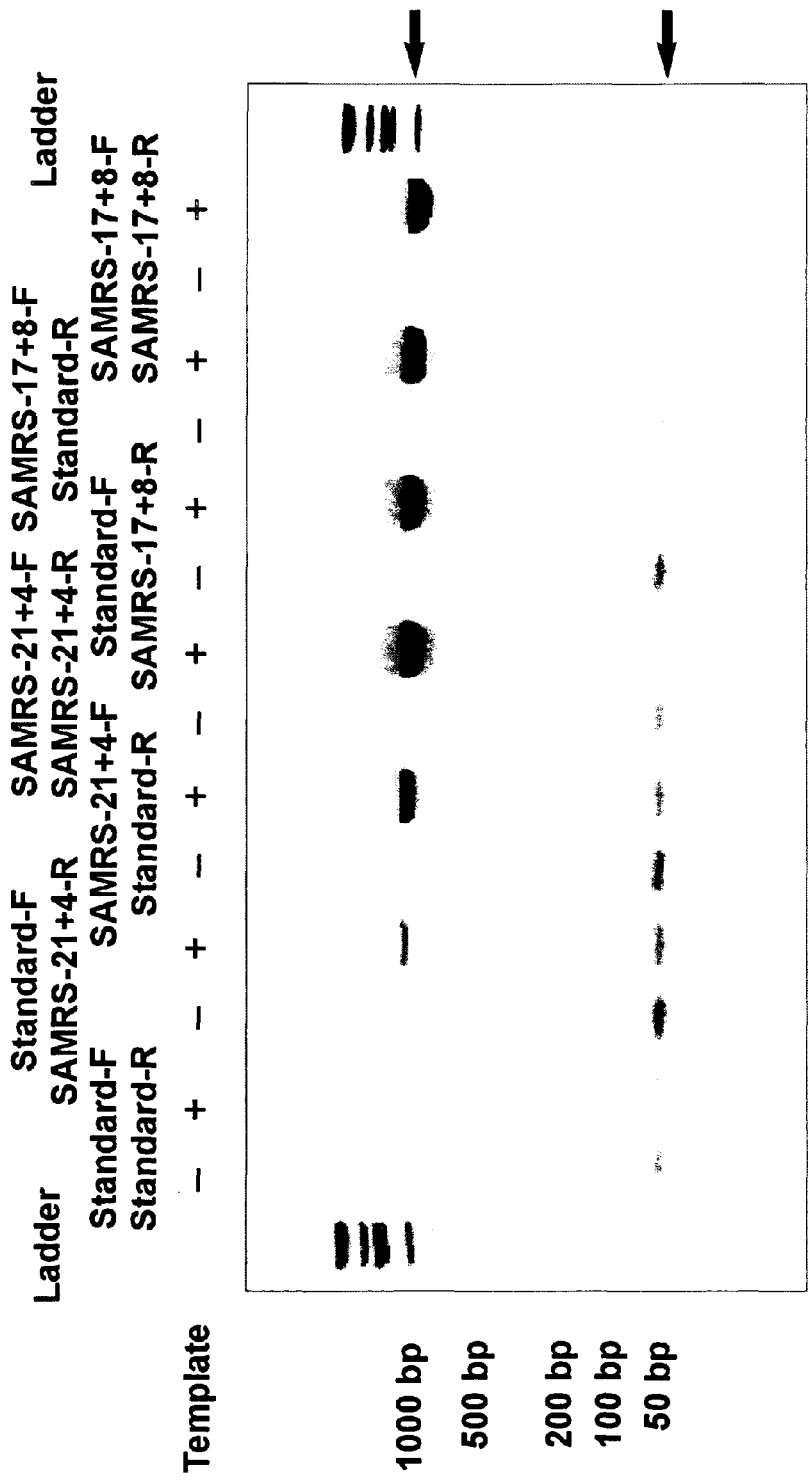

FIG. 10. Amplification of the Taq polymerase gene with these primers:

```
SAMRS-21+4-F:   5'-TAT CTG CGT GCC CTG TCT CTG* G*A*G* G-3'      SEQ ID NO 1

SAMRS-21+4-R:   5'-CCA ATG CCA ACC TCT ACC TCC* A*G*A* G-3'      SEQ ID NO 2

SAMRS-17+8-F:   5'-TAT CTG CGT GCC CTG TC*T* C*T*G* G*A*G* G-3'  SEQ ID NO 3

SAMRS-17+8-R:   5'-CCA ATG CCA ACC TCT AC*C* T*C*C* A*G*A* G-3'  SEQ ID NO 4
```
An * following a letter indicates that the heterocycle is one of the presently preferred implementations of the indicated base. As shown below, the primer pair was deliberately designed to have overlap that, when the standard primers were used, generated no full length product, but only primer dimer (lower arrow, 41 bps). The DNA in the 2% agarose gel was visualized with ethidium bromide.

Figure 11:
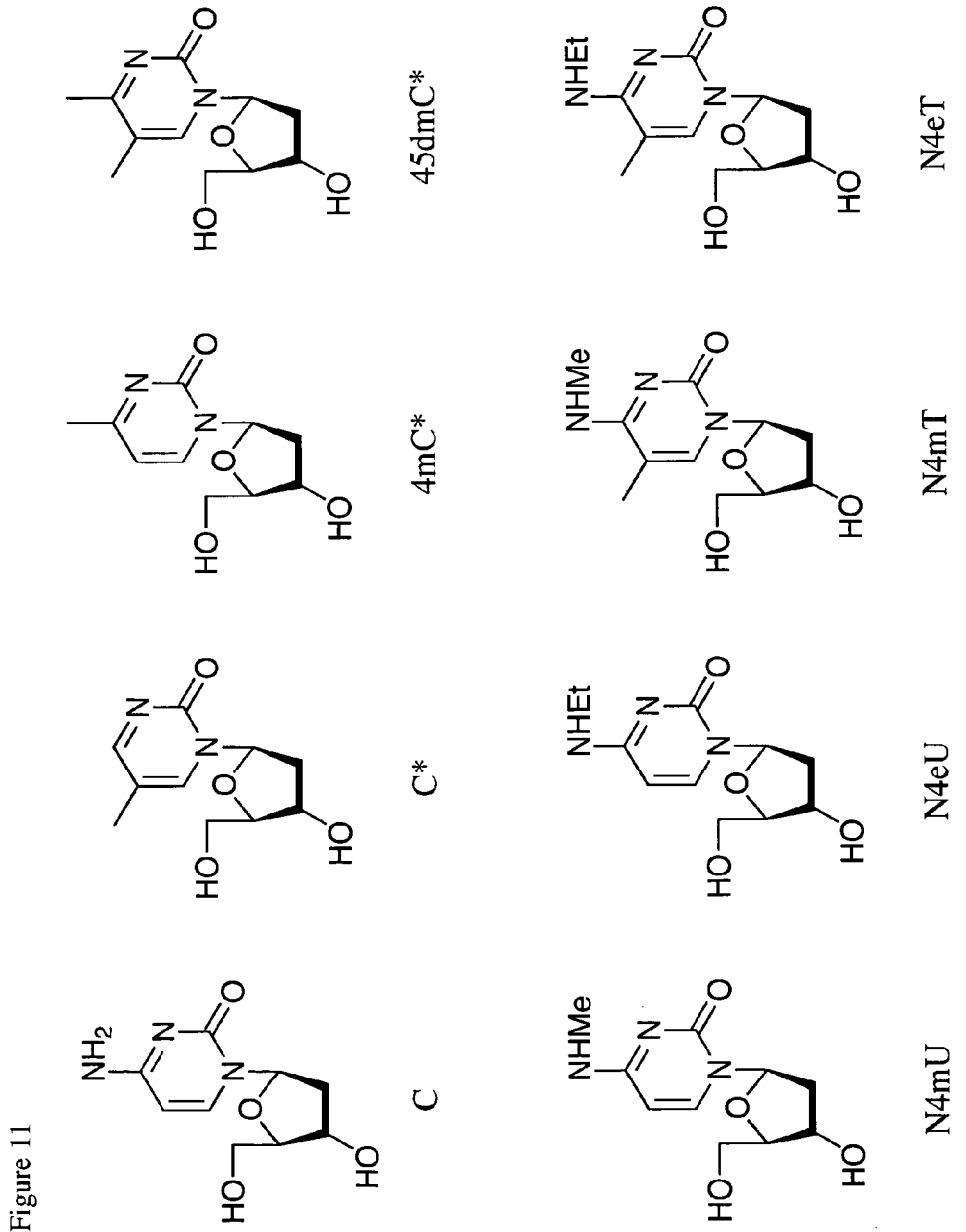

FIG. 11. Structures and abbreviations for various alternative implementations of C* examined.

Figure 12:
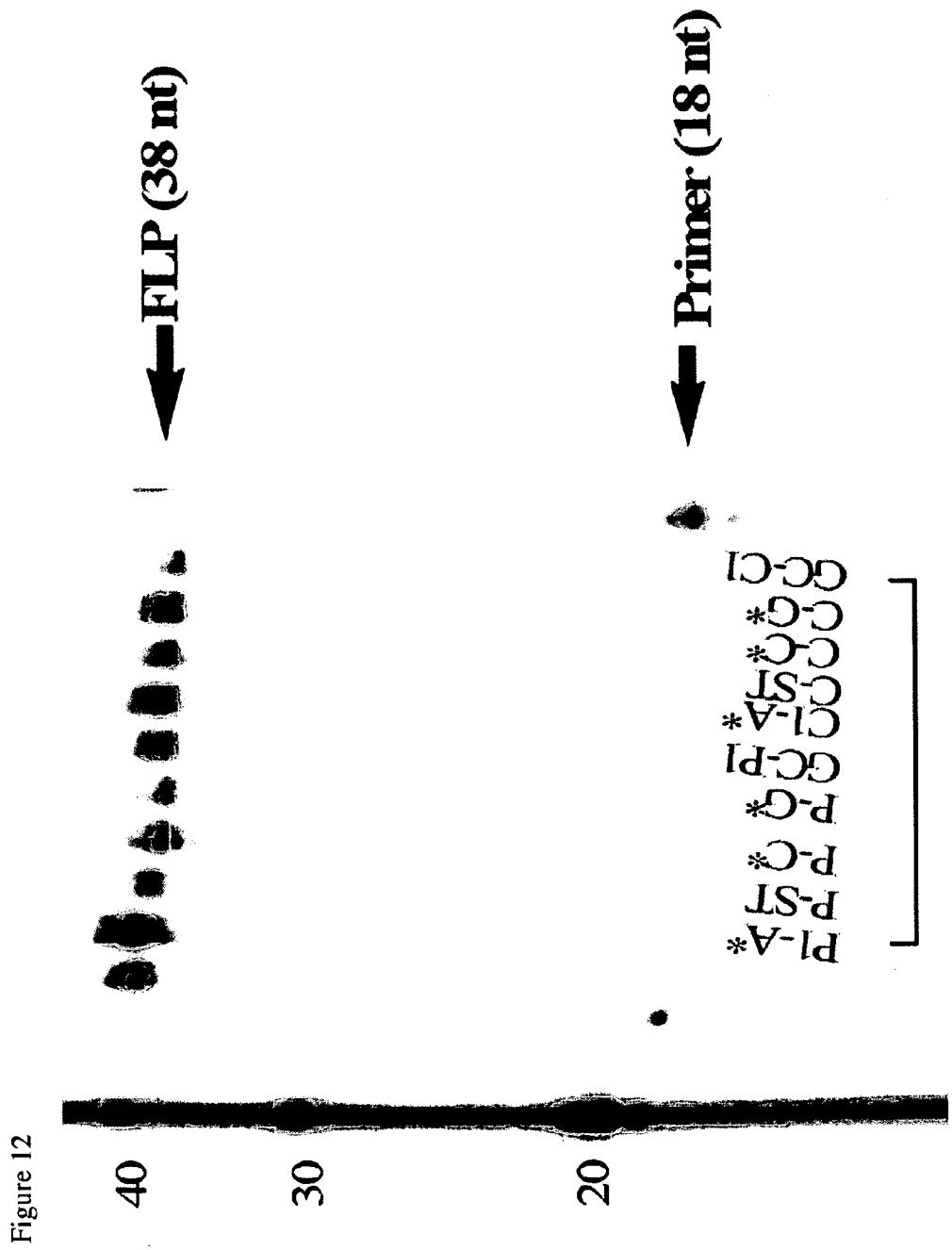

FIG. 12. Some primer extension of oligonucleotide templates containing scattered SAMRS components, reporting data collected in Example 13.

Figure 13:
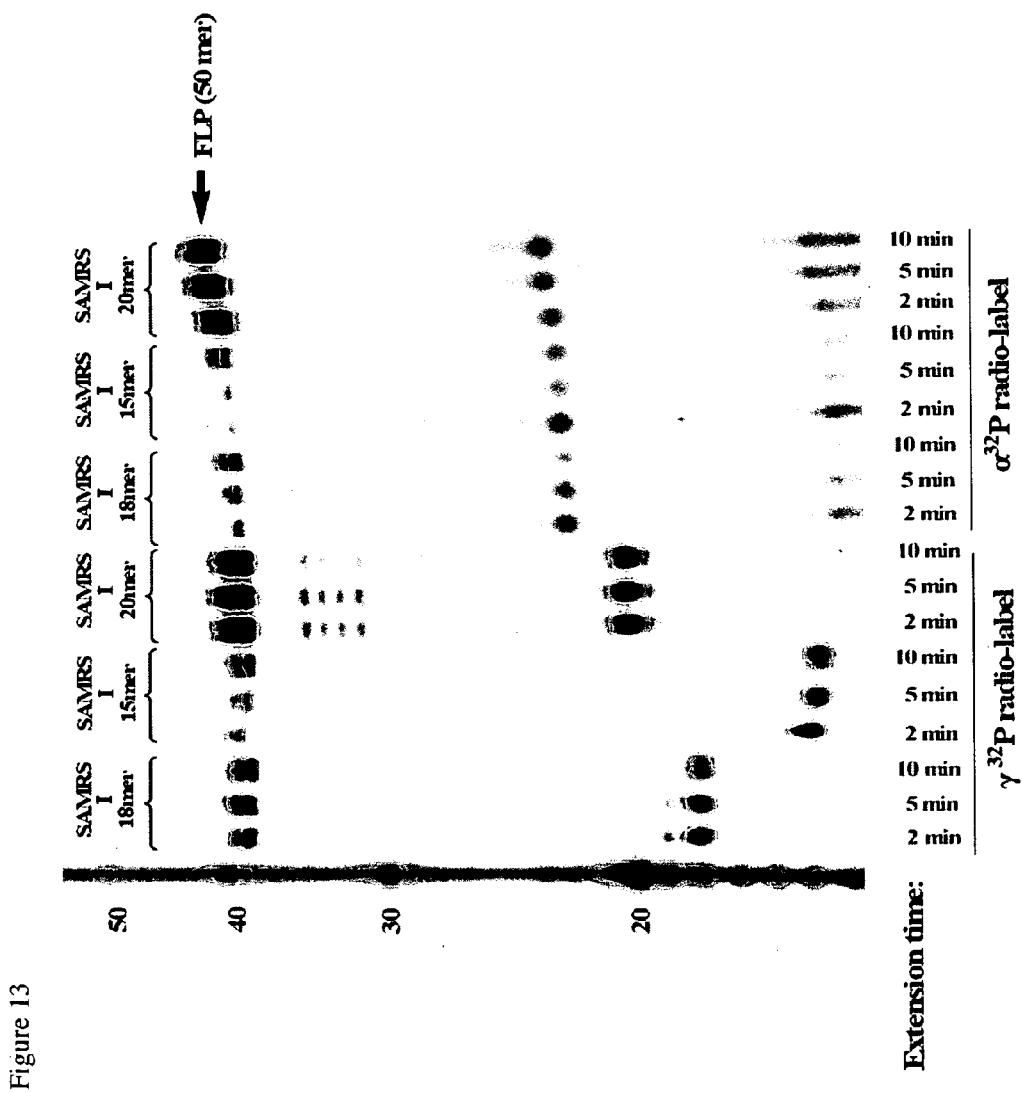

FIG. 13. Gel showing primer extensions using primers containing all SAMRS components reporting data collected in Example 14.

Figure 14:
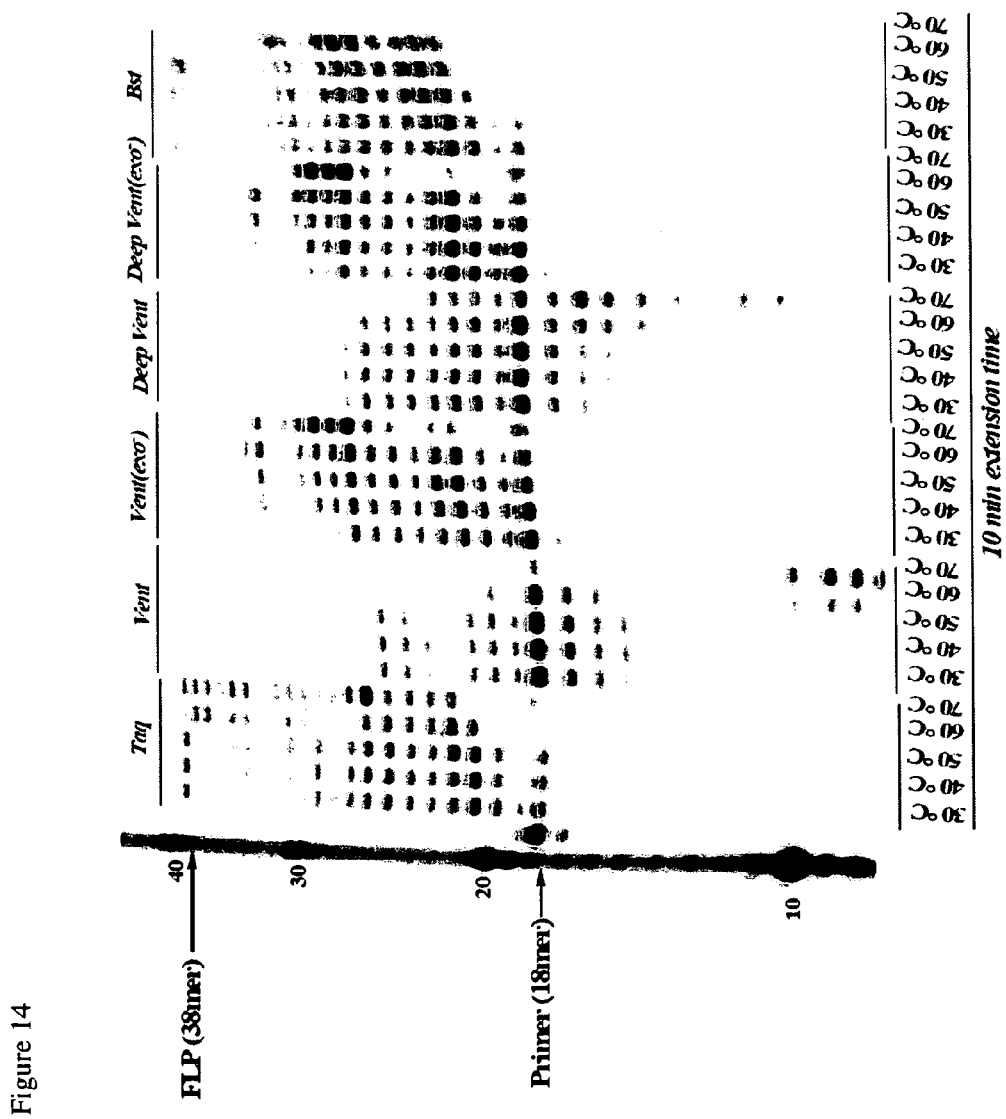

FIG. 14. Gel showing polymerase read-through of templates containing consecutive SAMRS components, reporting data collected in Example 15.

Figure 15:
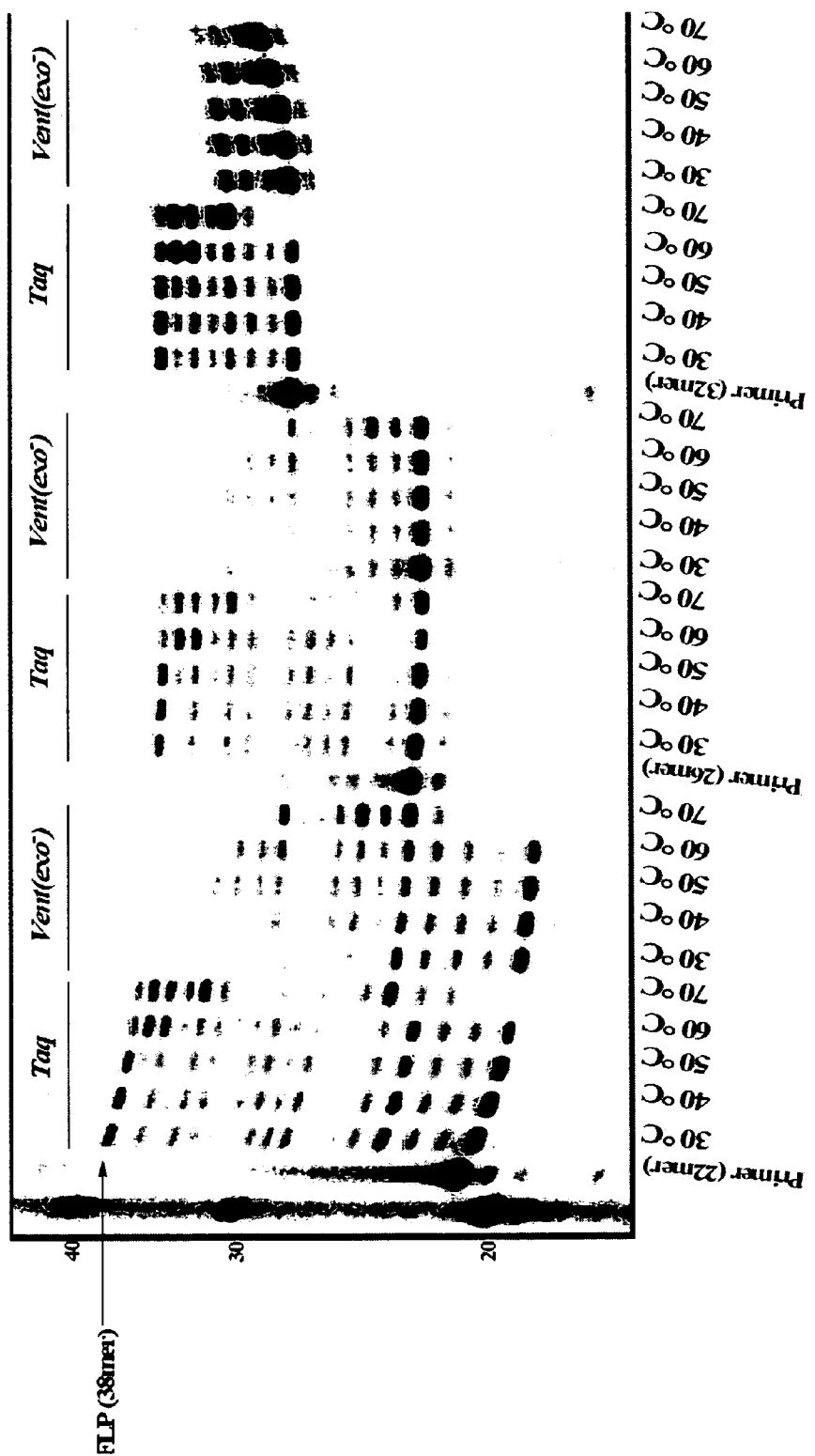

FIG. 15. Gel showing read through of thioT in templates, reporting data collected in Example 16.

Figure 16:
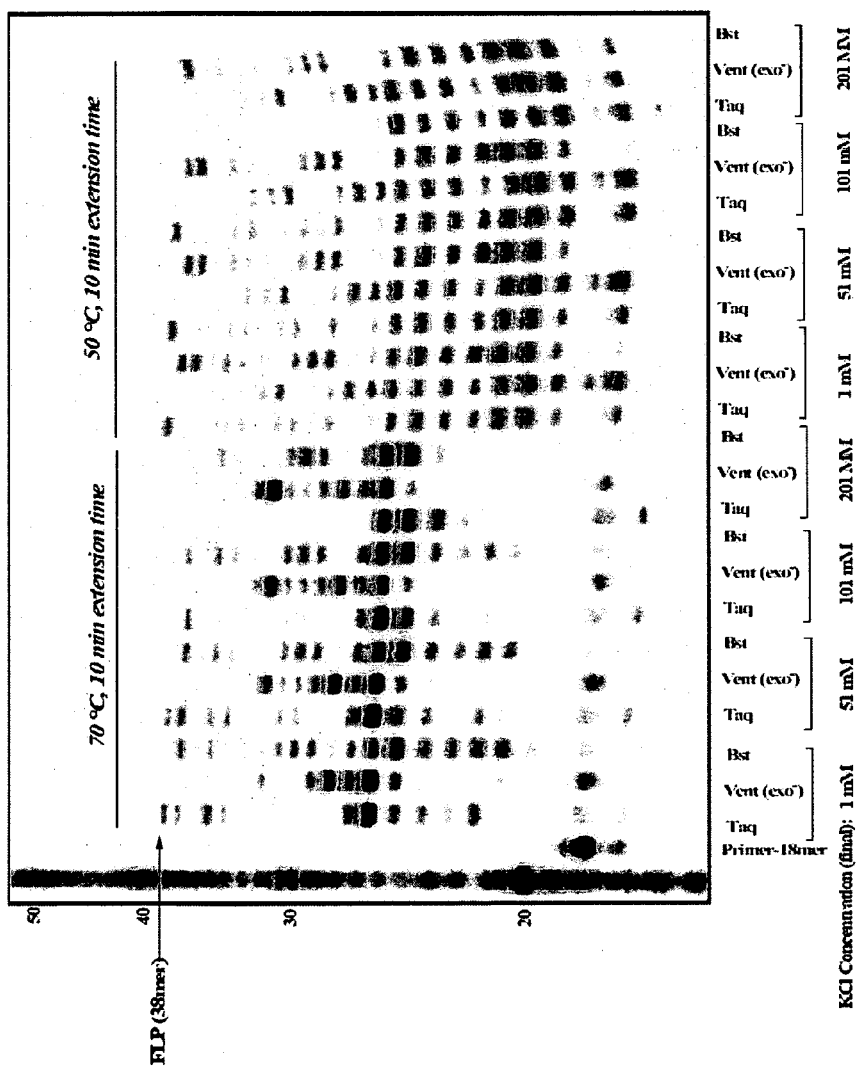

FIG. 16. Gel showing read through by DNA polymerase of SAMRS in templates at different concentrations of KCl, reporting data collected in Example 17.

DESCRIPTION OF THE INSTANT INVENTION

As with the AEGIS system, the instant invention teaches a distinction between the hydrogen bonding pattern of a SAMRS system and the heterocycle used to implement it. As is well known in the art, appendages may be attached the 5-position of pyrimidines without interfering with the hydrogen bonding that supports duplex formation. Indeed, 5-position alkyl, allyl, and acetylenic substituents at those positions generally encourage duplex formation. Likewise, substituents at this position may carry tags useful for capture (such as biotin) or detection (such as fluorescent species). The instant invention teaches that similar substituents can be attached at the "5-equivalent" position of the heterocycle that implements the SAMRS system, noting that the IUPAC numbering of the heterocycle may assign a different numbering to the 5-equivalent position of any given heterocycle.

Analogous substitutions may be placed at the 7-equivalent position of a 7-deazapurine analog that is a part of a SAMRS. Further, the 7-equivalent nitrogen may be replaced by a CH unit simply to prevent Hoogsteen binding.

Likewise, while 2'-deoxyribose is the preferred backbone when it is desired to have the SAMRS component be recognized by natural DNA polymerases, RNA polymerases, and reverse transcriptases, tighter binding is obtained by placing the SAMRS-enabling heterocycles on 2'-OMe, 2'-O-alkyl, and/or 2'-O-allyl ribose, PNA, or LNA, which are all taught here as part of the instant invention (such disclosure not being obvious without such a teaching).

Figure 4:
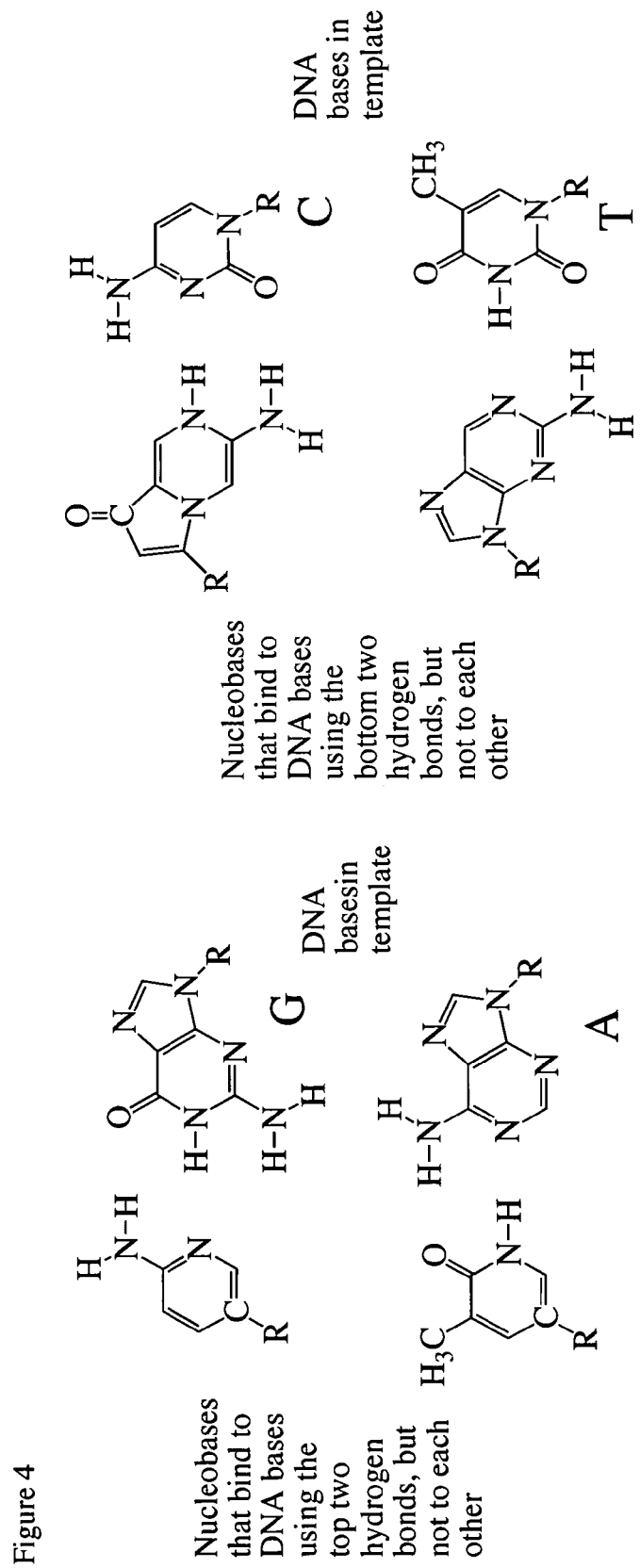
FIG. 4. Heterocycles implementing the Self-Avoiding Molecular Recognition System (SAMRS) as disclosed in U.S. Ser. Nos. 60/627,459 and 60/627,460, both filed Nov. 13, 2004, with the teaching that by using base pairs joined by two hydrogen bonds, a series of nucleobases can be designed, to be placed on a PNA or DNA backbone, that will bind to natural G, A, C, and T (by two hydrogen bonds), but not to each other (by more than one hydrogen bond). This allows the sequences in the fragments to be orthogonal to other fragment sequences.
Figure 5:
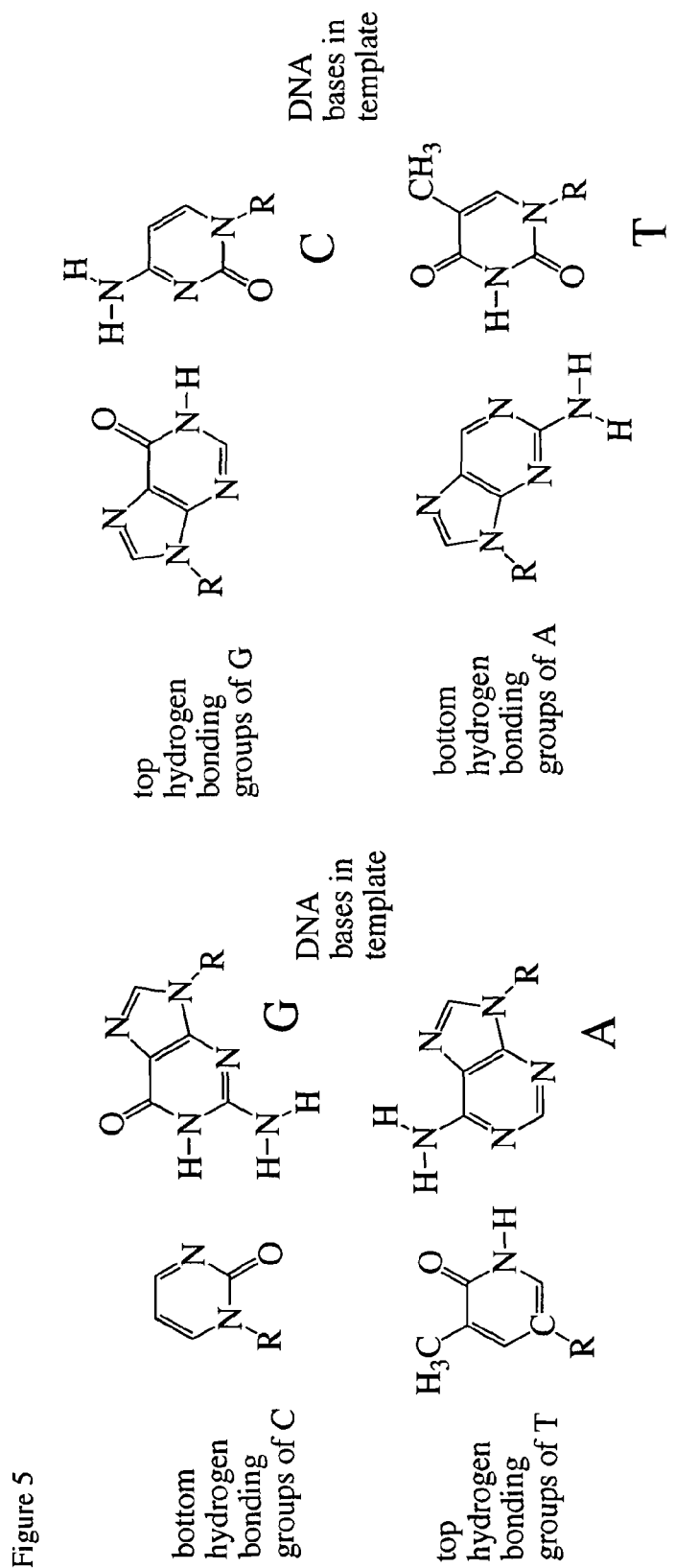
FIG. 5. Heterocycles implementing the Self-Avoiding Molecular Recognition System (SAMRS) as disclosed in U.S. Ser. No. 11/271,366, filed 2005, Nov. 12.
Figure 6:
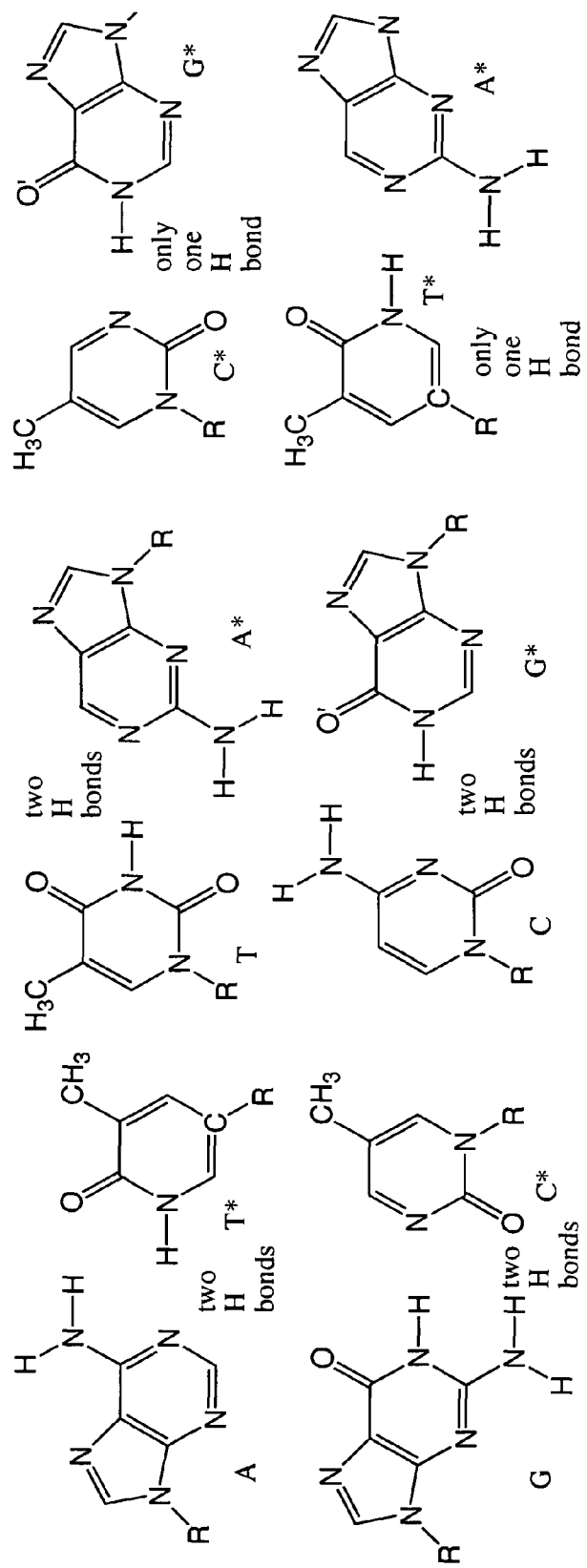
FIG. 6. Heterocycles implementing the Self-Avoiding Molecular Recognition System (SAMRS) attempted in this work, but rejected based on various issues discovered through experimentation. The C* hydrogen bonding pattern implemented with the 5-methylzebularine heterocycle proved to be too weak a binder, as well as being problematic in chemical synthesis. The T* hydrogen bonding pattern implemented with the 3-methylpyrimidin-2-one heterocycle also proved to be inadequate as a binder.

The simplest implementation of the SAMRS system is provided by the set of structures shown in FIG. 4 or the set of structures shown in FIG. 5. The structures shown in FIG. 5 were discussed in U.S. Ser. Nos. 60/627,460 and 60/62745, so let us focus on those in FIG. 6. This is a clean implementation of the concept, with exactly two hydrogen bonds joining the * analog with the standard analog, and exactly one hydrogen bond joining the two "complementary"* analogs.

Oligonucleotides were prepared containing these, and melting temperatures were determined. Thus, known routes [Lan00][Woo03][Sil99] are available to synthesize the 2'-deoxyriboside of the T* hydrogen bonding pattern implemented on a 2-pyridone heterocycle. But the binding was weak between this implementation of T* and A. A methyl group was added to the pyridone to exploit the well-known stabilizing effect of this group on duplex stability.

The use of 2-aminopurine to implement A* was facilitated by its commercial availability as a protected phosphoramidite from Glen Research. The A* is the only heterocycle in the preferred structures that carries exocyclic functional groups that need protection for standard phosphoramidite synthesis. Alkaline conditions used to deprotect protected 2-aminopurine, as delivered by Glen Research, after its incorporation into an oligonucleotide may cause partial degradation of zebularine, which was contemplated as the heterocycle that serves as C*. Therefore, the phenoxyacetyl protecting group is was used as the protecting group.

Two choices are available to implement this strategy with respect to G* and C*. The 2'-deoxyriboside of pyrimidin-2-one (the heterocycle in zebularine) forms two hydrogen bonds with natural G leaving an uncompensated carbonyl group on G in the major groove. The alternative possibility for implementing C* is the 2'-deoxyriboside of 4-aminopyridine; this was disfavored in the presently preferred embodiment because it would leave an uncompensated amino group in the minor groove (see design rules in [Gey03]).

The 2'-deoxyriboside of pyrimidin-2-one is also known [Viv04], and is commercially available as the 5-methyl derivative from Glen Research [Sin01]. This particular implementation of C* has been incorporated into an oligonucleotide. Again, the C* implemented as zebularine failed to provide useful, even though Gamper et al. had suggested it as being useful to prevent RNA from folding [Gam04].

The selection of 5-methyl-pyrimidin-2-one as C* required that inosine be used as the implementation of G*. Inosine forms two hydrogen bonds with natural C, and leaves an uncompensated carbonyl group in the minor groove. Inosine is commercially available in multiple forms, and can be synthesized inexpensive way from the appropriate adenosine derivative through deamination. It may also be obtained as the 7-deazainosine analog.

Certain features of the structures implementing several of the * hydrogen bonding patterns (in particular, the absence of any uncompensated amino groups) were sufficiently attractive to have us seek modifications to mitigate those cases (especially C* and T*) where the C*:T and T*:A binding was poor. For example, it is standard practice to make the ribosides, or the 2'-O-methylribosides, to improve the stability of a base pair. This was tried here, and failed to provide any stabilization. Adding propynyl groups to position 5-of pyrimidines also is a common trick used to increase the stability of base pairs. A series of these were examined, but failed to improve. Considering the possibility that zebularine forms a weak pair with G because it is a "push-push" electronic system, we prepared the molecule with a 5-position methoxy group. This also did not give a SAMRS with useful predictive value, even though some oligonucleotides containing various of these * analogs did serve as primers and were adequate templates (FIG. 10). Various methylated derivatives of zebularine failed. As a subtext throughout this exploratory work was two types of instability of zebularine, including the facility with which it suffers acid-catalyzed depyrimidinylation, and the facility with which it suffers base-catalyzed Michael addition to the heterocycle.

With the failure of zebularine, 5-methylzebularine, 4-methylzebularine, and 4,5-dimethylzebularine to serve as a useful C*, we considered some exotic structures, such as the cyclopropyl, cyclobutyl, and cyclopentyl fused structures. A Mills-Nixon effect was expected to reduce the rate of glycosyl bond cleavage, as well as diminish the attack of nucleophiles in a Michael sense. However, we then discovered two papers [Ngu98][Ngu00] that suggested that N-ethylcytosine ($^{4Et}$C) might serve as a C*. These papers did not disclose $^{4Et}$C as part of a primer, and we were concerned that polymerases might reject the modification in a template. Therefore, several oligonucleotides were prepared that contained, first, $^{4Et}$C alone, and then in multiple copies, and then together with other * nucleotides. Experimental conditions were found where these oligonucleotides were extended as primers by DNA polymerases, and where these primers supported PCR amplification.

Further, we fell back on previous work [Sis05] that used 2-thiothymidine, a clash between its C=S unit and a NH$_2$ unit on its complement, and the absence of a third hydrogen bonding group on natural A, to implement the T* hydrogen bonding property. That clash prevents a good 2-thiothymidine:2-aminopurine pair. This was also used (also with diaminopurine) in U.S. Pat. No. 5,912,340 and subsequent work.

Figure 7:
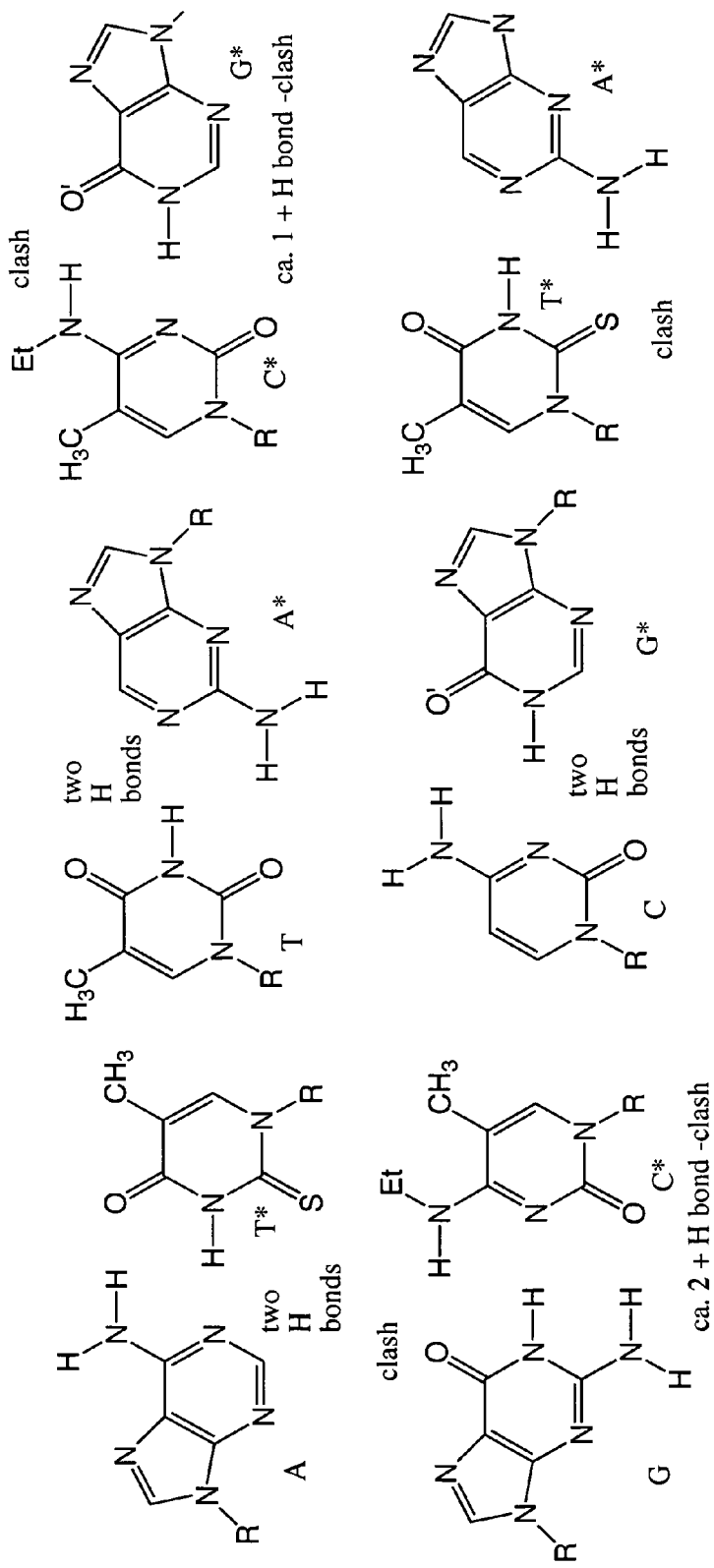
FIG. 7. Self-Avoiding Molecular Recognition System (SAMRS) in their presently preferred implementation. A molecular recognition system that binds to complementary natural DNA, but not to complementary SAMRS sequences. The pairing of each of the complements of the SAMRS heterocycles (denoted by an asterisk *) with a standard nucleobase is joined by two hydrogen bonds, while pairs between any two size-complementary SAMRS components are joined by (at most) one hydrogen bond. Note that the G*-C* and A*-T* pairs in the wobble structure do not have two productive hydrogen bonds. In developing the SAMRS concept, rules for non standard nucleobase design determined in the Benner laboratory were exploited [Gey03]. Thus, none of the nucleobases pairs have uncompensated amino group in either of the grooves, having a negative charge, and are antiaromatic.

This experimentation led to the presently preferred set of components of a SAMRS system (FIG. 7), and rules that allow one of ordinary skill in the art to design primers that target a preselected DNA sequence with useful affinity. Reference is made to the many melting temperature data reported in the Examples below. Specifically, the preselected DNA sequence is written on paper in the 5'-to-3' direction. Then, in a complementary SAMRS sequence written in an antiparallel direction, a 2-thiothymine against every A in the preselected sequence, a 2-aminopurine against every T in the preselected sequence, an N$^4$-ethylcytosine C* against every G in the preselected sequence, and a hypoxanthine against every C in the preselected sequence. As the melting temperatures in the Examples show, this set of implementation has useful predictive value.

This reduction to practive then discovered another unexpected phenomenon. While it had long been known that base pairs joined by two hydrogen bonds contributed less to duplex stability than base pairs joined by three hydrogen bonds, we were surprised to see that the melting temperatures of duplexes supported by only base pairs joined by two hydrogen bonds were abnormally low. Thus, while the 2-thioT:A pair was modestly more stable on average (with the metric being a higher Tm in a variety of contexts) than the T:A pair, a fact well known in the literature, and the I:C pair was significantly less stable than the G:C pair (a fact also well known), duplexes joined by only 2-thioT:A, 2-AP:T, I:C, and $^{4Et}$C:G pairs were significantly less stable than expected.

This had an impact on priming. Thus, even very short standard DNA nucleotides were found in the SNAP2 architecture to serve as primers when they were joined to a template by a mixture of A:T, T:A, C:G, and G:C pairs. Depending on the polymerase, the standard primer could be as short as 8 nucleotides in length, although the polymerase was presumably helping the short primers bind. In contrast, primers built entirely from SAMRS components (except for the 3'-nucleotide, which was generally a standard nucleotide so that commercial glass supports could be used to start the synthesis) could not be reliably expected to prime if it was shorter than ca. 15 nucleotides.

This is not necessarily problematic, as a 16 mer is (on average) unique in the human genome. However, priming with shorter nucleotides was certainly desired for the SNAP2 architecture. Ser. Nos. 60/627,460, 60/62745, 11/271,366 and 11/647,609 (the predecessors of the instant application) had taught that a mixture of standard and SAMRS nucleobases was preferred, for this reason. U.S. Pat. No. 5,912,340 also taught this, but for a different reason (teaching that "a sufficient number of the modified" nucleotides should be incorporated to disrupt the binding of a pair of nucleotides).

These considerations prompted the thought that to avoid primer-primer interactions in multiplexed priming or multiplexed PCR applications, it might be useful to have the self-avoiding property at the 3'-end of the primer more than at the 5'-end of the primer, as it is overlap of the 3'-ends of primers in primer libraries that causes primer-primer interactions that defeat the PCR analysis. Thus, this would direct one of ordinary skill in the art to place standard nucleobases at the 5'-end.

This selection is illustrated in the Examples. Adding to the rules above, the process of "writing and matching" will provide a useful primer composed entirely of SAMRS components for oligonucleotides 20 nucleotide units and longer. However, the preferred primer is a chimera. Starting at the 5'-end, the primer is preferred to have 5 to 20 standard nucleotides followed by from 5 to 15 SAMRS nucleotides, more preferably with the last nucleotide being standard (not for binding or priming, but rather to allow the synthesis to be done on less expensive standard controlled pore glass), and most preferably with 12-18 standard nucleotides followed by 6-10 SAMRS nucleotides followed by one standard nucleotide.

In summary, the instant invention is based on a number of discoveries, including:

(a) The ability of polymerases to accept as primers oligonucleotides containing only SAMRS nucleobases (including cases where the 3-end is not a SAMRS nucleobase), if the oligonucleotide is at least 10 nucleotides long, more preferably 15 nucleotides long, and most preferably longer than 15 nucleotides.

(b) The ability of DNA polymerases to perform PCR using primers containing SAMRS nucleobases, including N-4-ethylcytosine (where we had expected the side chain to be rejected in a template), and inosine (where we had expected thermostable polymerases to reject it as a deamination product of adenosine).

(c) The demonstration that multiplexed PCR can be obtained with as many as 30 SAMRS primers (a library, where a library is defined as a mixture containing at least 10 oligonucleotides) amplifying 15 amplicons in one pot, without any effort made to optimize the primers as is normally done in multiplexed PCR of this dimension.

(d) Some heuristic rules can be transferred from DNA to SAMRS systems, while others cannot. Thus, longer SAMRS oligonucleotides have higher $T_m$ values than shorter, where increasing the length from 18 to 25 mer in the example in FIG. 6 increased the $T_m$ from 30.8 to 42.0° C. (Example 6). Likewise, increasing the concentration of salt (in Example 7 from 100 mM to 1M NaCl) increases the $T_m$. Likewise, replacing 2-aminopurine as an implementation of the A* by 2,6-diaminopurine increases $T_m$ (Example 8). Increasing the concentration of KCl decreased pausing by polymerases as they encountered SAMRS in a template (Example 17).

However, the general heuristic rule that replacing a 2'-deoxyribose as the supporting sugar by a 2'-O-methylribose does not work well with SAMRS nucleobases, and the $T_m$ scales severely downwards as all of the standard:standard base pairs are replaced with SAMRS:standard pairs.

Further, the instant invention teaches certain preferred structures for primers containing SAMRS components, including:

(d) Chimeric primers where the 5'-segment of the primer is built from standard nucleotides, while the 3'-segment of the primer is built from SAMRS nucleotides, an architecture that also supports multiplexed priming and multiplexed PCR as a library (e) The useful results are not lost if the last 3'-terminal nucleotide carries a standard nucleobase, an expedient that lowers the cost of the primers by allowing primers to be synthesized on standard controlled pore glass supports.

EXAMPLES

Example 1

Preparation of the Base-Unprotected Thiothymidine Phosphoramidite

5'-O-(4,4'-dimethoxytrityl)-2'-deoxy-2-thiothymidine (2)

To a solution of 2-thiothymidine (Berry & Associates, 1.95 g, 7.55 mmol) in anhydrous pyridine (50 mL) was added DMTrCl (2.94 g, 8.68 mmol). The mixture was stirred at room temperature for 20 h. The reaction was then quenched by addition of MeOH (10 mL) and the solvents were removed by evaporation. The residue was dissolved in AcOEt, washed with distilled water and brine, dried with anhydrous $Na_2SO_4$ and evaporated. The residue was purified on silica gel column chromatography using 67% hexane in AcOEt as the eluent to give 3.90 g of the 5'-dimethoxytritylated species (92%) as white foam.

NMR (Varian Mercury 300 MHz spectrometer): $^1$H-NMR ($CDCl_3$, 300 MHz): δ 1.45 (s, 3H); 2.25-2.34 (m, 1H); 2.59-2.67 (m, 1H); 3.36-3.41 (dd, 1H); 3.53-3.57 (dd, 1H); 3.77 (s, 6H); 4.11 (m, 1H); 4.60 (m, 1H); 6.86 (t, 1H); 6.81-7.40 (m, 13H); 7.84 (s, 1H). $^{13}$C-NMR ($CDCl_3$): δ 12.3, 41.3, 55.5, 63.2, 71.9, 86.8, 87.2, 90.1, 113.6, 116.7, 127.5, 128.3, 128.3, 130.3, 135.5, 136.9, 144.5, 159.0, 161.1, 174.3.

ESI-TOF (+) MASS: m/z [M+Na]$^+$calcd for $C_{31}H_{32}N_2O_6S$+Na: 583.1873. found: 583.1897.

5'-{O-[(4,4'-dimethoxytrityl)-2'-deoxy-2-thiothymidine]}-3'-[2-cyanoethyl bis(1-methylethyl)phosphoramidite (3)

To a solution of the 5'-dimethoxytritylated species from above (300 mg, 0.54 mmol) in anhydrous $CH_2Cl_2$ (5 mL) was added N,N-diisopropylethylamine (235 L, 1.35 mmol) followed by 2-cyanoethyl-N,N-diisopropylchlorophosphoramidite (181 μL, 0.81 mmol). The mixture was stirred at room temperature for 2 h. To the mixture was added AcOEt, washed with distilled water and brine, dried with $Na_2SO_4$ and evaporated. The residue was purified on neutral silica gel column chromatography using 33% hexane in AcOEt as the eluent to give 348 mg of 3 (85%) as white foam.

NMR (Varian Mercury 300 MHz spectrometer): $^1$H-NMR ($CDCl_3$, 300 MHz): δ 1.04-1.18 (m, 12H); 1.40 and 1.42 (each s, 3H); 2.26-2.36 (m, 1H); 2.42 and 2.63 (each t, 2H); 2.62-2.79 (m, 1H); 3.31-3.88 (m, 6H); 3.80 (s, 6H); 4.18 (m, 1H); 4.67 (m, 1H); 6.92 (m, 1H); 6.82-7.42 (m, 13H); 7.88 and 7.92 (each s, 1H); 9.36 (br s, 1H). $^{31}$P-NMR ($CDCl_3$, 121 MHz): δ (ppm, rel to external standard $H_3PO_4$=0)=149.7; 150.4.

ESI-TOF (+) MASS: m/z [M+Na]$^+$calcd for $C_{40}H_{49}N_4O_7PS$+Na: 783.2952. found: 783.2909.

High Performance Liquid Chromatography. HPLC purification of the oligonucleotides is accomplished as described below. Analytical HPLC is also used for purification of the oligonucleotides.

[System]
A) Analytical HPLC; Waters 600S Controller, Waters™ 616 Pump, Waters™ 486 Tunable Absorbance Detector
B) Preparative HPLC; Waters PrepLC System Controller, Waters PrepLC 4000 System, Waters 486 Tunable Absorbance Detector

[Column]
a) Reverse phase column; Waters Nova-Pak C18 (3.9×150 mm) for analytical HPLC, Waters Nova-Pak HR C18 (7.8× 300 mm) for preparative HPLC
b) Ion-exchange column; DIONEX DNAPac PA-100 (4×250 mm) for analytical HPLC, DIONEX DNAPac PA-100 (9×250 mm) for preparative HPLC

[Eluent]
a) Reverse phase; A buffer=25 mM TEAA (or 25 mM $NH_4OAc$), B buffer=20% MeCN in 25 mM TEAA (or 25 mM $NH_4OAc$)
b) Ion exchange; 25 mM TEAA, 200 mM NaCl, B solution=25 mM TEAA, 1M NaCl.

Example 2

Preparation of SAMRS Oligonucleotides

Phosphoramidite chemistry has made routine the synthesis of the 4" of DNA and RNA molecules having n nucleotides in a sequence. Therefore, it is not necessary to have in possession every one of those sequences to enable the practice of an invention that claims all of those sequences. Analogously, the compositions of the instant invention are prepared by phosphoramidite synthesis, where the outcome of the synthesis is not dependent on the precise order in which nucleoside phosphoramidites are added.

Oligonucleotides containing the presently preferred SAMRS components were prepared as follows:

2'-Deoxy-5'-dimethoxytritylinosine-3'-O-(3-cyanoethyl-diisopropylaminophosphoramidite) was purchased from Glen Research and dissolved in anhydrous acetonitrile to a final concentration of 0.12 M. 2'-Deoxy-5'-dimethoxytrityl-2-thiothymidine-3'-O-(3-cyanoethyl-diisopropylaminophosphoramidite), prepared as described above, was dissolved in anhydrous acetonitrile (final concentration 0.12 M). 2'-Deoxy-5'-dimethoxytrityl-$N^4$-ethylcytidine-3'-O-(3-cyanoethyl-diisopropylaminophosphoramidite) is available from Glen Research (the material used in this work was synthesized from thymidine) and also dissolved in anhydrous acetonitrile (final concentration 0.12 M). Finally, 2'-Deoxy-5'-dimethoxytrityl-2-aminopurine-3'-O-(3-cyanoethyl-diisopropylaminophosphoramidite) protected as its N-phenoxyacetyl derivative (prepared from 2'-deoxyriboside of 2-amino purine, from Berry and Associates) was dissolved in anhydrous acetonitrile (final concentration 0.12 M). Bottles containing these were installed on an Applied Biosystems 394 DNA synthesizer (Foster City, Calif.), and the synthesis was initiated on a standard controlled pore glass support with the standard nucleotide attached, as desired for the 3'-end. Coupling times were 10 min. A solution of 3% dichloroacetic acid in dichloromethane was used for 5'-detritylation. Following completion of the synthesis, the products were released by treatment with concentrated $NH_4OH$ at room temperature for 16 h. The solutions were then frozen and lyophilized. The oligonucleotides were purified on 20% PAGE containing 7 M urea.

As a comment on the synthesis, it would found that the nitrogen for $N^4$-ethylcytidine did not need protection. Further, it was found that harsher deprotection conditions led to byproducts suggestive of a substantial loss of the sulfur from 2-thioT, a problem well documented in the literature. This is why the phenoxyacetyl group was used to protect 2-aminoadenine. We suspect that the dimethylformamidine protected phosphoramidite of 2-aminopurine-5'-dimethoxytrityl-3'-deoxynucleoside should also work, and it is at this time commercially available from Glen Research.

Example 3

Melting Temperatures of Oligonucleotides Containing Various SAMRS Components, Including Those that are not Preferred Example 3(a)

To explore the melting temperatures of SAMRS systems where 5-methylzebularine implemented a C* hydrogen bonding pattern, pairs of oligonucleotides were synthesized with a single * analog at the positions indicated by X and Y. The measurements of the melting temperatures of the duplexes are done at 260 nm with 1 mL samples at a concentration of 3 µM per single strand.

```
SAMRS-Tm1:    5'-ACCAAGCXATCAAGT-3'  X = A,                      SEQ ID NO 5

SAMRS-Tm1:    5'-ACCAAGCXATCAAGT-3'  X = 2-aminopurine,          SEQ ID NO 6

SAMRS-Tm1:    5'-ACCAAGCXATCAAGT-3'  X = T,                      SEQ ID NO 7

SAMRS-Tm1:    5'-ACCAAGCXATCAAGT-3'  X = 2-thiothymine,          SEQ ID NO 8

SAMRS-Tm1:    5'-ACCAAGCXATCAAGT-3'  X = G,                      SEQ ID NO 9

SAMRS-Tm1:    5'-ACCAAGCXATCAAGT-3'  X = hypoxanthine,           SEQ ID NO 10

SAMRS-Tm1:    5'-ACCAAGCXATCAAGT-3'  X = C,                      SEQ ID NO 11

SAMRS-Tm1:    5'-ACCAAGCXATCAAGT-3'  X = 5-methyl-pyrimidin-2-one, SEQ ID NO 12

SAMRS-Tm1-C:  3'-TGGTTCGYTAGTTCA-5'  Y = A,                      SEQ ID NO 13

SAMRS-Tm1-C:  3'-TGGTTCGYTAGTTCA-5'  Y = 2-aminopurine,          SEQ ID NO 14

SAMRS-Tm1-C:  3'-TGGTTCGYTAGTTCA-5'  Y = T,                      SEQ ID NO 15

SAMRS-Tm1-C:  3'-TGGTTCGYTAGTTCA-5'  Y = 2-thiothymine,          SEQ ID NO 16

SAMRS-Tm1-C:  3'-TGGTTCGYTAGTTCA-5'  Y = G,                      SEQ ID NO 17

SAMRS-Tm1-C:  3'-TGGTTCGYTAGTTCA-5'  Y = hypoxanthine,           SEQ ID NO 18

SAMRS-Tm1-C:  3'-TGGTTCGYTAGTTCA-5'  Y = C,                      SEQ ID NO 19

SAMRS-Tm1-C:  3'-TGGTTCGYTAGTTCA-5'  Y = 5-methyl-pyrimidin-2-one, SEQ ID NO 20
```

TABLE 3.1

| X:Y | T | T* | A | A* | C | C* | G | G* |
|---|---|---|---|---|---|---|---|---|
| A  | 55.5 | 56.8 | 43.7 | 46.5 | 45.1 | 43.5 | 46.7 | 49.8 |
| A* | 54.5 | 52.0 | 46.8 | 45.5 | 48.1 | 44.0 | 45.8 | 46.8 |
| T  | 46.3 | 48.0 | 54.0 | 52.5 | 44.6 | 45.0 | 48.4 | 46.3 |
| T* | 47.0 | 50.0 | 54.0 | 50.3 | 40.9 | 41.3 | 44.6 | 45.1 |
| G  | 49.5 | 47.0 | 47.0 | 45.1 | 58.8 | 52.0 | 47.0 | 46.0 |
| G* | 48.8 | 47.0 | 50.5 | 45.1 | 54.1 | 49.3 | 46.0 | 46.3 |
| C  | 44.0 | 40.6 | 42.8 | 47.1 | 43.8 | 41.0 | 59.0 | 52.6 |
| C* | 44.0 | 42.0 | 42.0 | 43.0 | 41.1 | 39.5 | 52.0 | 47.8 |

A* = 2-aminopurine
T* = 2-thiothymine
C* = 5-methyl-pyrimidin-2-one
G* = hypoxanthine

Example 3(b)

To explore the melting temperatures of SAMRS systems where the 2'-deoxyribose sugar was replaced by 2'-OMe ribose, pairs of oligonucleotides were synthesized with a single * analog at the positions indicated by X and Y. The measurements of the melting temperatures of the duplexes are done at 260 nm with 1 mL samples at a concentration of 3 μM per single strand.

```
SAMRS-Tm1:    5'-ACCAAGCXATCAAGT-3'  X = A,                              SEQ ID NO 5
SAMRS-Tm1:    5'-ACCAAGCXATCAAGT-3'  X = 2-aminopurine,                  SEQ ID NO 6
SAMRS-Tm1:    5'-ACCAAGCXATCAAGT-3'  X = T,                              SEQ ID NO 7
SAMRS-Tm1:    5'-ACCAAGCXATCAAGT-3'  X = 2-thiothymine,                  SEQ ID NO 8
SAMRS-Tm1:    5'-ACCAAGCXATCAAGT-3'  X = G,                              SEQ ID NO 9
SAMRS-Tm1:    5'-ACCAAGCXATCAAGT-3'  X = hypoxanthine,                   SEQ ID NO 10
SAMRS-Tm1:    5'-ACCAAGCXATCAAGT-3'  X = C,                              SEQ ID NO 11
SAMRS-Tm1:    5'-ACCAAGCXATCAAGT-3'  X = 5-methyl-pyrimidin-2-one,       SEQ ID NO 12
SAMRS-Tm1-C:  3'-TGGTTCGYTAGTTCA-5'  Y = A,                              SEQ ID NO 13
SAMRS-Tm1-C:  3'-TGGTTCGYTAGTTCA-5'  Y = 2-aminopurine,                  SEQ ID NO 14
SAMRS-Tm1-C:  3'-TGGTTCGYTAGTTCA-5'  Y = T,                              SEQ ID NO 15
SAMRS-Tm1-C:  3'-TGGTTCGYTAGTTCA-5'  Y = 2-thiothymine,                  SEQ ID NO 16
SAMRS-Tm1-C:  3'-TGGTTCGYTAGTTCA-5'  Y = G,                              SEQ ID NO 17
SAMRS-Tm1-C:  3'-TGGTTCGYTAGTTCA-5'  Y = C,                              SEQ ID NO 19
SAMRS-Tm1-C:  3'-TGGTTCGYTAGTTCA-5'  Y = 2'-OMe hypoxanthine,            SEQ ID NO 21
SAMRS-Tm1-C:  3'-TGGTTCGYTAGTTCA-5'  Y = 2'-OMe 5-methyl-pyrimidin-2-one, SEQ ID NO 22
```

TABLE 3.2

| X:Y   | T    | T*   | A    | A*   | C    | OMeC* | G    | OMeG* |
|-------|------|------|------|------|------|-------|------|-------|
| A     | 55.5 | 56.8 | 43.7 | 46.5 | 45.1 | 43.0  | 46.7 | 48.3  |
| A*    | 54.5 | 52.0 | 46.8 | 45.5 | 48.1 | 44.1  | 45.8 | 46.0  |
| T     | 46.3 | 48.0 | 54.0 | 52.5 | 44.6 | 43.0  | 48.4 | 46.0  |
| T*    | 47.0 | 50.0 | 54.0 | 50.3 | 40.9 | 42.3  | 44.6 | 45.3  |
| G     | 49.5 | 47.0 | 47.0 | 45.1 | 58.8 | 51.0  | 47.0 | 44.8  |
| OMeG* | 48.0 | 47.0 | 49.0 | 46.0 | 52.8 | 49.0  | 45.1 | 44.8  |
| C     | 44.0 | 40.6 | 42.8 | 47.1 | 43.8 | 42.0  | 59.0 | 51.0  |
| OMeC* | 42.8 | 42.1 | 42.0 | 43.0 | 42.8 | 40.0  | 51.5 | 49.0  |

A* = 2-aminopurine

T* = 2-thiothymine

C* = 5-methyl-pyrimidin-2-one

G* = hypoxanthine

For comparison, in this context, the melting temperatures for the following pairs are given:

OMeC*:G* = 49.0;

C*:OMeG* = 48.0;

OMeG*:C* = 48.0;

G*:OMeC* = 48.0

Example 3(c)

To explore the melting temperatures of SAMRS systems where one of the strands was RNA and the other was DNA, pairs of oligonucleotides were synthesized with a single * analog at the positions indicated by X and Y. The measurements of the melting temperatures of the duplexes are done at 260 nm with 1 mL samples at a concentration of 3 μM per single strand.

```
SAMRS-Tm1:    5'-r(ACCAAGCXAUCAAGU)-3'  Y = A,                     SEQ ID NO 23
SAMRS-Tm1:    5'-r(ACCAAGCXAUCAAGU)-3'  Y = 2-aminopurine,         SEQ ID NO 24
SAMRS-Tm1:    5'-r(ACCAAGCXAUCAAGU)-3'  Y = T,                     SEQ ID NO 25
SAMRS-Tm1:    5'-r(ACCAAGCXAUCAAGU)-3'  Y = 2-thiothymine,         SEQ ID NO 26
SAMRS-Tm1:    5'-r(ACCAAGCXAUCAAGU)-3'  Y = G,                     SEQ ID NO 27
SAMRS-Tm1:    5'-r(ACCAAGCXAUCAAGU)-3'  Y = C,                     SEQ ID NO 28
SAMRS-Tm1:    5'-r(ACCAAGCXAUCAAGU)-3'  Y = hypoxanthine,          SEQ ID NO 29
SAMRS-Tm1:    5'-r(ACCAAGCXAUCAAGU)-3'  Y = 5-methyl-pyrimidin-2-one,  SEQ ID NO 30
SAMRS-Tm1-C:  3'-TGGTTCGYTAGTTCA-5'     Y = A,                     SEQ ID NO 13
SAMRS-Tm1-C:  3'-TGGTTCGYTAGTTCA-5'     Y = 2-aminopurine,         SEQ ID NO 14
SAMRS-Tm1-C:  3'-TGGTTCGYTAGTTCA-5'     Y = T,                     SEQ ID NO 15
SAMRS-Tm1-C:  3'-TGGTTCGYTAGTTCA-5'     Y = 2-thiothymine,         SEQ ID NO 16
SAMRS-Tm1-C:  3'-TGGTTCGYTAGTTCA-5'     Y = G,                     SEQ ID NO 17
SAMRS-Tm1-C:  3'-TGGTTCGYTAGTTCA-5'     Y = hypoxanthine,          SEQ ID NO 18
SAMRS-Tm1-C:  3'-TGGTTCGYTAGTTCA-5'     Y = C,                     SEQ ID NO 19
SAMRS-Tm1-C:  3'-TGGTTCGYTAGTTCA-5'     Y = 5-methyl-pyrimidin-2-one,  SEQ ID NO 20
```

TABLE 3.3

| X:Y | T | T* | A | A* | C | C* | G | G* |
|---|---|---|---|---|---|---|---|---|
| A | 43.8 | 45.3 | 315 | 32.5 | 34.0 | 34.0 | 32.3 | 35.0 |
| A* |  | 52.0 |  | 45.5 |  | 44.0 |  | 46.8 |
| U | 34.3 | 37.0 | 41.0 | 41.3 | 33.0 | 33.0 | 35.3 | 33.8 |
| T* |  | 50.0 |  | 50.3 |  | 41.3 |  | 45.1 |
| G | 41.3 | 36.5 | 33.0 | 33.5 | 48.3 | 43.3 | 34.8 | 35.0 |
| G* |  | 47.0 |  | 45.1 |  | 49.3 |  | 46.3 |
| C | 29.0 | 29.3 | 28.3 | 33.0 | 28.8 | 31.0 | 42.8 | 35.8 |
| C* |  | 42.0 |  | 43.0 |  | 39.5 |  | 47.8 |

A* = 2-aminopurine;

T* = 2-thiothymine;

C* = 5-methyl-pyrimidin-2-one,

G* = hypoxanthine

The Tm values of dSAMRS:dSAMRS duplex are underlined. For comparison, in this context, the melting temperatures for the following pairs are given:

A:OMeG* = 36.3,

U:OMeG* = 37.3,

G:OMeG* = 36.0,

C:OMeG* = 37.8;

A:OMeC* = 34.8,

U:OMeC* = 36.0,

G:OMeC* = 44.8,

C:OMeC* = 31.3

Example 4

Melting temperatures, primer extension, and PCR with the preferred SAMRS components Chimeric primers designed to create a PCR amplicon ca 1000 bp in length from the Taq gene. These primers had a 5'-segment built from standard nucleotides and the 3'-end built from SAMRS nucleotides (with the last 3'-nucleotide being standard to allow a lower cost of synthesis; see body of disclosure) were synthesized, and their melting temperatures were determined by UV (Cary). Conditions: 20 mM Na cacodylate (pH 7.0), 100 mM NaCl, 3 microM each oligonucleotide.

TABLE 4.1

Tm values for primers used to amplify the gene for Taq DNA polymerase

| sequence | $T_m$ (° C.) |
|---|---|
| 5'-TATCTGCGTGCCCTGTCTCTGGAGG-3' SEQ ID NO 31<br>3'-ATAGACGCACGGGACAGAGACCTCC-5' SEQ ID NO 32 | 74.0 |
| 5'-TATCTGCGTGCCCTGTCTCTG*G*A*G*G-3' SEQ ID NO 1<br>3'-ATAGACGCACGGGACAGAGAC C T C C-5' SEQ ID NO 32 | 68.8 |
| 5'-TATCTGCGTGCCCTGTC*T*C*T*G*G*A*G*G-3' SEQ ID NO 3<br>3'-ATAGACGCACGGGACAG A G A C C T C C-5' SEQ ID NO 32 | 65.0 |

A* = 2-aminopurine
T* = 2-thiothymine
C* = $N^4$-ethylcytosine
G* = hypoxanthine The PCR experiment is shown in FIG. 10. Note that the primers are deliberately designed to produce primer dimers when implemented using standard nucleotides:

```
5'-TATCTGCGTGCCCTGTCT C T G*G*A*G*G-3'
SEQ ID NO 1

3'- GA*G*A*C*C T C C ATCTCCAACCGTAACC-5'
SEQ ID NO 2
```

Accordingly, in FIG. 10, no amplicon is observed with these primers, unless they have SAMRS components. Adding SAMRS components to the 3'-end reduces, and then eliminates primer-dimer, and increases the amount of full length amplicon. This represents the first experimental demonstration of self-avoiding properties in primer extension experiments, and is therefore a key discovery that supports the patentability of the instant invention.

Example 5

Melting Temperatures with Primers Targeted Against the Human Retinoblastoma Transcript or cDNA (RET)

TABLE 5.1

$T_m$ values for the indicated primers.

| sequence | $T_m$ (° C.) |
|---|---|
| 5'-C*C*A*G*G*A*T*C*C*A*C*T*G*T*G*C*G*A*C*G*A*G*C*T*G-3'<br>SEQ ID NO 33 | 40.3 |
| 3'-GGTCCTAGGTGACACGCTGCTCGAC-5'<br>SEQ ID NO 34 | |
| 5'-CGCACGGTGATCGCAGCCGCTGTCC-3'<br>SEQ ID NO 35 | 44.0 |
| 3'-G C*G*T*G*C*C*A*C*T*A*G*C*G*T*C*G*G*C*G*A*C*A*G*G*-5'<br>SEQ ID NO 36 | |
| 5'-CCA*GGA*T*CCA*CT*GT*GCGA*CGA*GCT*G-3' SEQ ID NO 37 | 74.8 |
| 3'-GGT CCT A GGT GA CA CGCT GCT CGA C-5' SEQ ID NO 34 | |
| 5'-CGCA CGGT GA T CGCA GCCGCT GT CC-3' SEQ ID NO 35 | 80.3 |
| 3'-GCGT*GCCA*CT*A*GCGT*CGGCGA*CA*GG-5' SEQ ID NO 38 | |
| 5'-CCAGGATCCACTGTGCG*A*C*G*A*G*C*T*G-3' SEQ ID NO 39 | 62.3 |

TABLE 5.1-continued

T_m values for the indicated primers.

| sequence | T_m (° C.) |
|---|---|
| 3'-GGTCCTAGGTGACACGCTGCTCGAC-5' SEQ ID NO 34 | |
| 5'-CGCACGGTGATCGCAGCCGCTGTCC-3' SEQ ID NO 35 | 705 |
| 3'-GC*G*T*G*C*C*A*C*TAGCGTCGGCGACAGG-5' SEQ ID NO 40 | |
| 5'-CCAGGATCCACTGTGCGACGA*G*C*T*G -3' SEQ ID NO 41 | 72.0 |
| 3'-GGTCCTAGGTGACACGCTGCT C G A C -5' SEQ ID NO 34 | |
| 5'-CG C A C GGTGATCGCAGCCGCTGTCC-3' SEQ ID NO 35 | 75.7 |
| 3'-GC*G*T*G*CCACTAGCGTCGGCGACAGG-5' SEQ ID NO 42 | |

These data show that a duplex joined entirely by SAMRS: standard base pairs has a lower than the expected melting temperature.

Example 6

Melting Temperatures with Primers Targeted Against Taq and the Human Retinoblastoma Transcript (RET) as a Function of Length To compare the melting temperatures of the all-SAMRS oligonucleotides (except for the very last nucleotide at the 3'-end, which is a standard nucleotide) for comparison with the chimeric species having the same sequence (see Table 4.1), the indicated oligonucleotides were prepared, and the melting temperatures were determined. Conditions: 20 mM Na cacodylate (pH 7.0), 100 mM NaCl, 3 microM oligonucleotides. n.d. means that any transition was not observed over 15° C. (T_m would be lower than 15° C.).

TABLE 6.1

| sequence | T_m (° C.) |
|---|---|
| T_m values for Taq gene primers having different lengths | |
| 5'-TGCCCTGTCTCTGGAGGT-3' SEQ ID NO 43 | 66.0 |
| 3'-ACGGGACAGAGACCTCCA-5' SEQ ID NO 44 | |
| 5'-T*G*C*C*C*T*G*T*C*T*C*T*G*G*A*G*G*T-3' SEQ ID NO 45 | 30.8 |
| 3'-A C G G G A C A G A G A C C T C C A-5' SEQ ID NO 44 | |
| 5'-T G C C C T G T C T C T G G A G G T-3' SEQ ID NO 43 | 26.0 |
| 3'-A C*G*G*G*A*C*A*G*A*G*A*C*C*T*C*C*A*-5' SEQ ID NO 46 | |
| 5'-T*G*C*C*C*T*G*T*C*T*C*T*G*G*A*G*G*T-3' SEQ ID NO 45 | n.d. |
| 3'-A C*G*G*G*A*C*A*G*A*G*A*C*C*T*C*C*A*-5' SEQ ID NO 46 | |
| 5'-TATCTGCGTGCCCTGTCTCTGGAGG-3' SEQ ID NO 31 | 74.0 |
| 3'-ATAGACGCACGGGACAGAGACCTCC-5' SEQ ID NO 32 | |
| 5'-T*A*T*C*T*G*C*G*T*G*C*C*C*T*G*T*C*T*C*T*G*G*A*G*G-3' SEQ ID NO 47 | 42.0 |
| 3'-A T A G A C G C A C G G G A C A G A G A C C T C C-5' SEQ ID NO 32 | |
| 5'-T A T C T G C G T G C C C T G T C T C T G G A G G-3' SEQ ID NO 31 | not meas. |
| 3'-A T*A*G*A*C*G*C*A*C*G*G*G*A*C*A*G*A*G*A*C*C*T*C*C*-5' SEQ ID NO 48 | |

TABLE 6.1-continued

| sequence | $T_m$ (° C.) |
|---|---|
| 5'-T*A*T*C*T*G*C*G*T*G*C*C*C*T*G*T*C*T*C*T*G*G*A*G-3' SEQ ID NO 47 | not meas |
| 3'-A T*A*G*A*C*G*C*A*C*G*G*A*C*A*G*A*G*A*C*C*T*C*C-5' SEQ ID NO 48 | |

Tm values for RET transcript primers.

| 5'-C*C*A*G*G*A*T*C*C*A*C*T*G*T*G*C*G*A*C*G*A*G*C*T*G-3' SEQ ID NO 33 | 40.3 |
| 3'-G G T C C T A G G T G A C A C G C T G C T C G A C-5' SEQ ID NO 34 | |
| 5'-C G C A C G G T G A T C G C A G C C G C T G T C C-3' SEQ ID NO 35 | 44.0 |
| 3'-G C*G*T*G*C*C*A*C*T*A*G*C*G*T*C*G*G*C*G*A*C*A*G*G*-5' SEQ ID NO 36 | |

A* = 2-aminopurine
T* = 2-thiothymine
C* = N⁴-ethylcytosine
G* = hypoxanthine

The heuristic rules that are extracted from the data produced in this example is that with all-SAMRS oligonucleotides, Example 7

Melting Temperatures with Primers Targeted Against Taq as a Function of Salt Concentration To compare the melting temperatures of the all-SAMRS oligonucleotides (except for the very last nucleotide at the 3'-end, which is a standard nucleotide) at different concentrations of salt, the indicated oligonucleotides were prepared, and the melting temperatures were determined. Conditions: 3 microM oligonucleotides. n.d. means that any transition was not observed over 15° C. ($T_m$ would be lower than 15° C.). The Tm values were higher in higher salt concentration (1M NaCl).

TABLE 7

| sequence | Tm (° C.) |
|---|---|
| Melting temperature of 18mer pairs in low salt. | |
| 5'-TGCCCTGTCTCTGGAGGT-3' SEQ ID NO 43 | 66.0 |
| 3'-ACGGGACAGAGACCTCCA-5' SEQ ID NO 44 | |
| 5'-T*G*C*C*C*T*G*T*C*T*C*T*G*G*A*G*G*T-3' SEQ ID NO 45 | 30.8 |
| 3'-A C G G G A C A G A G A C C T C C A-5' SEQ ID NO 44 | |
| 5'-T G C C C T G T C T C T G G A G G T-3' SEQ ID NO 43 | 26.0 |
| 3'-A C*G*G*G*A*C*A*G*A*G*A*C*C*T*C*C*A*-5' SEQ ID NO 46 | |
| 5'-T*G*C*C*C*T*G*T*C*T*C*T*G*G*A*G*G*T-3' SEQ ID NO 45 | n.d. |

TABLE 7-continued

| sequence | Tm (° C.) |
|---|---|
| 3'-A C*G*G*G*A*C*A*G*A*G*A*C*C*T*C*C*A*-5' SEQ ID NO 46 | |
| Conditions (low salt): 20 mM Na cacodylate (pH 7.0), 100 mM NaCl. | |
| Melting temperature of 18mer pairs in high salt. | |
| 5'-TGCCCTGTCTCTGGAGGT-3' SEQ ID NO 43 | 74.0 |
| 3'-ACGGGACAGAGACCTCCA-5' SEQ ID NO 44 | |
| 5'-T*G*C*C*C*T*G*T*C*T*C*T*G*G*A*G*G*T-3' SEQ ID NO 45 | 36.0 |
| 3'-A C G G G A C A G A G A C C T C C A-5' SEQ ID NO 44 | |
| 5'-T G C C C T G T C T C T G G A G G T-3' SEQ ID NO 43 | 30.5 |
| 3'-A C*G*G*G*A*C*A*G*A*G*A*C*C*T*C*C*A*-5' SEQ ID NO 46 | |
| 5'-T*G*C*C*C*T*G*T*C*T*C*T*G*G*A*G*G*T-3' SEQ ID NO 45 | n.d. |
| 3'-A C*G*G*G*A*C*A*G*A*G*A*C*C*T*C*C*A*-5' SEQ ID NO 46 | |
| Conditions (high salt): no 0 Na cacodylate (pH 7.0), 1 M NaCl. | |

A* = 2-aminopurine
T* = 2-thiothymine
C* = N⁴-ethylcytosine
G* = hypoxanthine

Example 8

Melting Temperatures with Primers Targeted Against Taq as a Function of Salt Concentration To compare the melting temperatures of oligonucleotides (with a single SAMRS pair embedded in a 15 mer, with 2,6-diaminopurine replacing 2-amino purine as the implementation of A*, the indicated oligonucleotides were prepared, and their melting temperatures were determined. Conditions: 20 mM Na cacodylate (pH 7.0), 100 mM NaCl, 3 microM oligonucleotides. n.d. means that any transition was not observed over 15° C. ($T_m$ would be lower than 15° C.). The Tm values were higher in higher salt concentration (1M NaCl).

```
SAMRS-Tm1: 5'-ACCAAGCXATCAAGT-3'
X = adenine SEQ ID NO 5

SAMRS-Tm1: 5'-ACCAAGCXATCAAGT-3'
X = 2-aminopurine SEQ ID NO 6

SAMRS-Tm1: 5'-ACCAAGCXATCAAGT-3'
X = 2-aminoadenine SEQ ID NO 117

SAMRS-Tm1-C: 3'-TGGTTCGYTAGTTCA-5'
Y = T SEQ ID NO 15

SAMRS-Tm1-C: 3'-TGGTTCGYTAGTTCA-5'
Y = 2-aminopurine SEQ ID NO 13

SAMRS-Tm1-C: 3'-TGGTTCGYTAGTTCA-5'
Y = X = 2-aminoadenine SEQ ID NO 118
A* = 2-aminopurine
DAP = 2,6-diaminopurine
T* = 2-thiothymine
```

TABLE 8.1

Melting temperature comparison of 2-aminopurine and 2,6-diaminopurine

| X:Y | $T_m$ (° C.) | $\Delta T_m$ (° C.) | X:Y | $T_m$ (° C.) | $\Delta T_m$ (° C.) |
|---|---|---|---|---|---|
| A:T | 55.5 | — | A:T* | 56.8 | +1.3 |
| A*:T | 54.5 | −1.0 | A*:T* | 52.0 | −2.5, −4.8 |
| DAP:T | 57.3 | +1.8 | DAP:T* | 52.3 | −5.0, −4.5 |
| T:A | 54.0 | — | T*:A | 54.0 | ±0 |
| T:A* | 52.5 | −1.5 | T*:A* | 50.3 | −2.2, −3.7 |
| T:DAP | 56.5 | +1.0 | T*:DAP | 50.8 | −5.7, −3.2 |

Example 9

Examination of Melting Temperatures of 2-Methylhypoxanthine (2MeI) Alternative for Hypoxanthine as a G*, and N4-Ethylcytosine as an Implementation of C*

The indicated oligonucleotides were prepared and the melting temperatures were determined. Conditions: 20 mM Na cacodylate (pH 7.0), 100 mM NaCl, 3 microM oligonucleotides. n.d. means that any transition was not observed over 15° C. (Tm would be lower than 15° C.).

```
5'-ACCAAGCXATCAAGT-3'
X = cytosine, SEQ ID NO 11

5'-ACCAAGCXATCAAGT-3'
X = hypoxanthine, SEQ ID NO 10

5'-ACCAAGCXATCAAGT-3'
X = 2-methylhypoxanthine, SEQ ID NO 119

3'-TGGTTCGYTAGTTCA-5'
Y = thymine SEQ ID NO 15

3'-TGGTTCGYTAGTTCA-5'
Y = 2-aminopurine SEQ ID NO 13

3'-TGGTTCGYTAGTTCA-5'
Y = X = 2-methylhypoxanthine, SEQ ID NO 120
```

| X:Y | $T_m$ (° C.) | $\Delta T_m$ (° C.) | X:Y | $T_m$ (° C.) | $\Delta T_m$ (° C.) |
|---|---|---|---|---|---|
| G*:C | 54.1 | — | G*:N4eU | 52.0 | −2.1 |
| 2MeI:C | 51.3 | — | 2MeI:N4eU | 48.0 | −3.3 |
| C:G* | 52.6 | — | N4eU:G* | 51.5 | −1.1 |
| C:2MeI | 49.0 | — | N4eU:2MeI | 46.0 | −3.0 |

Conditions: 20 mM Na cacodylate (pH 7.0), 100 mM NaCl, 3 μM each oligonucleotide. 2 MeI represents 2-Me-inosine.

Example 10

Examination of Melting Temperatures with N4-Ethylcytosine (N4eU) as an Implementation of C*

The indicated oligonucleotides were prepared and the melting temperatures were determined. Conditions: 20 mM Na cacodylate (pH 7.0), 100 mM NaCl, 3 microM oligonucleotides. n.d. means that any transition was not observed over 15° C. (Tm would be lower than 15° C.).

```
5'-ACCAAGCXATCAAGT-3'
X = a, SEQ ID NO 5

5'-ACCAAGCXATCAAGT-3'
X = t, SEQ ID NO 7

5'-ACCAAGCXATCAAGT-3'
X = g, SEQ ID NO 9

5'-ACCAAGCXATCAAGT-3'
X = c, SEQ ID NO 11

5'-ACCAAGCXATCAAGT-3'
X = N4-ethylcytosine,
N4eU, SEQ ID NO 121

3'-TGGTTCGYTAGTTCA-5'
Y = a SEQ ID NO 13

3'-TGGTTCGYTAGTTCA-5'
Y = t SEQ ID NO 15

3'-TGGTTCGYTAGTTCA-5'
Y = g SEQ ID NO 17

3'-TGGTTCGYTAGTTCA-5'
Y = c SEQ ID NO 19

3'-TGGTTCGYTAGTTCA-5'
Y = N4-ethylcytosine,
N4eU, SEQ ID NO 114
```

TABLE 10.1

| X:Y | $T_m$ (° C.) | $\Delta T_m$ (° C.) | X:Y | $T_m$ (° C.) | $\Delta T_m$ (° C.) |
|---|---|---|---|---|---|
| A:N4eU | 45.3 | −10.4 | A*:N4eU | 46.8 | −8.9 |
| T:N4eU | 41.6 | −14.1 | T*:N4eU | 40.3 | −15.4 |
| G:N4eU | 55.7 | — | G*:N4eU | 52.0 | −3.7 |
| C:N4eU | 42.0 | −13.7 | N4eU:N4eU | 40.8 | −14.9 |

| X:Y | $T_m$ (° C.) | $\Delta T_m$ (° C.) | X:Y | $T_m$ (° C.) | $\Delta T_m$ (° C.) |
|---|---|---|---|---|---|
| N4eU:A | 43.0 | −12.8 | N4eU:A* | 45.0 | −10.8 |
| N4eU:T | 41.8 | −14.0 | N4eU:T* | 40.0 | −15.8 |
| N4eU:G | 55.8 | — | N4eU:G* | 51.5 | −4.3 |
| N4eU:C | 41.8 | −14.0 | N4eU:N4eU | 40.8 | −15.0 |

Example 11

Examination of Melting Temperatures with Mixed Sequences with Non-Preferred Implementation of C*

The indicated oligonucleotides were prepared and the melting temperatures were determined. Conditions: 20 mM Na cacodylate (pH 7.0), 100 mM NaCl, 3 microM oligonucleotides. n.d. means that any transition was not observed over 15° C. (Tm would be lower than 15° C.).

TABLE 11.1

Melting temperatures with mixed sequences. C* and eC represent (5-methyl-pyrimidinone) and N4-ethyl-C, respectively.

| sequence | $T_m$ (° C.) | $\Delta T_m$ (° C.) |
|---|---|---|
| 5'-TGCCCTGTCTCTGGAGGT-3' SEQ ID NO 43 | 66.0 | |
| 3'-ACGGGACAGAGACCTCCA-5' SEQ ID NO 44 | | |
| 5'-TATTTTATTTTTAAAAAT-3' SEQ ID NO 49 | 39.1 | |
| 3'-ATAAAATAAAAATTTTTA-5' SEQ ID NO 50 | | |
| 5'-TGC C C TGTC TC TGGAGGT-3' SEQ ID NO 43 | 50.4 | -15.6 |
| 3'-ACG*G*G*ACAG*AG*ACCTCCA-5' SEQ ID NO 55 | | |
| 5'-TGC*C*C*TGTC*TC*TGGAGGT-3' SEQ ID NO 51 | 37.3 | -28.7 |
| 3'-ACG G G ACAG AG ACCTCCA-5' SEQ ID NO 44 | | |
| 5'-TGC*C*C*TGTC*TC*TGGAGGT-3' SEQ ID NO 51 | 26.0 | -40.0 |
| 3'-ACG*G*G*ACAG*AG*ACCTCCA-5' SEQ ID NO 55 | | |
| 5'-TGeCeCeCTGTeCTeCTGGAGGT-3' SEQ ID NO 52 | 55.2 | -10.8 |
| 3'-AC G G GACA GA GACCTCCA-5' SEQ ID NO 44 | | |
| 5'-TGeCeCeCTGTeCTeCTGGAGGT-3' SEQ ID NO 52 | 40.0 | -26.0 |
| 3'-ACG*G*G*ACAG*AG*ACCTCCA-5' SEQ ID NO 55 | | |

A* = 2-aminopurine
T* = 2-thiothymine
C* = 5-methyl-pyrimidin-2-one
G* = hypoxanthine

Example 12

Examination of Melting Temperatures with Mixed Sequences with Non-Preferred Implementation of C*

The indicated oligonucleotides were prepared and the melting temperatures were determined. Conditions: 20 mM Na cacodylate (pH 7.0), 100 mM NaCl, 3 microM oligonucleotides. n.d. means that any transition was not observed over 15° C. (Tm would be lower than 15° C.).

5'-ACCAAGCXATCAAGT-3'
X = a, SEQ ID NO 5

5'-ACCAAGCXATCAAGT-3'
X = t, SEQ ID NO 7

5'-ACCAAGCXATCAAGT-3'
X = g, SEQ ID NO 9

5'-ACCAAGCXATCAAGT-3'
X = c, SEQ ID NO 11

5'-ACCAAGCXATCAAGT-3'
X = h, SEQ ID NO 10

5'-ACCAAGCXATCAAGT-3'
X = 4-methylpyrimidin-2-one, 4mC*, SEQ ID NO 122

5'-ACCAAGCXATCAAGT-3'
X = N4-methylcytosine, N4mU, SEQ ID NO 123

5'-ACCAAGCXATCAAGT-3'
X = N4-methyl-5-methylcytosine, N4mT, SEQ ID NO 124

3'-TGGTTCGYTAGTTCA-5'
Y = a SEQ ID NO 13

3'-TGGTTCGYTAGTTCA-5'
Y = t SEQ ID NO 15

3'-TGGTTCGYTAGTTCA-5'
Y = g SEQ ID NO 17

3'-TGGTTCGYTAGTTCA-5'
Y = c SEQ ID NO 19

3'-TGGTTCGYTAGTTCA-5'
Y = h SEQ ID NO 18

3'-TGGTTCGYTAGTTCA-5'
Y = 4-methylpyrimidin-2-one, 4mC*, SEQ ID NO 111

3'-TGGTTCGYTAGTTCA-5'
Y = N4-methylcytosine, N4mU, SEQ ID NO 113

3'-TGGTTCGYTAGTTCA-5'
Y = N4-methyl-5-methylcytosine, N4mT, SEQ ID NO 115

TABLE 12.1

Melting temperatures with mixed sequences with various implementations of C* (see FIG. 11 for abbreviations).

| X:Y | $T_m$ (° C.) | $\Delta T_m$ (° C.) | X:Y | $T_m$ (° C.) | $\Delta T_m$ (° C.) |
|---|---|---|---|---|---|
| G:C | 58.8 | — | G:C* | 52.0 | -6.8 |
| G:4mC* | | | G:45dmC* | 51.0 | -7.8 |
| G:N4mU | 57.0 | -1.8 | G:N4eU | 55.7 | -3.1 |
| G:N4mT | 46.5 | -12.3 | G:N4eT | | |
| G*:C | 54.1 | — | G*:C* | 49.3 | -4.8 |
| G*:4mC* | | | G*:45dmC* | 49.8 | -4.3 |
| G*:N4mU | 53.8 | -0.3 | G*:N4eU | 52.0 | -2.1 |
| G*:N4mT | 45.8 | -8.3 | G*:N4eT | | |
| A:T | 55.5 | — | | | |

| X:Y | $T_m$ (° C.) | $\Delta T_m$ (° C.) | X:Y | $T_m$ (° C.) | $\Delta T_m$ (° C.) |
|---|---|---|---|---|---|
| C:G | 59.0 | — | C*:G | 52.0 | -7.0 |
| 4mC*:G | | | 45dmC*:G | | |
| N4mU:G | 56.3 | -2.7 | N4eU:G | 55.8 | -3.2 |

TABLE 12.1-continued

Melting temperatures with mixed sequences with various implementations of C* (see FIG. 11 for abbreviations).

| N4mT:G | 45.8 | −13.2 | N4eT:G | | |
|---|---|---|---|---|---|
| C:G* | 52.6 | — | C*:G* | 47.8 | −4.8 |
| 4mC*:G* | | | 45dmC*:G* | | |
| N4mU:G* | 51.3 | −1.3 | N4eU:G* | 51.5 | −1.1 |
| N4mT:G* | 45.5 | −7.1 | N4eT:G* | | |
| T:A | 54.0 | — | | | |

These results show as heuristic rules that the N4-Et-C:G pair has almost same stability as T:A pair [Ngu00], while the N4-Et-C seems to prefer G to G* (55.7 vs. 52.0 and 55.8 vs. 51.5). G*=inosine.

Example 13

Primer Extensions Using Primers Containing Scattered SAMRS Components (FIG. 12) Correct Procedure The 5-methyl zebularine derivative (where the heterocycle implementing a C* hydrogen bonding pattern is 5-methylpyrimidin-2-one) was found to perform sufficiently well that polymerases were sought that accept it and other SAMRS analogs in primers and templates. This example shows that the following set of SAMRS implementations are acceptable, to a level, with a heuristic rule that T*>A*>*C*>G*, in order from easy to difficult. See FIG. 12.

```
Templates:

Template 1: 3'-ACGGGACAGAGACCTCCAACGACTTCTTTAGCGCGCAG 5'  SEQ ID NO 60

Template 2: 5'-CTGGATGTTGCATATCTGCGTGCCCTGTCTCTGGAGGT 3'  SEQ ID NO 61

Reverse Primer 1: 3'GACTTCTTTAGCGCGCAG 5'  SEQ ID NO 62

Reverse Primer 2: 5'CTGGATGTTGCATATCTG 3'  SEQ ID NO 63
                             Forward Primer:
                                 C-Series:

C1-A*: 3'-A CGGGA*CA*GA*GA*CCTCCA*-5'  SEQ ID NO 64

C-ST: 3'-ACGGGACAGAGACCT*CCA-5'  SEQ ID NO 65

C-C*: 3'-AC*GGGAC*AGAGAC*C*TC*C*A-5'  SEQ ID NO 66

C-G*: 3'-ACG*G*G*ACA G*AG*ACCTCCA-5'  SEQ ID NO 55

GC-C1: 3'-AC*G*G*G*AC*AG*AG*AC*C*TC*C*A-5'  SEQ ID NO 67
                                 P-Series:

P-A*: 5'-TGCCCTGTCTCTGGA*GGT-3'  SEQ ID NO 68

P-ST: 5'-T*GCCCT*GT*CT*CT*GGAGGT-3'  SEQ ID NO 69

P-C*: 5'-TGC*C*C*TGTC*TC*TGGAGGT-3'  SEQ ID NO 52

P-G*: 5'-TG*CCCTG*TCTCTG*G*AG*G*T-3'  SEQ ID NO 70

GC-P1: 5'-TG*C*C*C*TG*TC*TC*TG*G*AG*G*T-3'  SEQ ID NO 71
                           Template/Primer complex:

P-Series: 5'TGCCCTGTCTCTGGAGGT-3'  SEQ ID NO 72

Template 1: 3' ACGGGACAGAGACCTCCAACGACTTCTTTAGCGCGCAG 5'  SEQ ID NO 73

C-Series: 3'ACGGGACAGAGACCTCCA 5'  SEQ ID NO 44

Template 2: 5'-CTGGATGTTGCATATCTGCGTGCCCTGTCTCTGGAGGT-3'  SEQ ID NO 61

A* = 2-aminopurine
T* = 2-thiothymine
C* = 5-methyl-pyrimidin-2-one
G* = hypoxanthine
```

Methods: SAMRS primers (18 nt) was annealed to the complementary template (shown above) by heating (2 min) at 95° C. followed by slow cooling to 20° C. (over 20 min). Alpha-$^{32}$P-dCTP and dNTPs was then added, followed by Kenow fragment of DNA polymerase 1. Incubation was continued for various times at indicated temperatures, and quenched with 10 mM EDTA in formamide loading buffer. The resulting reaction mixtures were separated on 14% PAGE and visualized by autoradiography. The results are shown in FIG. 12.

Example 14

Primer Extensions Using Primers Containing all SAMRS Components (Except 3'-End) (FIG. 13)

A*=2-aminopurine
T*=2-thiothymine
C*=5-methyl-pyrimidin-2-one
G*=hypoxanthine

We then sought to generate data showing polymerase read-through of a template containing multiple SAMRS components,

```
Sequences:
32P SAMRS I 15mer: 5'-T*G*C*C*C*T*G*T*C*T*C*T*G*G*A-3'.
SEQ ID NO 75

SAMRS I 18mer: 5'-T*G*C*C*C*T*G*T*C*T *C*T*G*G*A*G*G*T-3'
SEQ ID NO 45

SAMRS I 20mer: 5'-T*G*C*C*C*T*G*T*C*T*C*T*G*G*A*G*G*T*T*G-3'
SEQ ID NO 75

Template: 3' ACGGGACAGAGACCTCCAACGACTTCTTTAGCGCGCAG 5'
SEQ ID NO 61
```

SAMRS I 20 mer, SAMRS I 18 mer and SAMRS I 15 mer were elongated on a standard template by using Klenow (exo-) in the presence extra 50 mM NaCl. The sequences were shown as above. $\gamma_{32}$P-labeled 20 mer, 18 mer and 15 mer of SAMRS
primers were annealed to the complementary template first. dNTP (100 µM, final) was then added, followed by Klonew (exo-) polymerase. The reactions were performed at 30° C. At 2 min, 5 min and 10 min, aliquots of reaction mixtures were taken and quenched with 10 mM EDTA in formamide loading buffer. The resulting reaction mixtures were separated on 10% PAGE and visualized by autoradiography.
Internal radiolabel was also carried out in parallel. Cold 20 mer, 18 mer and 15 mer of SAMRS primers were annealed to the complementary template first. Alpha $_{32}$P-dCTP and dNTP was then added, followed by Klonew (exo-). The other reaction conditions and progress were identical to above.

Example 15

Polymerase Read-Through of Templates Containing Consecutive SAMRS Components (FIG. 14)

The purpose of this experiment was demonstrate the read through of templates containing SAMRS components using 6 kinds of NEB thermophilic polymerases at various temperatures.

Methods:

Thermophilic polymerases read-through of the synthesized SAMRS template containing consecutive SAMRS components

```
5'-A*C*G*A*C*T*G*G*T*T*T*C*C*A*A*G*G*GG CTGAAGAAATCGCGCGTC-3'
SEQ ID NO 76

Figure 1:
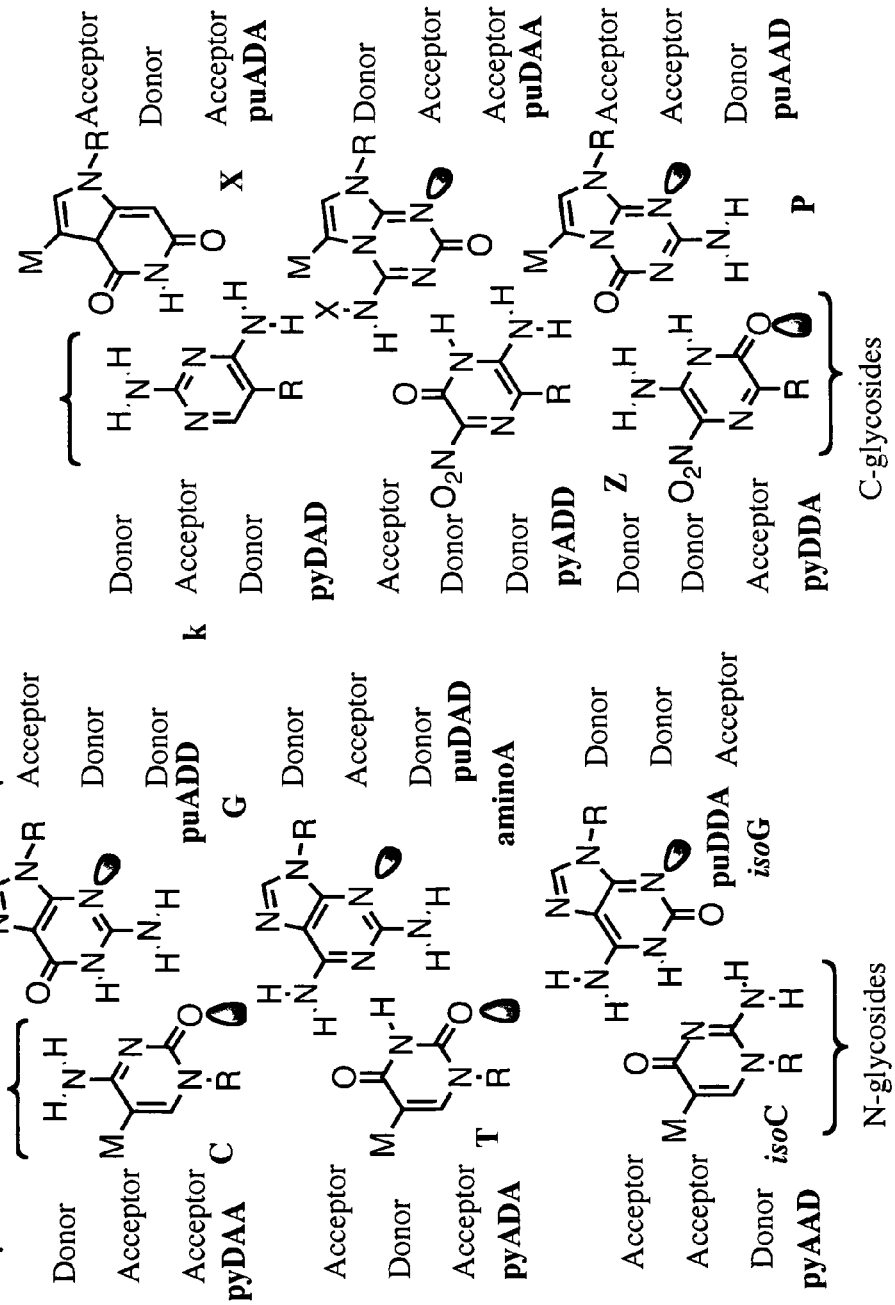
FIG. 1. The AEGIS system. 12 nucleobases in a nucleic acid alphabet that form specific pairs with the constraints of the Watson-Crick geometry. These make an artificially expanded genetic information system (AEGIS) to be applied to tools for systems biology. Pyrimidine base analogs are designated "py", purine by "pu". Upper case letters following a designation indicate the hydrogen bonding pattern of acceptor (A) and donor (D) groups. Thus, cytosine is pyDAA. Note letter designations (Z and P), orbitals holding minor groove unshared electron pairs (shaded lobes; these may be recognition elements for some polymerases), and positions where tags can be appended (M).
Figure 2:
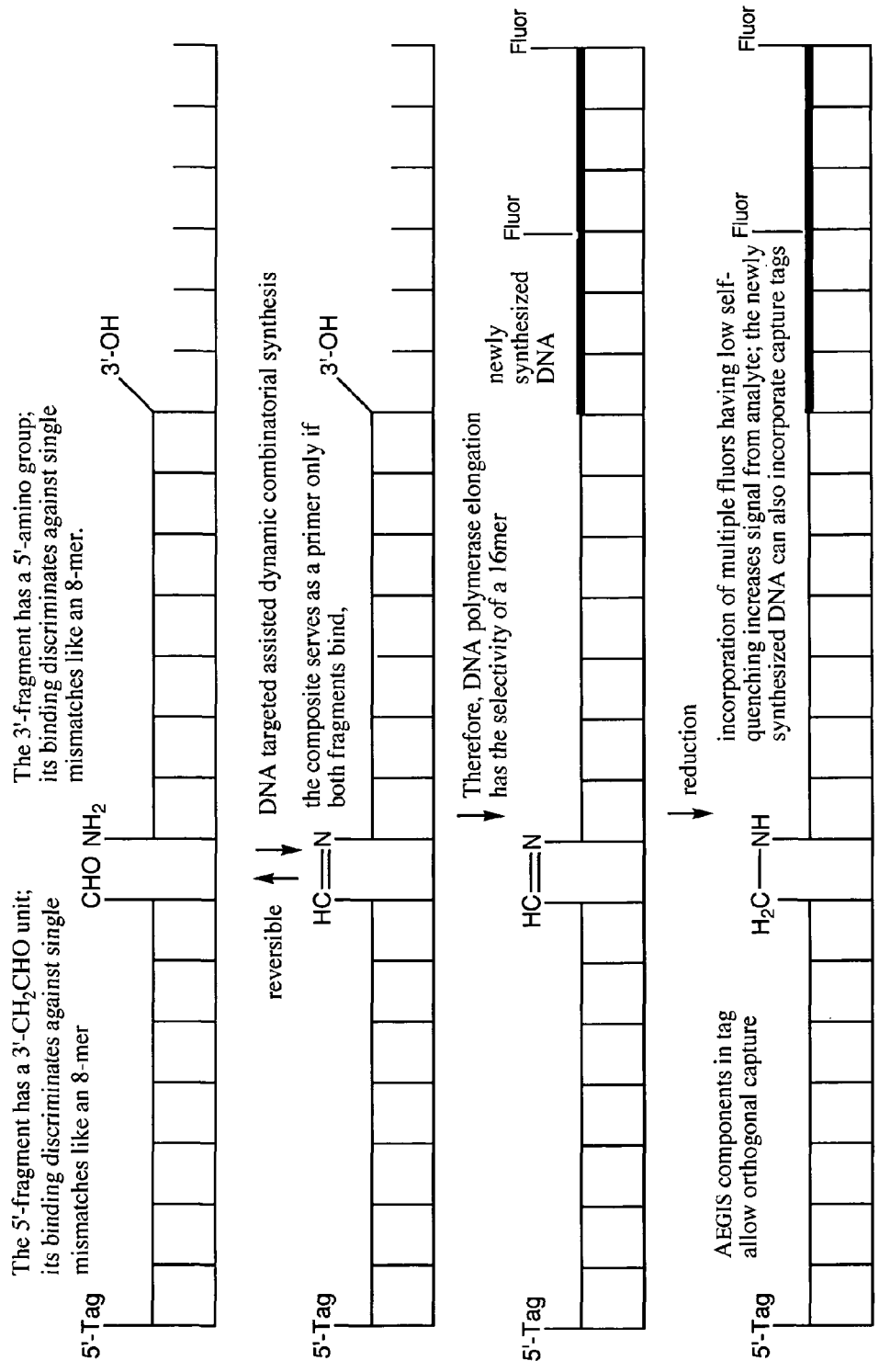
FIG. 2. SNAP2 architecture for primers that dynamically assemble on a template from two fragments, each 8 nucleotides in length, one terminated with 3'-$CH_2CHO$ (on the 5'-DNA fragment), the other with a 5'—$NH_2$ (on the 3'-DNA fragment). These reversibly form a composite, joined via an imine linker under conditions of dynamic equilibrium. Imine formation is reversible in water, and reversibility ensures that the tightest binding complement perfectly matched to the template is formed. Should this composite prime synthesis of DNA using a DNA polymerase, the specificity of priming should be characteristic of a 16-mer (and therefore unique in the human genome), as both sequences must be adjacent on the template for priming to occur. The discrimination against mismatches, however, should be that characteristic of an 8-mer, and therefore be very high. This architecture has a superficial resemblance to one proposed by Studier [Stu89], Szybalski, [Szy90], Kotler et al. [Kot93] and others, where multiple short fragments are ligated as part of a sequencing architecture. In these proposals, the covalent bonding forming step is irreversible, and therefore does not benefit from the features of a dynamic equilibrium. For a description of preliminary data, see [Lea06].
Figure 3:
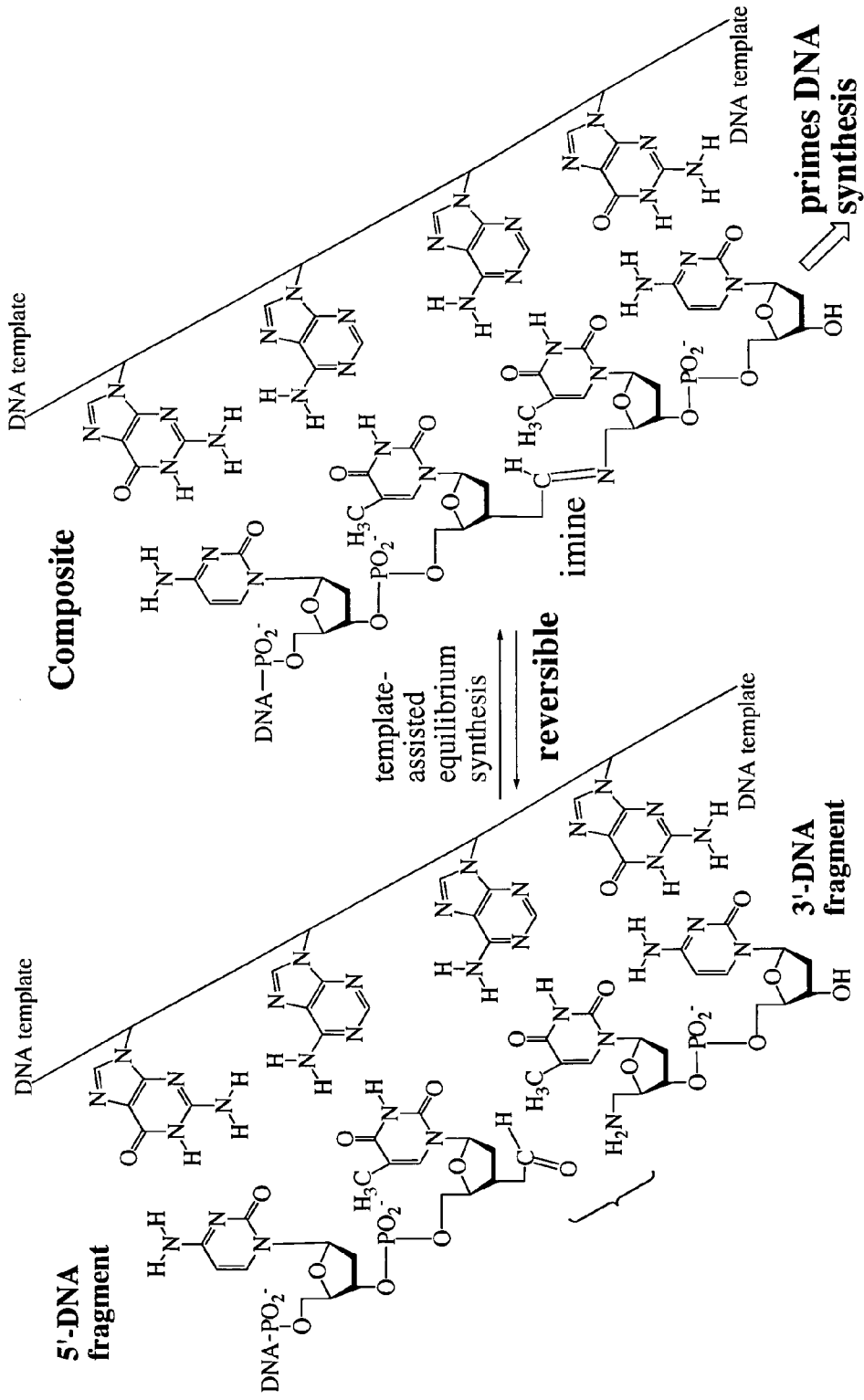
FIG. 3. Details of the chemical implementation of the architecture shown in FIG. 2. Here, an imine linkage is transiently formed from the two primer fragments. For preliminary data, see [Lea06]

3'- GAC TTC TTT AGC GCG CAG -5' SEQ ID NO 62
```

γ-$^{32}$P-labeled primer was annealed to the complementary SAMRS template as above, and then the annealed template-primer complex was contacted with dNTPs in solution (100 µM, final concentration), followed by 6 kinds of NEB thermophilic polymerases as indicated. The reactions were performed at 30° C., 40° C., 50° C., 60° C. and 70° C. for 10 min, and aliquots of reaction mixtures were taken and quenched with 10 mM EDTA in formamide loading buffer. The resulting reaction mixtures were separated on 14% PAGE and visualized by autoradiography. Results: Six different thermophilic polymerases were initially screened for their ability to read through SAMRS in template. Surprisingly and unexpectedly, FIG. 1 showed that the 6 NEB thermophilic polymerases were all able to read through consecutive SAMRS components in templates to some extent. Taq, vent (exo-), Deep Vent (exo-) and Bst DNA polymerases showed better ability to read through the SAMRS template. Taq DNA polymerase performed the best. Also, the read-through full length product increased with increase in the incubation temperature. Since Vent and Deep Vent polymerases contain 3' to 5' exonuclease activity, the hot primers were degraded and the small successive bands were shown on the gel. Taq and Bst DNA polymerases are therefore the preferred polymerases for reading templates containing SAMRS components.

Example 16

Read Through of thioT in Templates (FIG. 15)

A*=2-aminopurine
T*=2-thiothymine

C*=5-methyl-pyrimidin-2-one
G*=hypoxanthine

Taq and Vent (exo-) were then examined to identify difficulties in reading through T* in a template by using the longer primers and various concentrations of dNTPs.
Methods: Thermophilic polymerases read-through of the synthesized SAMRS template containing consecutive SAMRS components by using three new longer primers

```
5'-A*C*G*A*C*T*G*G*G*T*T*T*C*C*A*A*G*G*GGCTGAAGAAATCGCGCGTC-3'
SEQ ID NO 77

Primer 2: 3'-C C CC GAC TTC TTT AGC GCG CAG -5'  SEQ ID NO 78
5'-A*C*G*A*C*T*G*G*G*T*T*T*C*C*A*A*G*G*GGCTGAAGAAATCGCGCGTC-3'
SEQ ID NO 77

Primer 3: 3'-G G T T C C CC GAC TTC TTT AGC GCG CAG-5'
SEQ ID NO 79

5'-A*C*G*A*C*T*G*G*G*T*T*T*C*C*A*A*G*G*GG CTGAAGAAATCGCGCGTC-3'
SEQ ID NO 77

Primer 4: 3'-CCCAAAGGTTCCCC GAC TTC TTT AGC GCG CAG -5'
SEQ ID NO 80
```

Three new γ-$^{32}$P-labeled primers were annealed to the complementary SAMRS template first, dNTPs were then added (100 μM, final), followed by Taq and vent (exo-) polymerases as indicated. The reactions were performed at 30° C., 40° C., 50° C., 60° C. and 70° C. for 10 min, and aliquots of reaction mixtures were taken and quenched with 10 mM EDTA in formamide loading buffer. The resulting reaction mixtures were separated on 14% PAGE and visualized by autoradiography.

Example 17

Read Through of SAMRS in Templates at Different Concentrations of KCl (FIG. 16)

This experiment optimizes conditions of polymerase read-through of the SAMRS-containing template by varying the concentrations of KCl, so as to decrease the pausing during the read through.
Methods: Incorporation of dNTPs opposite SAMRS template in various concentrations of KCl by using three thermophilic polymerases.

```
5'-A*C*G*A*C*T*G*G*G*T*T*T*C*C*A*A*G*G*GGCTGAAGAAATCGCGCGTC-3'
C* = N4-ethylcytosine  SEQ ID NO 76

C* = 5-methyl-pyrimidin-2-one  SEQ ID NO 77

3'-GAC TTC TTT AGC GCG CAG -5'  SEQ ID NO 62
```

γ-$^{32}$P-labeled primer was annealed to the complementary SAMRS template as described above. dNTPs were then contacted in aqueous solution added (100 μM, final concentration of each), followed by three NEB thermophilic polymerases as indicated. The reactions were performed at 50° C. and 70° C. for 10 min and quenched with 10 mM EDTA in formamide loading buffer. The resulting reaction mixtures were separated on 14% PAGE and visualized by autoradiography. The results show that increasing the concentration of KCl decreased pausing.

Example 18

Figure 8:
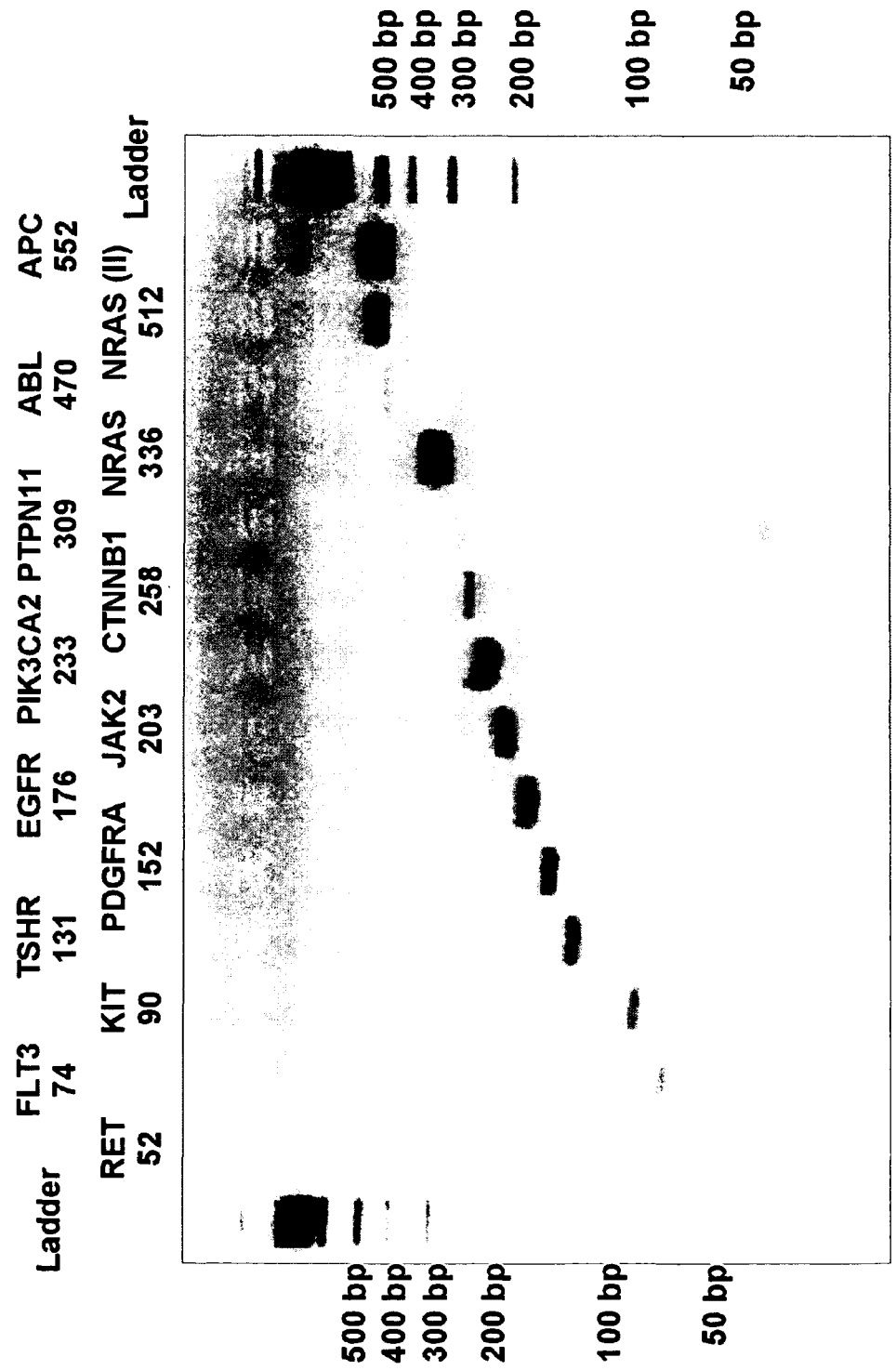
FIG. 8. Monoplexed PCR experiments with standard primers (FIG. 8*a*) and SAMRS chimeric primers (FIG. 8*b*), with SAMRS hydrogen bonding patterns implemented as follows: T* implemented with 2-thiothymine; A* implemented with 2-aminopurine; G* implemented with hypoxanthine; C* implemented with N4-ethylcytosine, with primers targeted against various cancer genes of interest. Template: Human genomic DNA, 25 ng/25 microL Primers each 200 nM. dNTPs each 0.2 mM. Additional 5 mM MgCl$_2$ for SAMRS primers. Taq polymerase: 1.0 units/0.025 mL. 40 cycles: denature at 94° C. for 1 min, then annealing at 55° C. for SAMRS and 60° C. for standard primers for 1 min; then primer extension at 72° C. for 90 sec. Products were resolved on a 3% agarose gel and visualized by phosphorimager (one primer 5'-radiolabeled).
Figure 8:
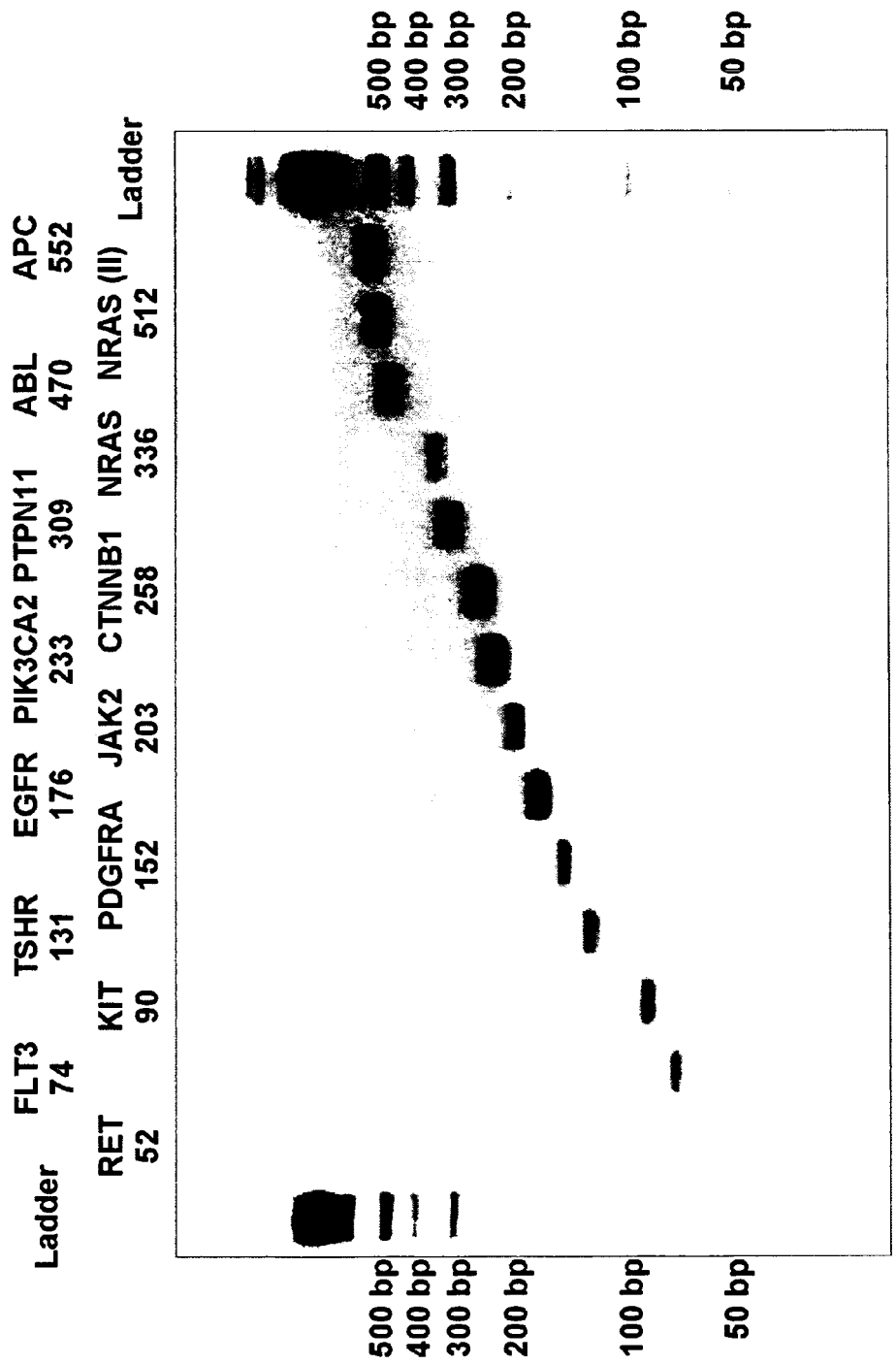

PCR Using SAMRS Primers, with Comparison to Standard Primers, Targeted Against 13 Cancer Genes (FIG. 8 and FIG. 9)

PCR amplifications of various genes of interest to cancer biologists from human genome DNA (Promega). The following chimeric primers were used in a 16+8+1 format (16 standard nucleotides followed by 8 SAMRS nucleotides followed by one standard nucleotides):

TABLE 18.1

Sequences of primers in the primer libraries

RET-52-F: 5'-TTAGGGTCGGATTCCAG*T*T*A*A*A*T*G*G-3' SEQ ID NO 81

RET-52-R: 3'-CC*G*T*T*A*A*C*T*TAGGGAAAAACTAGTA-5' SEQ ID NO 82

FLT3-74-F: 5'-CGGGAAAGTGGTGAAGA*T*A*T*G*T*G*A*C-3' SEQ ID NO 83

FLT3-74-R: 3'-TC*A*C*T*A*A*G*G*TTGATACAACAGTCCC-5' SEQ ID NO 84

KIT-90-F: 5'-AGATTTGTGATTTTGGT*C*T*A*G*C*C*A*G-3' SEQ ID NO 85

KIT-90-R: 3'-CA*C*T*C*A*T*G*G*GTAAGAGACGAACTGT-5' SEQ ID NO 86

TSHR-131-F: 5'-CCGCAGTACAACCCAGG*G*G*A*C*A*A*A*G-3' SEQ ID NO 87

TSHR-131-R: 3'-GT*C*G*T*T*A*A*G*ACTTGTTCGGAGAGTA-5' SEQ ID NO 88

PDGFRA-152-F: 5'-GCTCGCAACGTCCTCCT*G*G*C*A*C*A*A*G-3' SEQ ID NO 89

PDGFRA-152-R: 3'-GT*C*C*G*A*G*T*A*GGAGGAAGTGAAATTA-5' SEQ ID NO 90

EGFR-176-F: 5'-CACAGCAGGGTCTTCTC*T*G*T*T*T*C*A*G-3' SEQ ID NO 91

EGFR-176-R: 3'-CT*C*T*T*T*C*T*T*ATGGTACGTCTTCCTC-5' SEQ ID NO 92

JAK2-203-F: 5'-CTGAAAGTAGGAGAAAG*T*G*C*A*T*C*T*T-3' SEQ ID NO 93

JAK2-203-R: 3'-AG*A*C*A*C*C*T*C*TGCTCTCATTCATTTT-5' SEQ ID NO 94

PIK3CA-233-F: 5'-TATTCGACAGCATGCCA*A*T*C*T*C*T*T*C-3' SEQ ID NO 95

PIK3CA-233-R: 3'-GT*G*T*G*T*T*A*A*TTTGTCGTACGTAACT-5' SEQ ID NO 96

CTNNB1-258-F: 5'-CTAATACTGTTTCGTAT*T*T*A*T*A*G*C*T-3' SEQ ID NO 97

CTNNB1-258-R: 3'-GA*G*T*T*C*T*T*G*TTCATCGACCATTCTC-5' SEQ ID NO 98

PTPN11-309-F: 5'-AATAAAGACCTTTGTGT*T*G*A*G*T*T*G*G-3' SEQ ID NO 99

PTPN11-309-R: 3'-CA*A*C*C*A*G*G*T*CATAATGTACCTTGTA-5' SEQ ID NO 100

NRAS-336-F: 5'-CCATATTTCTTTTCTGC*A*G*G*C*A*T*A*T-3' SEQ ID NO 101

NRAS-336-R: 3'-CT*T*C*T*C*A*T*G*TCACGGTACTCTCTGG-5' SEQ ID NO 102

ABL1-470-F: 5'-CGGGAGCCCCCGTTCTA*T*A*T*C*A*T*C*A-3' SEQ ID NO 103

ABL1-470-R: 3'-TT*C*A*C*C*T*T*A*TAATTTACTTCAAGTA-5' SEQ ID NO 104

NRAS (II)-512-F: 5'-GTACAAACTGGTGGTGG*T*T*G*G*A*G*C*A-3' SEQ ID NO 105

NRAS (II)-512-R: 3'-TC*G*A*T*C*A*A*C*TTCGTCGACTCTGGTC-5' SEQ ID NO 106

APC-552-F: 5'-GTTCATTATCATCTTTG*T*C*A*T*C*A*G*C-3' SEQ ID NO 107

APC-552-R: 3'-CT*T*C*A*T*G*G*A*TTTTTATTTCGTGGAT-5' SEQ ID NO 108

For FIG. 8, showing monoplexed PCR experiments with standard primers (FIG. 8a) and SAMRS chimeric primers (FIG. 8b), SAMRS hydrogen bonding patterns implemented as follows: T* implemented with 2-thiothymine; A* implemented with 2-aminopurine; G* implemented with hypoxanthine; C* implemented with N4-ethylcytosine, with primers targeted against various cancer genes of interest. Template: Human genomic DNA, 25 ng/25 microL Primers each 200 nM. dNTPs each 0.2 mM. For standard primers, $MgCl_2$ concentration in commercially supplied Taq buffer was used (approximately 2 mM). For SAMRS primers, an additional 5 mM $MgCl_2$ was added. Taq polymerase: 1.0 units/0.025 mL.

40 cycles: denature at 94° C. for 1 min, then annealing at 55° C. for SAMRS and 60° C. for standard primers for 1 min; then primer extension at 72° C. for 90 sec. Products were resolved on a 3% agarose gel and visualized by phosphorimager (one primer 5'-radiolabeled).

For FIG. 9, showing five- and ten-fold multiplexed PCR experiments with standard primers (FIG. 9a) and SAMRS chimeric primers (FIG. 9b), with SAMRS hydrogen bonding patterns implemented as follows: T* implemented with 2-thiothymine; A* implemented with 2-aminopurine; G* implemented with hypoxanthine; C* implemented with N4-ethylcytosine, with primers targeted against various cancer genes of interest. Template: Human genomic DNA, 25 ng/25 microL Primers each 200 nM. dNTPs each 1 mM. For standard primers, an additional 2.5 mM $MgCl_2$ was added. For SAMRS primers, an additional 10 mM $MgCl_2$ was added. Taq polymerase: 5.0 units/0.025 mL. 40 cycles: denature at 94° C. for 1 min, then annealing at 55° C. for SAMRS and 60° C. for standard primers for 1 min; then primer extension at 72° C. for 90 sec. Products were resolved on a 3% agarose gel and visualized by phosphorimager (one primer 5'-radiolabeled).

REFERENCES

[All98a] Allawi, H. T., SantaLucia, J. (1998) Nearest-neighbor thermodynamics of internal A-C mismatches in DNA: Sequence dependence and pH effects. *Biochemistry* 37, 9435-9444

[All98b] Allawi, H. T., SantaLucia, J. (1998) Thermodynamics of internal C:T mismatches in DNA. *Nucleic Acids Res.* 26, 2694-2701.

[Ben04] Benner, S. A. (2004) Understanding nucleic acids using synthetic chemistry. *Acc. Chem. Res.* 37, 784-797.

[Bog99] Bogan, J., Ignatovich, L., Stankevich, E. (1999) Reversed (5'->3') oligonucleotide synthesis on oxalyl-CPG support. *Nucleosides Nucleotides Nucl. Acids* 18, 1183-1185.

[Col97] Collins, M. L., Irvine, B., Tyner, D., Fine, E., Zayati, C., Chang, C. A., Horn, T., Ahle, D., Detmer, J., Shen, L. P., Kolberg, J., Bushnell, S., Urdea, M. S., Ho, D. D. (1997) A branched DNA signal amplification assay for quantification of nucleic acid targets below 100 molecules/mL. *Nucl. Acids Res.* 25, 2979-2984.

[Egh92] Egholm, M., Buchardt, O., Nielsen, P. E., Berg, R. H. (1992) Peptide nucleic-acids (PNA); Oligonucleotide analogs with an achiral peptide backbone *J. Am. Chem. Soc.* 114, 1895-1897

[Elb04a] Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.,* 42, 3120-3127.

[Elb04b] Elbeik, T., Surtihadi, J., Destree, M., Gorlin, J., Holodniy, M., Jortani, S. A., Kuramoto, K., Ng, V., Valdes, R., Valsamakis, A. et al. (2004) Multicenter evaluation of the performance characteristics of the Bayer VERSANT HCV RNA 3.0 assay (bDNA). *J. Clin. Microbiol.,* 42, 563-569.

[Gam04] Gamper H B, Gewirtz A, Edwards J, et al. (2004) Modified bases in RNA reduce secondary structure and enhance hybridization. *Biochemistry* 43, 10224-10236

[Gey03] Geyer, C. R., Battersby, T. R., Benner, S. A. (2003) Nucleobase pairing in expanded Watson-Crick like genetic information systems. The nucleobases. *Structure* 11, 1485-1498.

[Kot93] Kotler, L. E., Zevin-Sonkin, D., Sobolev, I. A., Beskin, A. D., Ulanovsky, L. E. (1993) DNA sequencing: Modular primers assembled from a library of hexamers or pentamers. *Proc. Natl. Acad. Sci.* 90, 4241-4245.

[Lah08] Lahoud, G., Timoshchuk, V., Lebedev, A., de Vega, M., et al. (2008) Enzymatic synthesis of structure-free DNA with pseudo-complementary properties. *Nucl. Acids Res.* 36, 3409-19.

[Lan00] Lan, T., McLaughlin, L. W. (2000) Minor groove hydration is critical to the stability of DNA duplexes. *J. Am. Chem. Soc.* 122, 6512-6513.

[Lea06] Leal, N. A., Sukeda, M., Benner, S. A. (2006) Dynamic assembly of primers on nucleic acid templates. *Nucleic Acids Res* 34, 4702-4710.

[Mar85] Martin, F. H., Castro, M. M., Aboul-ela, F., Tinoco, I. Jr. (1985) Base-pairing involving deoxyinosine—implications for probe design. *Nucl. Acids Res.* 13, 8927-8938.

[Mat98] Mathews, D. H., Andre, T. C., Kim, J., Turner, D. H., Zuker, M. (1998) An updated recursive algorithm for RNA secondary structure prediction with improved thermodynamic parameters. *Molecular Modeling of Nucleic Acids. ACS Symposium Series* 682, 246-257.

[Ngu00] Nguyen, H.-K, Southern, E. M. (2000) Minimising the secondary structure of DNA targets by incorporation of a modified deoxynucleoside. Implications for nucleic acid analysis by hybridization. *Nucl. Acids Res.* 28, 3904-3909.

[Ngu98] Nguyen, H.-K. et al. (1998) The stability of duplexes involving AT and/or $G^{4Et}C$ base pairs is not dependent on their raio content. Implication for DNA sequencing by hybridization. *Nucl. Acids Res.* 28, 3904-3909.

[San98] SantaLucia, J. (1998) A unified view of polymer, dumbbell, and oligonucleotide DNA nearest-neighbor thermodynamics. *Proc. Nat. Acad. Sci. USA* 95, 1460-1465

[Sil99] Silverman, B. D., Pitman, M. C., Platt, D. E. (1999) Molecular moment similarity between several nucleoside analogs of thymidine and thymidine. *Journal of Biomolecular Structure & Dynamics* 16, 1169-1175.

[Sin01] Singleton, S. F., Shan, F., Kanan, M. W., McIntosh, C. M., Stearman, C. J., Heim, J. S., Webb, K. J. (2001) Facile synthesis of a fluorescent deoxycytidine analog suitable for probing the recA nucleoprotein filament. *Org. Lett.* 3919-3922.

[Sis05] Sismour, A. M., Benner, S. A. (2005) The use of thymidine analogs to improve the replication of an extra DNA base pair: A synthetic biological system. *Nucl. Acids Res.* 33, 5640-5646.

[Stu89] Studier, F. W. (1989) A strategy for high-volume sequencing of cosmid DNAs: random and directed priming with a library of oligonucleotides. *Proc. Natl. Acad. Sci. USA* 86, 6917-6921.

[Szy90] Szybalski, W. (1990) Proposal for sequencing DNA using ligation of hexamers to generate sequential elongation primers (SPEL-6). *Gene* 90, 177-178.

[Viv04] Vives, M., Eritja, R., Tauler, R., Marquez, V. E., Gargallo, R. (2004) Synthesis, stability, and protonation studies of a self-complementary dodecamer containing the modified nucleoside 2'-deoxyzebularine. *Biopolymers* 73, 27-43.

[Woo03] Woods, K. K., Lan, T., McLaughlin, L. W., Williams, L. D. (2003) The role of minor groove functional groups in DNA hydration. *Nucleic Acids Research* 31, 1536-1540.

[Zha01] Zhan, Z. Y. J., Ye, J. D., Li, X. Y., Lynn, D. G. (2001) Replicating DNA differently. *Current Org. Chem.* 5, 885-902.

What is claimed is:

1. A process for amplifying one or more oligonucleotides by enzymatic template-directed primed polymerization, wherein said process comprises (a) contacting in aqueous solution one or more pairs of primers with said oligonucleotide, a polymerase, and standard nucleoside triphosphates, and (b) incubating the mixture for a preselected length of time, wherein each of said primers has the formula:

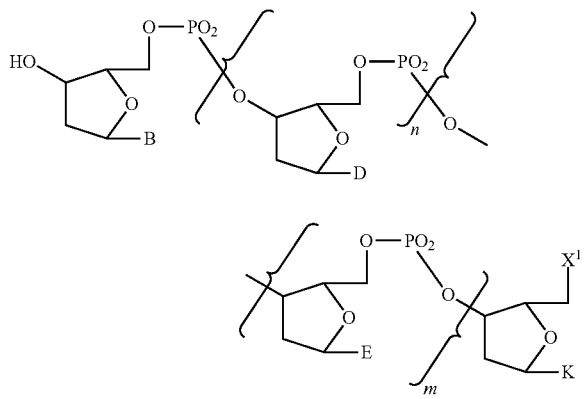

wherein X is selected from the group consisting of OH, O-phosphate, O-oligonucleotide, —$NH_2$, and a phosphate or an amino group linked to a biotin or fluorescent tag, B is independently selected from the group consisting of adenine, thymine, guanine, cytosine, diaminopurine, uracil, A*, T*, G*, and C*, D is independently selected from the group consisting of A*, T*, G*, and C*, E is independently selected from the group consisting of A, T, G, and C, and K is independently selected from the group consisting of A, T, G, C, A*, T*, G*, and C*, wherein n is an integer from 4 to 25 and m is an integer from 2 to 10, wherein the first member of said pair is complementary to said oligonucleotide at a portion of it, and the second member of said pair is formally the same as a segment of the same oligonucleotide at a position between 10 and 1000 nucleotides in the 5'-direction from the portion, where A* does not contribute to the stability of a duplex when paired with T* but does when it is paired with thymine, T* does not contribute to the stability of a duplex when paired with A* but does when it is paired with adenine, G* does not contribute to the stability of a duplex when paired with C* but does when it is paired with cytosine, and C* does not contribute to the stability of a duplex when paired with G* but does when it is paired with guanine.

2. The process of claim 1 wherein A* is selected from the group consisting of 2-aminopurine and 2,6-diaminopurine.

3. The process of claim 1 wherein T* is selected from the group consisting of 2-thiothymidine and 2-thiouracil.

4. The process of claim 1 wherein G* is hypoxanthine.

5. The process of claim 1 wherein C* is selected from the group consisting of $N^4$-ethylcytosine and $N^4$-methylcytosine.

6. The process of claim 1 wherein the sum of m and n in said primers is at least 15.

7. The process of claim 1 wherein the D units are independently selected from the group consisting of T*, A*, G* and C*.

8. The process of claim 1 wherein the B units are independently selected from the group consisting of thymine, adenine, guanine, cytosine.

9. The process of claim 1 wherein A* is selected from the group consisting of 2-aminopurine and 2,6-diaminopurine.

10. The process of claim 1 wherein T* is selected from the group consisting of 2-thiothymidine and 2-thiouracil.

11. The process of claim 1 wherein G* is hypoxanthine.

12. The process of claim 1 wherein C* is selected from the group consisting of $N^4$-ethylcytosine and $N^4$-methylcytosine.

13. The process of claim 1 wherein more than 5 of said primer pairs are contacted.

14. A composition of matter that comprises a plurality of oligonucleotides, each oligonucleotide having the formula

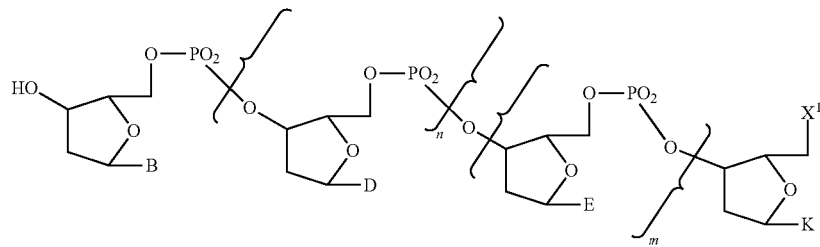

wherein is selected from the group consisting of OH, O-phosphate, O-oligonucleotide, —NH$_2$, and a phosphate or an amino group linked to a biotin or fluorescent tag, B is independently selected from the group consisting of adenine, thymine, guanine, cytosine, diaminopurine, uracil, A*, T*, G*, and C*, D is independently selected from the group consisting of A*, T*, G*, and C*, E is independently selected from the group consisting of A, T, G, and C, and K is independently selected from the group consisting of A, T, G, C, A*, T*, G*, and C*, wherein n is an integer from 4 to 25 and m is an integer from 2 to 10, wherein A* is selected from the group consisting of 2-aminopurine and 2,6-diaminopurine, G* is hypoxanthine, T* is selected from the group consisting of 2-thiothymidine and 2-thiouracil, and C* is selected from the group consisting of N-ethylcytosine and N-methylcytosine, wherein the first member of said pair is complementary to a target sequence at a portion of it, and the second member of said pair is formally the same as a segment of the same target sequence at a position between 10 and 1000 nucleotides in the 5'-direction from the portion.

15. The composition of claim 14 wherein at least one B or one D is selected from the group consisting of N-ethylcytosine and N-methylcytosine.

16. The composition of claim 14 wherein said oligonucleotides are dissolved in water at a concentration of 100 nanomolar or greater.

\* \* \* \* \*